US008828659B2

(12) United States Patent
Farrell

(10) Patent No.: US 8,828,659 B2
(45) Date of Patent: Sep. 9, 2014

(54) METHOD FOR PRODUCING NUCLEIC ACID PROBES

(71) Applicant: Ventana Medical Systems, Inc., Tucson, AZ (US)

(72) Inventor: Michael Farrell, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 13/792,590

(22) Filed: Mar. 11, 2013

(65) Prior Publication Data

US 2013/0183670 A1   Jul. 18, 2013

Related U.S. Application Data

(62) Division of application No. 11/849,060, filed on Aug. 31, 2007, now Pat. No. 8,420,798.

(60) Provisional application No. 60/841,896, filed on Sep. 1, 2006, provisional application No. 60/892,571, filed on Mar. 2, 2007.

(51) Int. Cl.
*C12Q 1/68* (2006.01)
*C12P 19/34* (2006.01)

(52) U.S. Cl.
CPC .................................. *C12Q 1/6876* (2013.01)
USPC ........................................ 435/6.1; 435/91.1

(58) Field of Classification Search
None
See application file for complete search history.

(56) References Cited

U.S. PATENT DOCUMENTS

| | | | |
|---|---|---|---|
| 5,447,841 A | 9/1995 | Gray et al. | |
| 5,643,761 A | 7/1997 | Fisher et al. | |
| 5,648,211 A | 7/1997 | Fraiser et al. | |
| 5,648,245 A | 7/1997 | Fire et al. | |
| 5,731,171 A | 3/1998 | Bohlander | |
| 5,756,696 A | 5/1998 | Gray et al. | |
| 6,124,120 A | 9/2000 | Lizardi | |
| 6,218,152 B1 | 4/2001 | Auerbach | |
| 6,280,929 B1 | 8/2001 | Gray et al. | |
| 6,280,949 B1 | 8/2001 | Lizardi | |
| 6,291,187 B1 | 9/2001 | Kingsmore et al. | |
| 6,323,009 B1 | 11/2001 | Lasken et al. | |
| 6,569,621 B1 | 5/2003 | Cremer et al. | |
| 6,607,877 B1 | 8/2003 | Gray et al. | |
| 6,617,137 B2 | 9/2003 | Dean et al. | |
| 6,632,609 B2 | 10/2003 | Lizardi | |
| 6,638,722 B2 | 10/2003 | Ji et al. | |
| 6,642,034 B2 | 11/2003 | Lizardi | |
| 6,797,474 B2 | 9/2004 | Lizardi | |
| 6,828,097 B1 | 12/2004 | Knoll et al. | |
| 6,942,970 B2 | 9/2005 | Isola et al. | |
| 6,977,148 B2 | 12/2005 | Dean et al. | |
| 7,014,997 B2 | 3/2006 | Knoll et al. | |
| 8,420,798 B2 * | 4/2013 | Farrell | ........................ 536/24.3 |
| 2001/0051342 A1 | 12/2001 | Farrell | |
| 2003/0022166 A1 | 1/2003 | Collins et al. | |
| 2004/0161742 A1 | 8/2004 | Dean et al. | |
| 2005/0048498 A1 | 3/2005 | Woudenberg et al. | |
| 2005/0112636 A1 | 5/2005 | Hurt et al. | |
| 2005/0164213 A1 | 7/2005 | Tabor et al. | |
| 2005/0181394 A1 | 8/2005 | Steemers et al. | |
| 2006/0110744 A1 | 5/2006 | Sampas et al. | |
| 2006/0160116 A1 | 7/2006 | Christian et al. | |

FOREIGN PATENT DOCUMENTS

WO    WO 01/88089 A2    11/2001

OTHER PUBLICATIONS

Abd-Elsalam, "Bioinformatic Tools and Guideline for PCR Primer Design," *Afr. J. Biotechnol.* 2:91-95, 2003.
Bedell et al., "MaskerAid: A Performance Enhancement to RepeatMasker," *Bioformatics* 16:1040-1041, 2000.
Bourne, "Handbook of Immunoperoxidase Staining Methods," DAKO Corporation, Santa Barbara, California, 1983.
Cao et al., "Adenovirus-Mediated Ribonucleotide Reductase R1 Gene Therapy of Human Colon Adenocarcinoma," *Clin. Cancer Res.* 9:4553-4561, 2003.
Chan et al., "A Human Transferrin-Vascular Endothelial Growth Factor (hnTf-VEGF) Fusion Protein Containing an Integrated Binding Site for (111)In for Imaging Tumor Angiogenesis," *J. Nucl. Med.* 46:1745-1752, 2005.
Davison et al., "Subtracted, Unique-Sequence, In Situ Hybridization Experimental and Diagnostic Applications," *Am. J. Pathol.* 153:1401-1409, 1998.
Dhami et al., "Exon Array CGH: Detection of Copy-Number Changes at the Resolution of Individual Exons in the Human Genome," *Am. J. Hum. Genet.* 76:750-762, 2005.
Gonzalez et al., "Multiple Displacement Amplification as a Pre-Polymerase Chain Reaction (pre-PCR) to Process Difficult to Amplify Samples and Low Copy Number Sequences from Natural Environments," *Environ. Microbiol.* 7:1024-1028, 2005.
Gzyl et al., "Amplified Fragment Length Polymorphism (AFLP) Versus Randomly Amplified Polymorphic DNA (RAPD) as New Tools for Inter- and Intra-species Differentiation within *Bordetella*," *J. Med. Microbiol.* 54:333-346, 2005.
Hotta et al., "Molecular Cloning and Characterization of an Antigen Associated with Early Stages of Melanoma Tumor Progression," *Cancer Res.* 48:2955-2962, 1988.

(Continued)

*Primary Examiner* — Kenneth R. Horlick
*Assistant Examiner* — David Thomas
(74) *Attorney, Agent, or Firm* — Klarquist Sparkman, LLP

(57) ABSTRACT

The present disclosure provides nucleic acid probes, as well as kits that include such probes. Methods for producing and using (for example in chromosomal in situ hybridization) the probes are also provided. Such probes in some examples are used to detect chromosomal abnormalities or the presence of a pathogen.

31 Claims, 10 Drawing Sheets

(56) References Cited

OTHER PUBLICATIONS

Hull et al., "Analysis of Mutations and Alternative Splicing Patterns in the CFTR Gene Using mRNA Derived from Nasal Epithelial Cells," *Hum. Mol. Gen.* 3:1141-1146, 1994.

Inoue et al., "Improvements of Rolling Circle Amplification (RCA) Efficiency and Accuracy Using *Thermus thermophilus* SSB Mutant Protein," *Nucleic Acids Res.* 34:e69, 2006.

Jack and Hardman, "Sequence Organization in Nuclear Deoxyribonucleic Acid from *Physarum polycephalum*," *Biochem. J.* 187:105-113, 1980.

Korn, "A Comprehensive Sequence Analysis Program for the IBM Personal Computer," *Nucleic Acids Res.* 12:581-599, 1984.

Lefebvre et al., "FORRepeats: Detects Repeats on Entire Chromosomes and Between Genomes," *Bioinformatics* 19:319-326, 2003.

Levy and Mattei, Chapter 9 "Applications of Chromosomal in situ Hybridization," in *Gene probes 2: A Practical Approach*, Hames and Higgins (eds.), pp. 211-243, Oxford University Press, 1995.

Lewis et al., "New Approaches to the Analysis of Palindromic Sequences from the Human Genome: Evolution and Polymorphism of an Intronic Site at the NF1 Locus," *Nucleic Acids Res.* 33:e186, 2005.

Lichter et al., "Rapid Detection of Human Chromosome 21 Aberrations by In Situ Hybridization," *Proc. Natl. Acad. Sci. USA* 85:9664-9668, 1988.

Liu et al., "Development and Validation of a T7 Based Linear Amplification for Genomic DA," *BMC Genomics* 4:19, 2003.

Mantripragada et al., "Genomic Microarrays in the Spotlight," *Trends Genet.* 20:87-94, 2004.

Mantripragada, "Microarray-Based Comparative Genomic Hybridization in Neurofibromatoses and DiGeorge Syndrome," *Digital Comprehensive Summaries of Uppsala Dissertations from the Faculty of Medicine* 26, 70 pp., Acta Universitatis Upsaliensis, Uppsala, Sweden, 2005.

Mueller and Brueck, "Whole Genome Amplification for Single Cell Biology," Sigma-Aldrich Corporation, St. Louis, MO, 2006.

Mühlmann, "Molecular Cytogenetics in Metaphase and Interphase Cells for Cancer and Genetic Research, Diagnosis and Prognosis. Application in Tissue Sections and Cell Suspensions," *Genet. Mol. Res.* 1:117-127, 2002.

Musco et al., "Comparison of Flow Cytometry and Laser Scanning Cytometry for the Intracellular Evaluation of Adenoviral Infectivity and p53 Protein Expression in Gene Therapy," *Cytometry* 33:290-296, 1998.

Nagesha et al., "Application of Linker-Ligation-PCR for Construction of Phage Display Epitope Libraries," *J. Virol. Methods* 60:147-154, 1996.

Notomi et al., "Loop-Mediated Isothermal Amplification of DNA," *Nucleic Acids Res.* 28:e63, 2000.

Panelli et al., "Ligation Overcomes Terminal Underrepresentation in Multiple Displacement Amplification of Linear DNA," *BioTechniques* 39:174-180, 2005.

Paul and Apgar, "Single-Molecule Dilution and Multiple Displacement Amplification for Molecular Haplotyping," *Biotechniques* 38:553-559, 2005.

Peng et al., "Multiple PCR Analyses on Trace Amounts of DNA Extracted from Fresh and Paraffin Wax Embedded Tissues after Random Hexamer Primer PCR Amplification," *J. Clin. Pathol.* 47:605-608, 1994.

Pinkel et al., "Cytogenetic Analysis Using Quantitative, High-Sensitivity, Fluorescence Hybridization," *Proc. Natl. Acad. Sci. USA* 83:2934-2938, 1986.

Pinkel et al., "Fluorescence In Situ Hybridization with Human Chromosome-Specific Libraries: Detection of Trisomy 21 and Translocations of Chromosome 4," *Proc. Natl. Sci. USA* 85:9138-9142, 1988.

Poddighe et al., "Human Papilloma Virus Detection by In Situ Hybridisation Signal Amplification Based on Biotinylated Tyramine Deposition," *J. Clin. Pathol.: Mol. Pathol.* 49:M340-M344, 1996.

Potgieter et al., "Cloning of Complete Genome Sets of Six dsRNA Viruses Using an Improved Cloning Method for Large dsRNA Genes," *J. Gen. Virol.* 83:2215-2223, 2002.

Radelof et al., "Preselection of Shotgun Clones by Oligonucleotide Fingerprinting: An Efficient and High Throughput Strategy to Reduce Redundancy in Large-Scale Sequencing Projects," *Nucleic Acids Res.* 26:5358-5364, 1998.

Roylance, "Methods of Molecular Analysis: Accessing Losses and Gains in Tumours," *J. Clin. Pathol.: Mol. Pathol.* 55:25-28, 2002.

Strauss et al., "Ligation-Mediated Suppression-PCR as a Powerful Tool to Analyse Nuclear Gene Sequences in the Green Alga *Chlamydomonas reinhardtii*," *Photosynth. Res.* 70:311-320, 2001.

Takahara et al., "A New Retrovirus Packaging Cell for Gene Transfer Constructed from Amplified Long Terminal Repeat-Free Chimeric Proviral Genes," *J. Virol.* 66:3725-3732, 1992.

Tanner et al., "Chromogenic In Situ Hybridization: A Practical Alternative for Fluorescence In Situ Hybridization to Detect HER-2/neu Oncogene Amplification in Archival Breast Cancer Samples," *Am. J. Pathol.* 157:1467-1472, 2000.

van de Lagemaat et al., "Genomic Deletions and Precise Removal of Transposable Elements Mediated by Short Identical DNA Segments in Primates," *Genome Res.* 15:1243-1249, 2005.

Vieux et al., "Primer Design for PCR and Sequencing in High-Throughput Analysis of SNPs," *Biotechniques* 32:S28-S32, 2002.

Walker et al., Isothermal In Vitro Amplification of DNA by a Restriction Enzyme/DNA Polymerase System, *Proc. Natl. Sci. USA* 89:392-396, 1992.

Walker et al., "Strand Displacement Amplification—An Isothermal, In Vitro DNA Amplification Technique," *Nucleic Acids Res.* 20:1691-1696, 1992.

Wang et al., "DNA Amplification Method Tolerant to Sample Degradation," *Genome Res.* 14:2357-2366, 2004.

White et al., "Concatemer Chain Reaction: A Taq DNA-Polymerase-Mediated Mechanism for Generating Long Tandemly Repetitive DNA Sequences," *Anal. Biochem.* 199:184-190, 1991.

Zhang et al., "Amplification of Target-Specific, Ligation-Dependent Circular Probe," *Gene* 211:277-285, 1998.

Zhang, "DNA Amplification: Current Technologies and Applications," *Expert Rev. Mol. Diagn.* 5:127-129, 2005.

Zhong et al., "Simultaneous Detection of Microsatellite Repeats and SNPs in the Macrophage Migration Inhibitory Factor (MIF) Gene by Thin-Film Biosensor Chips and Application to Rural Field Studies," *Nucleic Acids Res.* 33:e121, 2005.

\* cited by examiner

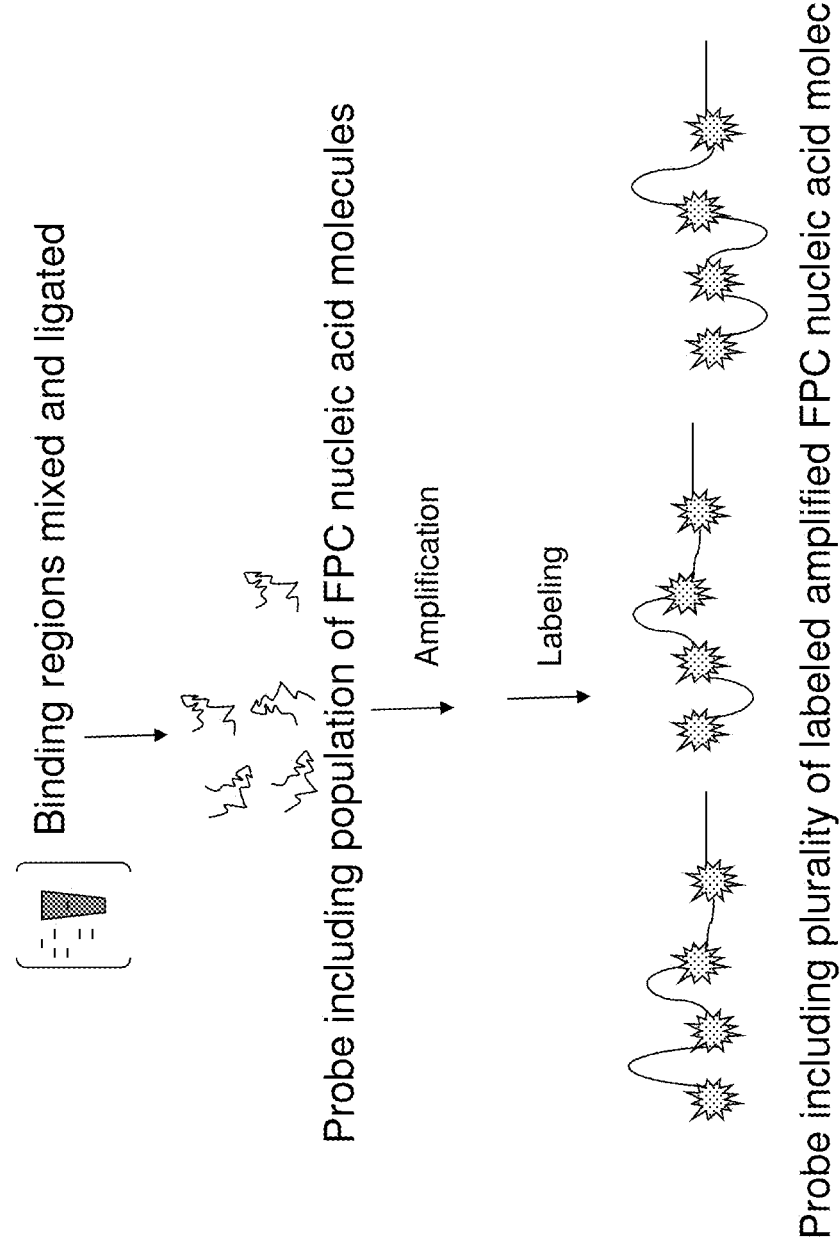

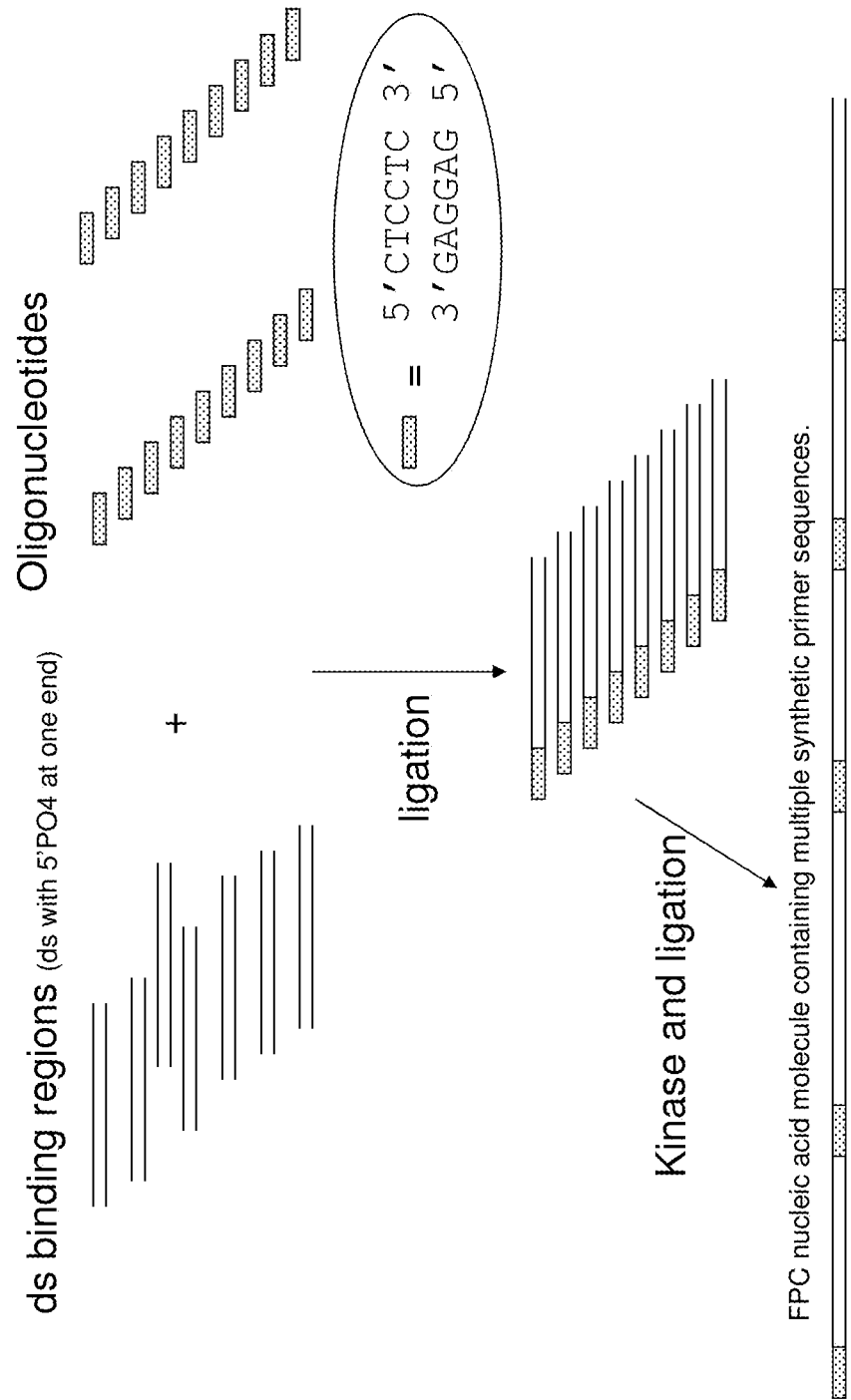

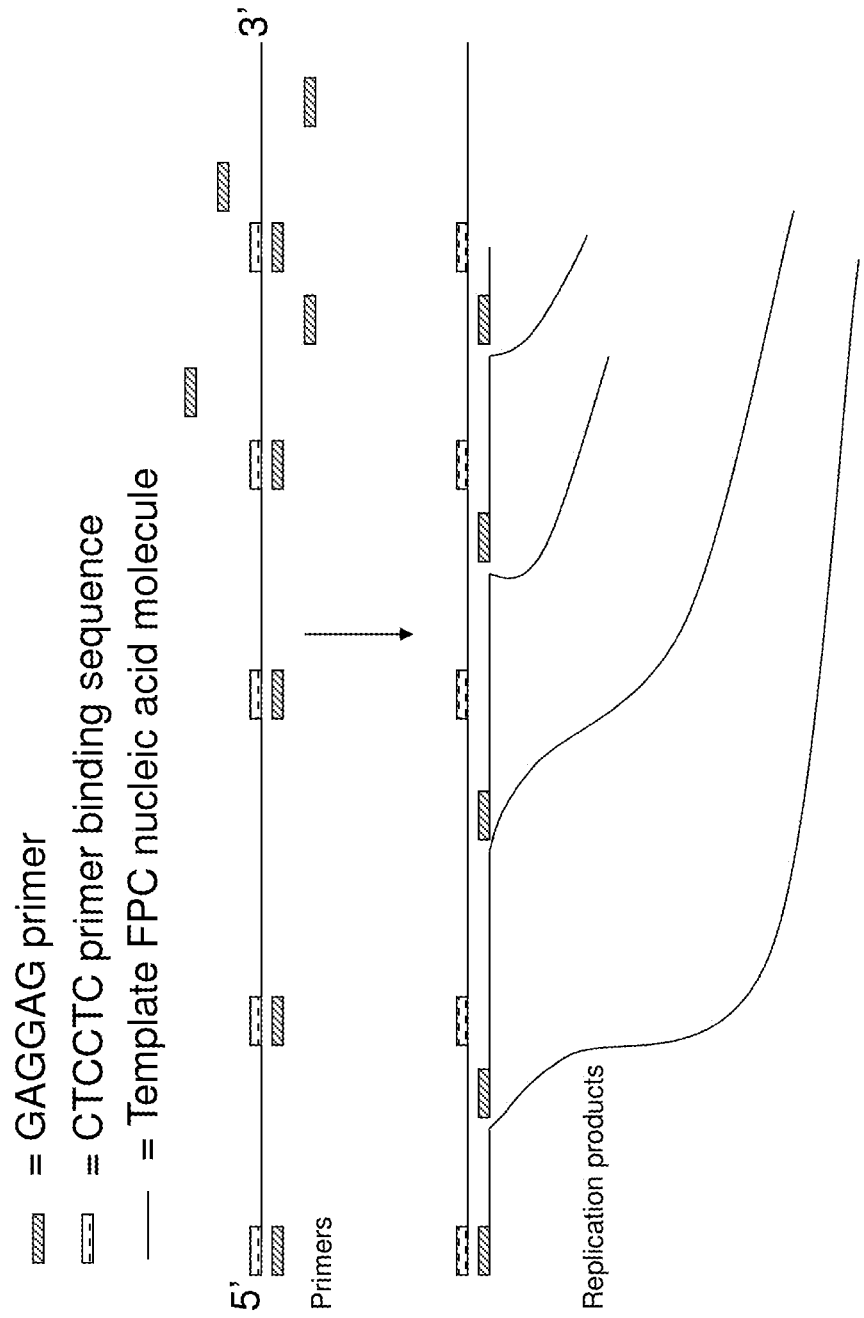

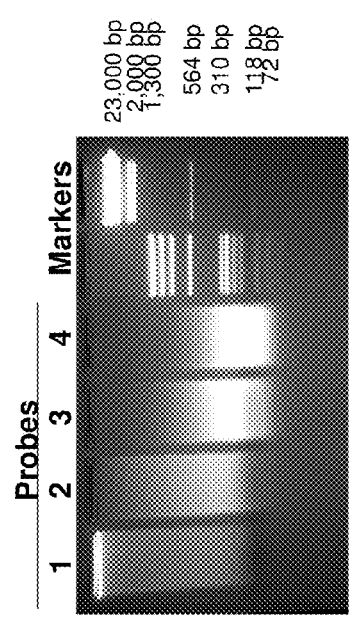
FIG. 7
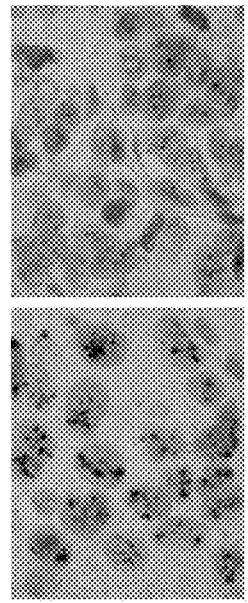
FIG. 8A
FIG. 8B
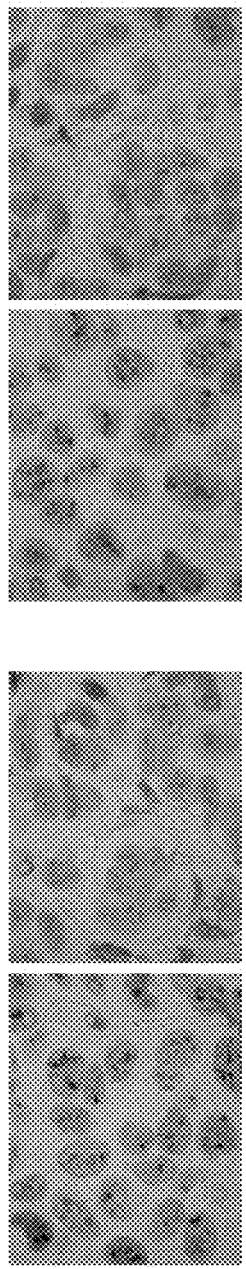
FIG. 8C
FIG. 8D

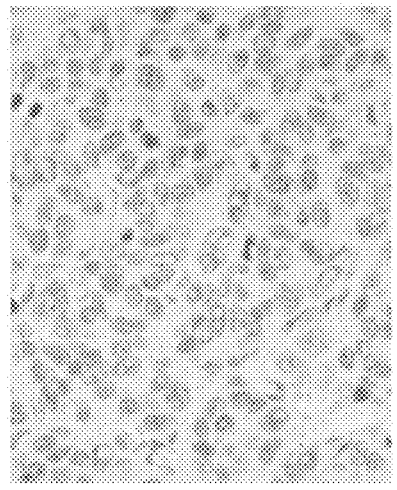
FIG. 9A
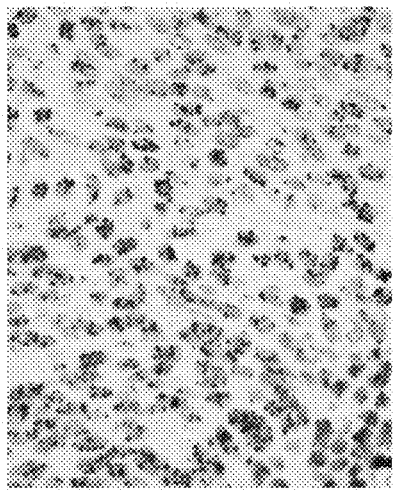
FIG. 9B
FIG. 10
| Negative Kidney | Positive Kidney | | |
|---|---|---|---|
| BKV probe 1 ug/ml 10X CISH detection | | | |
| BKV probe 2 ug/ml 10X SISH detection | | | |

SEQUENCE LISTING

<160> NUMBER OF SEQ ID NOS: 360

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide primer.

<400> SEQUENCE: 1
aaatgattag caaggccaga agtc                                          24

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 2
aactggacaa gctctttggg a                                             21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 3
ccagctccaa aaatgaaaaa g                                             21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 4
aaccaggcag gcaacttatt a                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 5
ttcaatgacc agactccttg c                                             21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 6
taatgcatgg taggaccgaa t                                             21

<210> SEQ ID NO 7
<211> LENGTH: 21
<212> TYPE: DNA
<213> ORGANISM: Artificial Sequence

```
<220> FEATURE:
<223> OTHER INFORMATION: Synthetic oligonucleotide primer.

<400> SEQUENCE: 7
attagccagc attttgtgac c                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 8
gaaccaacag gatgtgcgat a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 9
ttcaaactgc aaaaccctgt g                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 10
gagagagaca ggcacacatg g                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 11
accctgcccc acacatctac t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 12
ccctgctcta gcctttgttc t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 13
ctgaacttcc acccccttta c                                              21
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 14
gcagtacgtg gcagatgtga a                                               21

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 15
gaggaggtaa agaggtccca g                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 16
ctctcctgcc tttctgactc c                                               21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 17
gcctcccact tttctctttt c                                               21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 18
ccagagcttt ctccaggtca c                                               21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 19
ccccagagtc tggtgctact t                                               21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide primer.
```

```
<400> SEQUENCE: 20
atggctgtgg tttgtgatgg t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 21
acaccatgaa ttgttgaagc c                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 22
taatgcgttt tcctctctgg g                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 23
ggagtgatgt ccaccctgtt c                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 24
atgcgtggta gggcatttaa g                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 25
atggacaact cactcctccc t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 26
ccactcccca ttgttgttgt t                                              21

<210> SEQ ID NO 27
```

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 27
attccagcca acaataatgg g                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 28
aagttgtgga cagtcgagac g                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 29
tcgatgtgac tgtctcctcc c                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 30
ggacacctct aaccctgatc c                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 31
agtctccatg gctggtcaat g                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 32
ccatcagaaa cgaattgtcc c                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 33
tccagggctg taaaatcatc a                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 34
tggttctttg cccactatgg t                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 35
aaactgtgcc tcgctagaca a                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 36
tggaattgag attgctccaa g                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 37
tgaaaaatcc aagaatcagg g                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 38
caccacttca ccctcctctc t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 39
agggtctctc cattccagaa c                                              21

<210> SEQ ID NO 40
<211> LENGTH: 21
<212> TYPE: DNA

```
<213> ORGANISM: Artificial Sequence
<220> FEATURE:
<223> OTHER INFORMATION: Synthetic oligonucleotide primer.

<400> SEQUENCE: 40
catactcctc ccagtgctcc t                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 41
cagaccagaa cgagggagag t                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 42
tttgaggaca tcaccatgac a                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 43
cggacactaa gggagatgga t                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 44
accacttacc tgaccactgg c                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 45
cgttgtagga ggattcaagc a                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 46
gcgacctgtt ccaaaagtct c                                              21
```

```
<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 47
caggtgggag agggaagata a                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 48
ctggaaagag gaaggaggac a                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 49
cttcctccag gtctcatgct t                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 50
tctccatagc tccaagcaca c                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 51
ccctacctcc cactctcact c                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 52
ggctaggaaa cgcctactga g                                              21

<210> SEQ ID NO 53
<211> LENGTH: 21
<212> TYPE: DNA
<213> ORGANISM: Artificial Sequence
<220> FEATURE:
```

<223> OTHER INFORMATION: Synthetic oligonucleotide primer.

<400> SEQUENCE: 53
cagatgaatg ctaagcccaa a                                      21

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 54
ccacatcagt gggacaaaag a                                      21

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 55
cctggctctt tgccaataaa t                                      21

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 56
cgcagagcct gtgttcttat c                                      21

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 57
ggctgaagtc ctgaaggtca t                                      21

<210> SEQ ID NO 58
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 58
caggtccaag aagagggaag a                                      21

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 59
tgaacaggag tcaaagctgg a                                      21

```
<210> SEQ ID NO 60
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 60
gacacgcaga gacactcagg a                                            21

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 61
ataagttcag cagagcctcc g                                            21

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 62
aaacacatct tgcttgggag g                                            21

<210> SEQ ID NO 63
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 63
gtccctttgg aacttgcaga t                                            21

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 64
ccatctcgct ccctacaaag t                                            21

<210> SEQ ID NO 65
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 65
tagtgactga gggtggaagg g                                            21

<210> SEQ ID NO 66
<211> LENGTH: 21
<212> TYPE: DNA
<213> ORGANISM: Artificial Sequence
<220> FEATURE:
<223> OTHER INFORMATION: Synthetic oligonucleotide primer.
```

<400> SEQUENCE: 66
cctgtgcaag gttacatcca a                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 67
gcgacctgtt ccaaaagtct c                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 68
cgttgtagga ggattcaagc a                                              21

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 69
caggtgttgg ggtagaactg g                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 70
cggacactaa gggagatgga t                                              21

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 71
tccagatgga gacacatttg c                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 72
aacagtgcag actgcttcag a                                              21

<210> SEQ ID NO 73
<211> LENGTH: 21

-continued

```
<212> TYPE: DNA
<213> ORGANISM: Artificial Sequence
<220> FEATURE:
<223> OTHER INFORMATION: Synthetic oligonucleotide primer.

<400> SEQUENCE: 73
agtgctcctc agagggagtt g                                        21

<210> SEQ ID NO 74
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 74
tagactgact ctcaccacgc c                                        21

<210> SEQ ID NO 75
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 75
caccacttca ccctcctctc t                                        21

<210> SEQ ID NO 76
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 76
ccaagaagga agctgagttg c                                        21

<210> SEQ ID NO 77
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 77
actatggctg tgactcccca c                                        21

<210> SEQ ID NO 78
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 78
ggtaccagca aactgtgcct c                                        21

<210> SEQ ID NO 79
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 79
```
ggttctttgc ccactatggt c                                              21

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 80
tccagggctg taaaatcatc a                                              21

<210> SEQ ID NO 81
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 81
aggtgggttc agtgaatgaa a                                              21

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide primer.

<400> SEQUENCE: 82
tccatggctg gtcaatgatt                                                20

<210> SEQ ID NO 83
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 83
atggcgtcca cagtagcttt t                                              21

<210> SEQ ID NO 84
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 84
cctttcgatg tgactgtctc c                                              21

<210> SEQ ID NO 85
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 85
cgaagttgtg gacagtcgag a                                              21

<210> SEQ ID NO 86
<211> LENGTH: 21
<212> TYPE: DNA
<213> ORGANISM: Artificial Sequence

```
<220> FEATURE:
<223> OTHER INFORMATION: Synthetic oligonucleotide primer.

<400> SEQUENCE: 86
acactgctcc ctgagtcact g                                              21

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 87
ccactcccca ttgttgttgt t                                              21

<210> SEQ ID NO 88
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 88
gagaaggaag gagagagctg c                                              21

<210> SEQ ID NO 89
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 89
atgcgtggta gggcatttaa g                                              21

<210> SEQ ID NO 90
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 90
agtgatgtcc accctgttcc t                                              21

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 91
gtaatgcgtt ttcctctctg g                                              21

<210> SEQ ID NO 92
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 92
acaccatgaa ttgttgaagc c                                              21
```

<210> SEQ ID NO 93
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 93
gtgtgtggtc tcccataccc t                                    21

<210> SEQ ID NO 94
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 94
ctctaccacc tgagggcttt g                                    21

<210> SEQ ID NO 95
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 95
tccagggtgg acctcttatc a                                    21

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 96
gcacacaact ggttccgtta a                                    21

<210> SEQ ID NO 97
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 97
aagtcctgct cactcatgct g                                    21

<210> SEQ ID NO 98
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 98
aataaaagga aatggtgggg c                                    21

<210> SEQ ID NO 99
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 99
cattcctcag ccacagtgac a                                              21

<210> SEQ ID NO 100
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 100
ccctgctcta gcctttgttc t                                              21

<210> SEQ ID NO 101
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 101
cccacacatc tactggagga a                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 102
aaggagagag acaggcacac a                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 103
ccttgaagaa ccaacaggat g                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 104
tgtgacctcc tattccagtg c                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 105
taatgcatgg taggaccgaa t                                              21

<210> SEQ ID NO 106

```
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 106
tctcccacca actttcaatg a                                                    21

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 107 gagggatct ccctaaactg a                                                     21

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 108
ggaacattca tcctggttcc a                                                    21

<210> SEQ ID NO 109
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 109
aactggacaa gctctttggg a                                                    21

<210> SEQ ID NO 110
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 110
agtcctgttg cccaatacct g                                                    21

<210> SEQ ID NO 111
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 111
aaaaagcaga agcactgcaa g                                                    21

<210> SEQ ID NO 112
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 112
```
tctgaagaaa tgtacggcag c                                          21

<210> SEQ ID NO 113
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 113
atgaaggaaa ggtttcaccc a                                          21

<210> SEQ ID NO 114
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 114
ccaatcaaga ggaaagttgg a                                          21

<210> SEQ ID NO 115
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 115
tccttacaag gtgttgaggg c                                          21

<210> SEQ ID NO 116
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 116
ttggatttga cctcatgcac t                                          21

<210> SEQ ID NO 117
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 117
cagaggcagg gaaaagatgt c                                          21

<210> SEQ ID NO 118
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 118
ctggccatca gtaaatcaca tca                                        23

<210> SEQ ID NO 119
<211> LENGTH: 21
<212> TYPE: DNA

```
<213> ORGANISM: Artificial Sequence
<220> FEATURE:
<223> OTHER INFORMATION: Synthetic oligonucleotide primer.

<400> SEQUENCE: 119
attagccgaa gacagaggga a                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 120
tgttgaaaaa cacaagggca c                                              21

<210> SEQ ID NO 121
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 121
tattcccaga actttggcac a                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 122
cccgtttgac acagtacaag c                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 123
taaatgtgca actcaggcag g                                              21

<210> SEQ ID NO 124
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 124
cccatcgttt cagtgttctt ctt                                            23

<210> SEQ ID NO 125
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 125
tgcaagggaa ttttgaatga a                                              21
```

<210> SEQ ID NO 126
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 126
atagattgca gtttgttggc c                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 127
aggtgtcttt aagcctgagc c                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 128
tacacccttc atctcctggc t                                              21

<210> SEQ ID NO 129
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 129
tcaaaagggc atcagtgagg a                                              21

<210> SEQ ID NO 130
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 130
ctggcacagg atgtggtcat t                                              21

<210> SEQ ID NO 131
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 131
gagtccatgg tgaccacatt tt                                             22

<210> SEQ ID NO 132
<211> LENGTH: 21
<212> TYPE: DNA
<213> ORGANISM: Artificial Sequence
<220> FEATURE:

<223> OTHER INFORMATION: Synthetic oligonucleotide primer.

<400> SEQUENCE: 132
atcacagcca tcatggtcaa c                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 133
tgccacattt acagtcccag g                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 134
ccatttttct aatccatgcc c                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 135
tgcccctaca ccaaacatac c                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 136
cttctgtctg ttatggtcgg g                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 137
tgggggtcac attgattcat a                                              21

<210> SEQ ID NO 138
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 138
ggtgttggga gaagatgttg a                                              21

```
<210> SEQ ID NO 139
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 139
ccttggaaat cactcctttg c                                              21

<210> SEQ ID NO 140
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 140
tgatggtttc actgcatctg g                                              21

<210> SEQ ID NO 141
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 141
gcttctcata agccatgcac a                                              21

<210> SEQ ID NO 142
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 142
atgatgctct gggatgtgaa a                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 143
gtggtgatta attcttgggg g                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 144
ccttcagacc tgcaaaactc c                                              21

<210> SEQ ID NO 145
<211> LENGTH: 21
<212> TYPE: DNA
<213> ORGANISM: Artificial Sequence
<220> FEATURE:
<223> OTHER INFORMATION: Synthetic oligonucleotide primer.
```

```
<400> SEQUENCE: 145
ctatcagctc agcagcaagg a                                              21

<210> SEQ ID NO 146
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 146
gcaagggcca aataaccaag t                                              21

<210> SEQ ID NO 147
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 147
atcctttcat gttccttggc t                                              21

<210> SEQ ID NO 148
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 148
tggcttctgt ttctgagttg g                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 149
ccttaatctg cctccagctc a                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 150
taagttgggg tttggggaga t                                              21

<210> SEQ ID NO 151
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 151
cgcaccaaaa ttctatcatc c                                              21

<210> SEQ ID NO 152
<211> LENGTH: 21
```

<212> TYPE: DNA
<213> ORGANISM: Artificial Sequence
<220> FEATURE:
<223> OTHER INFORMATION: Synthetic oligonucleotide primer.

<400> SEQUENCE: 152
ctttcttgcc ttaatgctgg g                                    21

<210> SEQ ID NO 153
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 153
gaagaaggtg atctgggaac g                                    21

<210> SEQ ID NO 154
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 154
tcactctgtt ggttgtgtcg g                                    21

<210> SEQ ID NO 155
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 155
ggaccagacc agatggtagg a                                    21

<210> SEQ ID NO 156
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 156
tcaaacatcc tacagcgaag c                                    21

<210> SEQ ID NO 157
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 157
cctctccctc tcctctcatc a                                    21

<210> SEQ ID NO 158
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 158
tctcaagtgc atcaccagct c    21

<210> SEQ ID NO 159
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 159
taagcctacc acaccagcca c    21

<210> SEQ ID NO 160
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 160
agagcaccca gcaggtacag a    21

<210> SEQ ID NO 161
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 161
gggcaaggag aatgttgtag g    21

<210> SEQ ID NO 162
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 162
tgtcgttagt catctggtcc c    21

<210> SEQ ID NO 163
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 163
gacacacttc ctccatctgg c    21

<210> SEQ ID NO 164
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 164
gtctctgctc accccactca t    21

<210> SEQ ID NO 165
<211> LENGTH: 21
<212> TYPE: DNA
<213> ORGANISM: Artificial Sequence

```
<220> FEATURE:
<223> OTHER INFORMATION: Synthetic oligonucleotide primer.

<400> SEQUENCE: 165
ttgaggacaa aggtctcagg c                                              21

<210> SEQ ID NO 166
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 166
ttacctgtta gggctccaac g                                              21

<210> SEQ ID NO 167
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 167
ccagcggttt gatgagattg t                                              21

<210> SEQ ID NO 168
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 168
aaataaatcc acagccgagg t                                              21

<210> SEQ ID NO 169
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 169
caccatcaca tcctcaaaag c                                              21

<210> SEQ ID NO 170
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 170
cagaagaaag aggcagcagc a                                              21

<210> SEQ ID NO 171
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 171
ggacagggct gaacgaaata a                                              21
```

```
<210> SEQ ID NO 172
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 172
cacatgcaca tccatgctct c                                              21

<210> SEQ ID NO 173
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 173
agctggtgat ggacacatgg t                                              21

<210> SEQ ID NO 174
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 174
ttaacccacc tgaacctgtc c                                              21

<210> SEQ ID NO 175
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 175
agaactttcc tcctcctccc t                                              21

<210> SEQ ID NO 176
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 176
tgtgagggaa atctaccttc g                                              21

<210> SEQ ID NO 177
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 177
gatctcaggg tcttctctgg g                                              21

<210> SEQ ID NO 178
<211> LENGTH: 23
<212> TYPE: DNA
<213> ORGANISM: Artificial Sequence
<220> FEATURE:
<223> OTHER INFORMATION: Synthetic oligonucleotide primer.
```

<400> SEQUENCE: 178
tgtttattta tgtggcaggt tgg                                            23

<210> SEQ ID NO 179
<211> LENGTH: 24
<212> TYPE: DNA
<213> ORGANISM: Artificial Sequence
<220> FEATURE:
<223> OTHER INFORMATION: Synthetic oligonucleotide primer.

<400> SEQUENCE: 179
ggggaaaaat cagaaaacta cact                                           24

<210> SEQ ID NO 180
<211> LENGTH: 24
<212> TYPE: DNA
<213> ORGANISM: Artificial Sequence
<220> FEATURE:
<223> OTHER INFORMATION: Synthetic oligonucleotide primer.

<400> SEQUENCE: 180
gaacctgcct ctgtctttga tacc                                           24

<210> SEQ ID NO 181
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 181
tgtgcatcag ctatccaaca a                                              21

<210> SEQ ID NO 182
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 182
ccacgtccag gctgtttatt t                                              21

<210> SEQ ID NO 183
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 183
ccaaggcact gtttttttgaa g                                             21

<210> SEQ ID NO 184
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 184
tattagggtg gtgggtcttc c                                              21

<210> SEQ ID NO 185

```
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 185
caagctgaca gaatggagag g                                           21

<210> SEQ ID NO 186
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 186
gattatgcag taaccacaag g                                           21

<210> SEQ ID NO 187
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 187
tggaaactct gggacactca a                                           21

<210> SEQ ID NO 188
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 188
aatgttacct ttgaggggtg g                                           21

<210> SEQ ID NO 189
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 189
gctccaggtc ttccctctct c                                           21

<210> SEQ ID NO 190
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 190
gtccagtctg caacatccaa c                                           21

<210> SEQ ID NO 191
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 191
```

-continued

```
tggttcccct cttgattcag c                                              21

<210> SEQ ID NO 192
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 192
gttgctggga gtcctgtgtc t                                              21

<210> SEQ ID NO 193
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 193
tacaacatag aggggaggca c                                              21

<210> SEQ ID NO 194
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 194
agcacaaagt tgctcacagg a                                              21

<210> SEQ ID NO 195
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 195
acctgtccta tccacccatt t                                              21

<210> SEQ ID NO 196
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 196
aggagtagca ggacacccgt t                                              21

<210> SEQ ID NO 197
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 197
gccccaccac tttctctttc t                                              21

<210> SEQ ID NO 198
<211> LENGTH: 21
<212> TYPE: DNA
```

<213> ORGANISM: Artificial Sequence
<220> FEATURE:
<223> OTHER INFORMATION: Synthetic oligonucleotide primer.

<400> SEQUENCE: 198
acaagaaggt tttgaggctc c                                    21

<210> SEQ ID NO 199
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 199
aggtttgcgg gagtcatatc t                                    21

<210> SEQ ID NO 200
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 200
gggagagttg gtcccctttt a                                    21

<210> SEQ ID NO 201
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 201
agctgggtct gaatccaggt a                                    21

<210> SEQ ID NO 202
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 202
ctctggtctc ccatctgctt t                                    21

<210> SEQ ID NO 203
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 203
gttgaaagaa caaggcagct c                                    21

<210> SEQ ID NO 204
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 204
agtgggagag ggatagtggc t                                    21

<210> SEQ ID NO 205
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 205
gcagtacctg caacttggtg a                                          21

<210> SEQ ID NO 206
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 206
aatgcacaca ggtggacaga t                                          21

<210> SEQ ID NO 207
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 207
ctccaactgc attccaacaa g                                          21

<210> SEQ ID NO 208
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 208
aacttattcc ttggaccgct g                                          21

<210> SEQ ID NO 209
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 209
taccaagagg ggagacagag g                                          21

<210> SEQ ID NO 210
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 210
gcaccaaagt ctcctccctc t                                          21

<210> SEQ ID NO 211
<211> LENGTH: 21
<212> TYPE: DNA
<213> ORGANISM: Artificial Sequence
<220> FEATURE:

<223> OTHER INFORMATION: Synthetic oligonucleotide primer.

<400> SEQUENCE: 211
ggtcaactcc agggacact a                                           21

<210> SEQ ID NO 212
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 212
ggtggtgaca gtaaacagcc c                                          21

<210> SEQ ID NO 213
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 213
ccccattcat gctctctctt t                                          21

<210> SEQ ID NO 214
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 214
tgttgcttca gcatgtcaag a                                          21

<210> SEQ ID NO 215
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 215
agggtttagc acttgtggag g                                          21

<210> SEQ ID NO 216
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 216
agatgttaga tgttggggtg g                                          21

<210> SEQ ID NO 217
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 217
tccacctctg tctcccttct c                                          21

```
<210> SEQ ID NO 218
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 218
tgggtctctg tgagtggaag g                                             21

<210> SEQ ID NO 219
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 219
gtccctaaag ccttgttcct g                                             21

<210> SEQ ID NO 220
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 220
tgaccttggc cttccttagt t                                             21

<210> SEQ ID NO 221
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 221
atacctacca gccaggctca g                                             21

<210> SEQ ID NO 222
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 222
aatctttaga ccccctcacc c                                             21

<210> SEQ ID NO 223
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 223
ttaatacaaa ggtcccccag g                                             21

<210> SEQ ID NO 224
<211> LENGTH: 21
<212> TYPE: DNA
<213> ORGANISM: Artificial Sequence
<220> FEATURE:
<223> OTHER INFORMATION: Synthetic oligonucleotide primer.
```

-continued

<400> SEQUENCE: 224
atggggaaga gtggggtcta t                                              21

<210> SEQ ID NO 225
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 225
gtcttgttcc acagcaccat c                                              21

<210> SEQ ID NO 226
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 226
tatgctgcca aagagaaccc                                                21

<210> SEQ ID NO 227
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 227
gtctgccaag ggaaacatca t                                              21

<210> SEQ ID NO 228
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 228
cctgttgttc ctcccagtct t                                              21

<210> SEQ ID NO 229
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 229
ccagcaccag ggagtagttt g                                              21

<210> SEQ ID NO 230
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 230
gagtgcaggg gctgatctct a                                              21

<210> SEQ ID NO 231
<211> LENGTH: 21

```
<212> TYPE: DNA
<213> ORGANISM: Artificial Sequence
<220> FEATURE:
<223> OTHER INFORMATION: Synthetic oligonucleotide primer.

<400> SEQUENCE: 231
ctctgactga ctggcgagat g                                           21

<210> SEQ ID NO 232
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 232
ccctggagaa gtgggagtgt a                                           21

<210> SEQ ID NO 233
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 233
cccaaacacc aggtactagg c                                           21

<210> SEQ ID NO 234
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 234
cggtacgaag aaaaccagga g                                           21

<210> SEQ ID NO 235
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 235
tctcacccct cttccactgt t                                           21

<210> SEQ ID NO 236
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 236
ctgcaggtga gactcagcaa t                                           21

<210> SEQ ID NO 237
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 237
```
gaaagggaag caggaaagag g                                              21

<210> SEQ ID NO 238
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 238
cccttcctat cttctcccac c                                              21

<210> SEQ ID NO 239
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 239
aatgagcatg gagaatcgtg t                                              21

<210> SEQ ID NO 240
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 240
gaatgggact cctgagagct g                                              21

<210> SEQ ID NO 241
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 241
taacacattc aggatggacg c                                              21

<210> SEQ ID NO 242
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 242
agagcactga ccctccttag g                                              21

<210> SEQ ID NO 243
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 243
ccactcacga agatgtcgaa g                                              21

<210> SEQ ID NO 244
<211> LENGTH: 21
<212> TYPE: DNA
<213> ORGANISM: Artificial Sequence

```
<220> FEATURE:
<223> OTHER INFORMATION: Synthetic oligonucleotide primer.

<400> SEQUENCE: 244
ccttaagagg cagccagact g                                        21

<210> SEQ ID NO 245
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 245
cacagcctga ctggacaaaa g                                        21

<210> SEQ ID NO 246
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 246
ctgggagagg cagagattca t                                        21

<210> SEQ ID NO 247
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 247
ctctttcctg attcgaggtg g                                        21

<210> SEQ ID NO 248
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 248
atacctacca gccaggctca g                                        21

<210> SEQ ID NO 249
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 249
tgaccttggc cttccttagt t                                        21

<210> SEQ ID NO 250
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 250
tgttcctggg cacattttta a                                        21
```

<210> SEQ ID NO 251
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 251
ccaaatctga ggaaagggtg a                                            21

<210> SEQ ID NO 252
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 252
catccacctc tgtctccctt c                                            21

<210> SEQ ID NO 253
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 253
agatgttggg gtggtagaag g                                            21

<210> SEQ ID NO 254
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 254
ggtggagaca gggtttagca c                                            21

<210> SEQ ID NO 255
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 255
atctaccctg acccatctgg t                                            21

<210> SEQ ID NO 256
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 256
tccaacttac aggccctctt g                                            21

<210> SEQ ID NO 257
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 257
tttgctcatt aacccatcag g					21

<210> SEQ ID NO 258
<211> LENGTH: 22
<212> TYPE: DNA
<213> ORGANISM: Artificial Sequence
<220> FEATURE:
<223> OTHER INFORMATION: Synthetic oligonucleotide primer.

<400> SEQUENCE: 258
aggggagact ccctatttg tc					22

<210> SEQ ID NO 259
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 259
acctacttca ccagccagct t					21

<210> SEQ ID NO 260
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 260
attaccctca agagccccag t					21

<210> SEQ ID NO 261
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 261
agggttaggg tgaggatcag g					21

<210> SEQ ID NO 262
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 262
ccaactgcat tccaacaagt c					21

<210> SEQ ID NO 263
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 263
aatgcacaca ggtggacaga t					21

<210> SEQ ID NO 264

```
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 264
gctcagcctg acagctcagt a                                              21

<210> SEQ ID NO 265
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 265
gctggcaaga gagcacaaga t                                              21

<210> SEQ ID NO 266
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 266
gctgttgaaa gaacaaggca g                                              21

<210> SEQ ID NO 267
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 267
ctggtctccc atctgctttc t                                              21

<210> SEQ ID NO 268
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 268
agctgggtct gaatccaggt a                                              21

<210> SEQ ID NO 269
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 269
gtggggatag aactgctagg g                                              21

<210> SEQ ID NO 270
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 270
``` aacccccaatg aagagagacc a                                          21

<210> SEQ ID NO 271
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 271
gttcctcaag agtggctttg g                                           21

<210> SEQ ID NO 272
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 272
ccaacatgag ttcccttcca t                                           21

<210> SEQ ID NO 273
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 273
cacctgtcct atccacccat t                                           21

<210> SEQ ID NO 274
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 274
agaggggagg cacaggactt a                                           21

<210> SEQ ID NO 275
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 275
gctgggagtc ctgtgtctca t                                           21

<210> SEQ ID NO 276
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 276
tggttccctt cttgattcag c                                           21

<210> SEQ ID NO 277
<211> LENGTH: 21
<212> TYPE: DNA

<213> ORGANISM: Artificial Sequence
<220> FEATURE:
<223> OTHER INFORMATION: Synthetic oligonucleotide primer.

<400> SEQUENCE: 277
ctggacatgc tgaagaggtg a                                              21

<210> SEQ ID NO 278
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 278
ctctcctccc ccaactcaac t                                              21

<210> SEQ ID NO 279
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 279
ctcctaagac aggcctcaac c                                              21

<210> SEQ ID NO 280
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 280
atgttacctt tgaggggtgg t                                              21

<210> SEQ ID NO 281
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 281
gaagaaggtg gtggagagga a                                              21

<210> SEQ ID NO 282
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 282
cacctcaaga acaggaactg g                                              21

<210> SEQ ID NO 283
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 283
tattagggtg gtgggtcttc c                                              21

-continued

<210> SEQ ID NO 284
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 284
cctctccaag gcactgtttt t                                         21

<210> SEQ ID NO 285
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 285
gcaccatgct tttttttcaa a                                         21

<210> SEQ ID NO 286
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 286
tcaaagggca ctcatttcat g                                         21

<210> SEQ ID NO 287
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 287
aacctgcctc tgtctttgat acc                                       23

<210> SEQ ID NO 288
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 288
gaggggGaaa aatcagaaaa c                                         21

<210> SEQ ID NO 289
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 289
attgagggta gaggaggttg g                                         21

<210> SEQ ID NO 290
<211> LENGTH: 21
<212> TYPE: DNA
<213> ORGANISM: Artificial Sequence
<220> FEATURE:

<223> OTHER INFORMATION: Synthetic oligonucleotide primer.

<400> SEQUENCE: 290
cgaatggcta actcccacaa a                                           21

<210> SEQ ID NO 291
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 291
gggacctcat gttcttgatg tta                                         23

<210> SEQ ID NO 292
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 292
aatagccttg ctagtgggtg c                                           21

<210> SEQ ID NO 293
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 293
catggggagg tacaactttt g                                           21

<210> SEQ ID NO 294
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 294
ccccagtaac catgcagaga g                                           21

<210> SEQ ID NO 295
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 295
ggcattttca aaattaacag acg                                         23

<210> SEQ ID NO 296
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 296
ggcaacatct aaaacttcag cct                                         23

```
<210> SEQ ID NO 297
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 297
ttgcttgcag ccttgaagta t                                          21

<210> SEQ ID NO 298
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 298
aggtgtcttt aagcctgagc c                                          21

<210> SEQ ID NO 299
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 299
aaaatcctgt cctggctcat c                                          21

<210> SEQ ID NO 300
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 300
tacacccttc atctcctggc t                                          21

<210> SEQ ID NO 301
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 301
aagatttggc acttgaaagg a                                          21

<210> SEQ ID NO 302
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 302
cacgaacaca cacacacacc c                                          21

<210> SEQ ID NO 303
<211> LENGTH: 24
<212> TYPE: DNA
<213> ORGANISM: Artificial Sequence
<220> FEATURE:
<223> OTHER INFORMATION: Synthetic oligonucleotide primer.
```

```
<400> SEQUENCE: 303
catcacttca aacacaagag catt                                          24

<210> SEQ ID NO 304
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 304
tattagccga agacagaggg a                                             21

<210> SEQ ID NO 305
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 305
cctgattgga catttcccat a                                             21

<210> SEQ ID NO 306
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 306
acaagctgta aagctctgcc c                                             21

<210> SEQ ID NO 307
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 307
taaatgtgca actcaggcag g                                             21

<210> SEQ ID NO 308
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 308
gtgcttcacc acttgggttt t                                             21

<210> SEQ ID NO 309
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 309
gacccccatt taactttcag c                                             21

<210> SEQ ID NO 310
<211> LENGTH: 21
```

<212> TYPE: DNA
<213> ORGANISM: Artificial Sequence
<220> FEATURE:
<223> OTHER INFORMATION: Synthetic oligonucleotide primer.

<400> SEQUENCE: 310
ggctgaggct ttattttgga g                                    21

<210> SEQ ID NO 311
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 311
gcggttttca ctgacgcagt a                                    21

<210> SEQ ID NO 312
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 312
cacctttgtg gaactgccta c                                    21

<210> SEQ ID NO 313
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 313
aaaccttcgc atttcatcct c                                    21

<210> SEQ ID NO 314
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 314
gcctttctgt ggcttttgtt t                                    21

<210> SEQ ID NO 315
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 315
tgttctacca ggacgccacg g                                    21

<210> SEQ ID NO 316
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 316
acgcaaggac ctgacattaa a                                              21

<210> SEQ ID NO 317
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 317
tggtaactga aaatgggtgg a                                              21

<210> SEQ ID NO 318
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 318
ttaattgctt ccaccaaccc t                                              21

<210> SEQ ID NO 319
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 319
agatccctgg tctttgttcc c                                              21

<210> SEQ ID NO 320
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 320
cctggaaagc agagaactag g                                              21

<210> SEQ ID NO 321
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 321
cattttggca tgtatgtggt g                                              21

<210> SEQ ID NO 322
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 322
cccctctcct tagaaaatcc c                                              21

<210> SEQ ID NO 323
<211> LENGTH: 21
<212> TYPE: DNA
<213> ORGANISM: Artificial Sequence

```
<220> FEATURE:
<223> OTHER INFORMATION: Synthetic oligonucleotide primer.

<400> SEQUENCE: 323
gcgaatggga tacatcaaag a                                        21

<210> SEQ ID NO 324
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 324
cagagcctaa agaacccacc a                                        21

<210> SEQ ID NO 325
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 325
tgcacacttt aactgcacca t                                        21

<210> SEQ ID NO 326
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 326
cagtaagcaa actgccctca t                                        21

<210> SEQ ID NO 327
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 327
agccaaaggt tccaggacaa t                                        21

<210> SEQ ID NO 328
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 328
ccagcacctc accctgacta t                                        21

<210> SEQ ID NO 329
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 329
tgtgatgcta cccactccac t                                        21
```

```
<210> SEQ ID NO 330
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 330
ggtctcctcg gttactccca t                                              21

<210> SEQ ID NO 331
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 331
gcaagtgcaa ggaaggaaag a                                              21

<210> SEQ ID NO 332
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 332
ggaggcctgc tgaacttctt t                                              21

<210> SEQ ID NO 333
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 333
gcacataagg ctcacaggaa a                                              21

<210> SEQ ID NO 334
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 334
atagtgtggg taggatggtg c                                              21

<210> SEQ ID NO 335
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 335
aaaagcaaga gcagagaagg c                                              21

<210> SEQ ID NO 336
<211> LENGTH: 21
<212> TYPE: DNA
<213> ORGANISM: Artificial Sequence
<220> FEATURE:
<223> OTHER INFORMATION: Synthetic oligonucleotide primer.
```

```
<400> SEQUENCE: 336
aggcgctgca actacaaaga t                                              21

<210> SEQ ID NO 337
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 337
ctgaccttca cagacatccc c                                              21

<210> SEQ ID NO 338
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 338
ggactacaag ggacgagagg c                                              21

<210> SEQ ID NO 339
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 339
ctgggaggat cacctgacag a                                              21

<210> SEQ ID NO 340
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 340
caccaccaag acaagcctaa a                                              21

<210> SEQ ID NO 341
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 341
ccataaatga agcctcctgc c                                              21

<210> SEQ ID NO 342
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 342
cttggaaaag ccaatggaaa t                                              21

<210> SEQ ID NO 343
```

```
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 343
aaggtcctag cccttagcag a                                              21

<210> SEQ ID NO 344
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 344
acacacacat ctgcaactcg g                                              21

<210> SEQ ID NO 345
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 345
ccgtttcagc aaaactgaga a                                              21

<210> SEQ ID NO 346
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 346
agtgtcttag tcaccccctg c                                              21

<210> SEQ ID NO 347
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 347
cccaggatgt ggagatgaaa g                                              21

<210> SEQ ID NO 348
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 348
ggtgggggac taggagtgaa a                                              21

<210> SEQ ID NO 349
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 349
```
acgaagtcag tttggtggtg g                                              21

<210> SEQ ID NO 350
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 350
cacccacact tttctgcctc t                                              21

<210> SEQ ID NO 351
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 351
ggtgagccct tatcctcagt t                                              21

<210> SEQ ID NO 352
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 352
ctccagccct ggtcacaata t                                              21

<210> SEQ ID NO 353
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 353
cgtgtccact tcaaggtgaa t                                              21

<210> SEQ ID NO 354
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 354
caccaggctt gtcatttacc a                                              21

<210> SEQ ID NO 355
<211> LENGTH: 21
<212> TYPE: DNA
<213> ORGANISM: Artificial Sequence
<220> FEATURE:
<223> OTHER INFORMATION: Synthetic oligonucleotide primer.

<400> SEQUENCE: 355
gatgcctcat ctttcctcac t                                              21

```
<210> SEQ ID NO 356
<211> LENGTH: 23
<212> TYPE: DNA
<213> ORGANISM: Artificial Sequence
<220> FEATURE:
<223> OTHER INFORMATION: Synthetic oligonucleotide primer.

<400> SEQUENCE: 356
gtgaactcac tcacttgggt agc                                              23

<210> SEQ ID NO 357
<211> LENGTH: 6
<212> TYPE: DNA
<213> ORGANISM: Artificial Sequence
<220> FEATURE:
<223> OTHER INFORMATION: An exemplary oligonucleotide consisting
      exclusively of purines.

<400> SEQUENCE: 357 gaggag                                                                  6

<210> SEQ ID NO 358
<211> LENGTH: 6
<212> TYPE: DNA
<213> ORGANISM: Artificial Sequence
<220> FEATURE:
<223> OTHER INFORMATION: The reverse complement of SEQ ID NO: 357.

<400> SEQUENCE: 358 ctcctc                                                                  6

<210> SEQ ID NO 359
<211> LENGTH: 6
<212> TYPE: DNA
<213> ORGANISM: Artificial Sequence
<220> FEATURE:
<223> OTHER INFORMATION: An exemplary telomere repeat.

<400> SEQUENCE: 359 ttaggg                                                                  6

<210> SEQ ID NO 360
<211> LENGTH: 5
<212> TYPE: DNA
<213> ORGANISM: Artificial Sequence
<220> FEATURE:
<223> OTHER INFORMATION: An exemplary five-base repeating unit of
      satellites II and III.

<400> SEQUENCE: 360 attcc                                                                   5
```

METHOD FOR PRODUCING NUCLEIC ACID PROBES

CROSS-REFERENCE TO RELATED APPLICATIONS

This application is a divisional of U.S. application Ser. No. 11/849,060 filed Aug. 31, 2007, which claims the benefit of U.S. Provisional Application No. 60/841,896 filed Sep. 1, 2006 and U.S. Provisional Application No. 60/892,571 filed Mar. 2, 2007, all of which are herein incorporated by reference in their entireties.

FIELD

This disclosure relates to the field of molecular detection of nucleic acid target sequences (e.g., genomic DNA or RNA). More specifically, this disclosure relates to nucleic acid probes that form one or more detectable networks on the target sequence, methods for probe production, and methods of their use. In some embodiments, the disclosed probes are substantially free of repetitive nucleic acid sequence.

BACKGROUND

Molecular cytogenetic techniques, such as fluorescence in situ hybridization (FISH), chromogenic in situ hybridization (CISH) and silver in situ hybridization (SISH), combine visual evaluation of chromosomes (karyotypic analysis) with molecular techniques. Molecular cytogenetics methods are based on hybridization of a nucleic acid probe to its complementary nucleic acid within a cell. A probe for a specific chromosomal region will recognize and hybridize to its complementary sequence on a metaphase chromosome or within an interphase nucleus (for example in a tissue sample). Probes have been developed for a variety of diagnostic and research purposes. For example, certain probes produce a chromosome banding pattern that mimics traditional cytogenetic staining procedures and permits identification of individual chromosomes for karyotypic analysis. Other probes are derived from a single chromosome and when labeled can be used as "chromosome paints" to identify specific chromosomes within a cell. Yet other probes identify particular chromosome structures, such as the centromeres or telomeres of chromosomes.

Unique sequence probes hybridize to single copy DNA sequences in a specific chromosomal region or gene. These are the probes used to identify the chromosomal critical region or gene associated with a syndrome or condition of interest. On metaphase chromosomes, such probes hybridize to each chromatid, usually giving two small, discrete signals per chromosome.

Hybridization of unique sequence probes has made possible detection of chromosomal abnormalities associated with numerous diseases and syndromes, including constitutive genetic anomalies, such as microdeletion syndromes, chromosome translocations, gene amplification and aneuploidy syndromes, neoplastic diseases as well as pathogen infections. Most commonly these techniques are applied to standard cytogenetic preparations on microscope slides. In addition, these procedures can be used on slides of formalin-fixed tissue, blood or bone marrow smears, and directly fixed cells or other nuclear isolates.

For example, these techniques are frequently used to characterize tumor cells for both diagnosis and prognosis of cancer. Numerous chromosomal abnormalities have been associated with the development of cancer (for example, aneuploidies such as trisomy 8 associated with certain myeloid disorders; translocations such as the BCR/ABL rearrangement in chronic myelogenous leukemia; and amplifications of specific nucleic acid sequences associated with neoplastic transformation). Molecular techniques can augment standard cytogenetic testing in the detection and characterization of such acquired chromosomal anomalies. For example, FISH has been used to look for early relapse and residual disease in nondividing cells. Immunocytochemical detection of cancer cells and FISH techniques have been combined to study chromosomal abnormalities in defined cell populations.

The present disclosure provides improved probes and methods for producing such probes for use in diagnostic and research applications of in situ hybridization.

SUMMARY

The present disclosure concerns nucleic acid probes and methods for their use and production. The probes correspond to a target nucleic acid sequence (e.g., a genomic or RNA target nucleic acid sequence) and are suitable for molecular analysis of such target(s), for example, in in situ hybridization methods, such as FISH, CISH and SISH. In particular examples, the disclosed probes offer increased sensitivity and specificity and reduced background as compared to conventional probes.

Probes are provided by the present application. In one example, a nucleic acid probe includes a plurality of nucleic acid molecules. Substantially all of the plurality of nucleic acid molecules each include at least a first binding region and a second binding region, wherein the first binding region and the second binding region are contiguous and complementary to non-contiguous portions and unique sequences of a target nucleic acid molecule. Thus, the binding regions can be positioned in the plurality of nucleic acid molecules such that the order and/or orientation of the binding regions is different from the order and orientation of the binding regions in the target sequence. Therefore, the plurality of nucleic acid molecules are referred to herein as fragmented, permuted, concatenated (FPC) nucleic acid molecules. In particular examples, the binding regions are substantially free of undesired sequence, such as sequences that result in increased non-specific binding of a nucleic acid probe to a target nucleic acid sequence (e.g., repetitive nucleic acid sequences found in mammalian genomic target nucleic acid sequences, sequences encoding conserved domains in RNA target sequences, or homologous sequences in viral target genomic nucleic acid sequences). The plurality of nucleic acid molecules can be labeled, thus producing a labeled probe. In one example, the plurality of nucleic acid molecules is labeled using nick translation, thus fragmenting the plurality of nucleic acid molecules, wherein the fragmented molecules can be used as a probe.

In some examples, the probe includes a heterogeneous plurality of nucleic acid molecules. Substantially all of the heterogeneous plurality of nucleic acid molecules each include at least first binding region having a first nucleotide sequence, and a second binding region having a second nucleotide sequence. The first binding region and the second binding region are contiguous and complementary to non-contiguous portions and unique nucleotide sequences of the target nucleic acid molecule. The first nucleotide sequence and the second nucleotide sequence in each of the plurality of nucleic acid molecules can differ from the first nucleotide sequence and the second nucleotide sequence in others of the plurality of nucleic acid molecules.

Also disclosed are methods for producing the probes of the present disclosure, as well as probes produced by the method. In one example, probes are produced by a method that includes ligating at least a first binding region and a second binding region, thereby producing a plurality of nucleic acid molecules. Substantially all of the plurality of nucleic acid molecules each include a contiguous at least first binding region and second binding region, wherein the contiguous at least first binding region and second binding region are complementary to non-contiguous portions and unique sequences of the target nucleic acid molecule. In particular examples, binding regions are substantially free of undesired sequence present in the target sequence, such as sequences that result in increased non-specific binding of a nucleic acid probe to a target nucleic acid sequence (e.g., repetitive nucleic acid sequences found in mammalian genomic target nucleic acid sequences, sequences encoding conserved domains in RNA target sequences, or homologous sequences in viral target genomic nucleic acid sequences). The resulting plurality of nucleic acid molecules form the probe. The method can further include amplifying the plurality of nucleic acid molecules to produce a plurality of nucleic acid molecule amplicons to form the probe. The method can also include labeling the plurality of nucleic acid molecules or amplicons therefrom to produce a labeled probe.

In particular examples, the binding regions are generated by one or more of the following: isolating the binding regions from the target nucleic acid sequence; obtaining binding regions from the target nucleic acid sequence by subtractive hybridization; or amplifying binding regions from the target nucleic acid sequence. For example, binding regions can be isolated or amplified from a target nucleic acid sequence present in a vector.

Methods of using the disclosed probes include, for example, detecting (and in some examples quantifying) a target nucleic acid sequence. For example, the method can include contacting the disclosed probes with a sample containing nucleic acid molecules (e.g., DNA or RNA) under conditions sufficient to permit hybridization between the nucleic acid molecules in the sample and the plurality of nucleic acid molecules of the probe. Resulting hybridization is detected, wherein the presence of hybridization indicates the presence of the target nucleic acid sequence.

Kits including the probes and/or starting materials and/or reagents for producing the probes are also disclosed.

The foregoing and other objects and features of the disclosure will become more apparent from the following detailed description.

BRIEF DESCRIPTION OF THE DRAWINGS

FIG. 1B is a schematic illustration showing how FPC nucleic acid molecules can be produced from binding regions that are substantially or entirely free of undesired nucleic acid sequences (e.g., repetitive nucleic acid sequences found in mammalian genomic target nucleic acid sequences, sequences encoding conserved domains in RNA target sequences, or homologous sequences in viral target genomic nucleic acid sequences), and then amplified and labeled, to produce a probe.

FIG. 4 is a schematic illustration showing production of FPC nucleic acids molecules by attaching duplexed oligonucleotides that include a fixed nucleotide sequence to double-stranded binding regions prior to ligation.

FIG. 5 is a schematic illustration showing amplification of a template FPC nucleic acid molecule using a fixed (all purine) primer.

FIG. 7 is a digital image of an agarose gel image showing the size distribution of a FPC nucleic acid probe for human genomic HER2 (lane A) and fragments of same produced by 100° C. heat treatment for 5 (lane 2), 30 (lane 3) or 60 (lane 4) minutes.

FIG. 8A-D are digital images showing formalin-fixed, paraffin-embedded HER2-positive BT474 xenograph sections (left panels) and HER2-negative MCF7 xenograph sections (right panels) tissues stained with FPC nucleic acid probe for human genomic HER2 (panel A) and fragments of same produced by 100° C. heat treatment for 5 (panel B), 30 (panel C) or 60 (panel D) minutes.

FIGS. 9A and B are digital images showing HPV16-positive Caski cell xenograph sections (A) and HPV16-negative C33A cell xenograph sections (B) stained with a FPC nucleic acid probe for HPV16 genomic DNA.

FIG. 10 shows images of formalin-fixed, paraffin-embedded human kidney tissue sections from four BK virus-infected individuals ("Positive Kidney") and two individuals not infected with the BK virus ("Negative Kidney"), each of which was stained with a permuted BK virus genomic DNA probe. The BK virus probe concentration, magnification, and detection method are shown to the far left of the respective images.

SEQUENCE LISTING

Figure 1A:
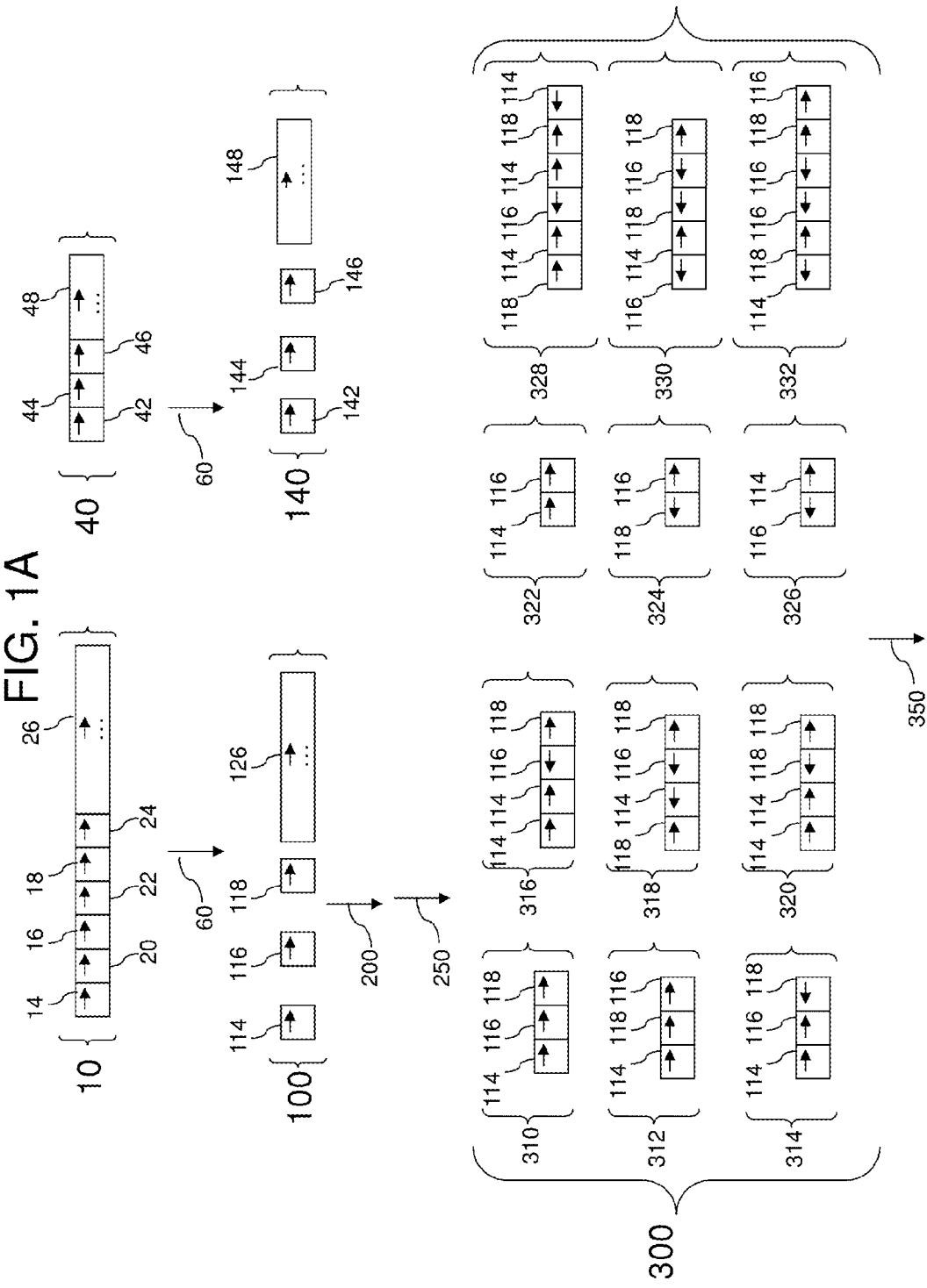
FIG. 1A is a schematic illustration showing how probe 300 can be generated from a target nucleic acid sequence 10.

The nucleic and amino acid sequences listed in the sequence listing to accompany this application will be shown using standard letter abbreviations for nucleotide bases as defined in 37 C.F.R. 1.822. Only one strand of each nucleic acid sequence will be shown, but the complementary strand is understood as included by any reference to the displayed strand (unless the context requires otherwise). All sequence database accession numbers referenced herein are understood to refer to the version of the sequence identified by that accession number as it was available on Sep. 1, 2006.

SEQ ID NOS: 1-356 are primers used to amplify 178 binding regions specific for the region of the human genome containing the HER2 gene, wherein SEQ ID NOS: 1-178 are forward primers and SEQ ID NOS: 179-356 are the paired reverse primers, respectively (see Table 1).

SEQ ID NO: 357 is an exemplary oligonucleotide consisting exclusively of purines.

SEQ ID NO: 358 is the reverse complement of SEQ ID NO: 357.

SEQ ID NO: 359 is an exemplary tandem repeat sequence found in telomeres.

SEQ ID NO: 360 is an exemplary five-base repeating unit sequence found in satellite II and III repetitive nucleic acid sequences.

DETAILED DESCRIPTION

Introduction

Production of probes corresponding to selected target nucleic acid sequences (e.g., genomic target nucleic acid sequences or RNA target nucleic acid sequences) for molecular analysis can be complicated by the presence of undesired sequences that can potentially increase the amount of background signal when present in a probe. Examples of undesired sequences include, but are not limited to: interspersed repetitive nucleic acid elements present throughout eukaryotic (e.g., human) genomes, conserved domains encoded by RNA sequences, as well as homologous sequences present in a viral genome. For example, if the target nucleic acid sequence is an HPV-1 sequence, undesired sequences may include homologous sequences found in other HPV genomic sequences (e.g. sequences specific for the HPV family of viruses), but are not specific for HPV-1. In another example, the target sequence is an RNA sequence, and undesired sequences may include conserved domains present in that RNA sequence, such sequences found in other non-target RNA sequences and are thus not specific for the target RNA sequence. The selection of probes typically attempts to balance the strength of a target specific signal against the level of non-specific background. When selecting a probe corresponding to a target, signal is generally maximized by increasing the size of the probe. However, as the size of a probe (e.g., for genomic target nucleic acid sequences) increases so does the amount of undesired (e.g., repetitive) nucleic acid sequence included in the probe. When the probe is labeled (either directly with a detectable moiety, such as a fluorophore, or indirectly with a moiety such as a hapten, which can indirectly be detected based on binding and detection of additional components), the undesired (e.g., repetitive) nucleic acid sequence elements are labeled along with the target-specific elements within the target sequence. During in situ hybridization, binding of the labeled undesired (e.g., repetitive) nucleic acid sequences results in a dispersed background signal, which can confound interpretation, for example when numerical or quantitative data (such as copy number of a sequence) is desired.

Reduction of background due to hybridization of labeled repetitive or other undesired nucleic acid sequences in the probe has typically been accomplished by adding blocking DNA (e.g., unlabeled repetitive DNA, such as $C_o t$-1™ DNA) to the hybridization reaction.

The present disclosure provides an approach to reducing or eliminating background signal due to the presence of repetitive or other undesired nucleic acid sequences in a probe. Some exemplary probes disclosed herein are substantially or entirely free of repetitive or other undesired nucleic acid sequences, such as probes that are repeat-free or substantially repeat-free.

Nucleic acid probes are provided by the present disclosure. In particular examples, the probes include a plurality of nucleic acid molecules, referred to herein as fragmented, permuted, concatenated (FPC) nucleic acid molecules. The FPC nucleic acid molecules include portions or segments of a selected target nucleic acid sequence (e.g., genomic or RNA target nucleic acid sequence), and thus are said to be fragmented. The segments of the target nucleic acid sequence are referred to herein as binding regions, which can be free or substantially free of undesired (e.g., repetitive, conserved domain, or homologous) nucleic acid sequences. The FPC nucleic acid molecules are said to be permuted because the order or orientation of the binding regions can be different in a FPC nucleic acid molecule relative to the corresponding target nucleic acid sequence (e.g., genomic or RNA target nucleic acid sequence). The FPC nucleic acid molecules are said to be concatenated because FPC nucleic acid molecules include a plurality of ligated binding regions, thereby forming a linear nucleic acid molecule of ligated binding regions.

Substantially all of the plurality of nucleic acid molecules, or FPC nucleic acid molecules, in a probe each include at least first binding region and a second binding region, wherein the first binding region and the second binding region are contiguous and complementary to non-contiguous portions and unique sequences of a target nucleic acid molecule. For example, the probe can include a heterogeneous plurality of nucleic acid molecules, substantially all of which each include at least first binding region having a first nucleotide sequence and a second binding region having a second nucleotide sequence, wherein the first binding region and the second binding region are contiguous and complementary to non-contiguous portions and unique nucleotide sequences of a target nucleic acid molecule, and wherein the first nucleotide sequence and the second nucleotide sequence in each of the plurality of nucleic acid molecules can differ from first nucleotide sequence and the second nucleotide sequence in others of the plurality of nucleic acid molecules. Therefore, the FPC nucleic acid molecules can include multiple binding regions in a different order, orientation, or both, relative to the target nucleic acid sequence. For example, the plurality of nucleic acid molecules can include at least five or at least 10 binding regions contiguous with the first and second binding regions, wherein the at least five or at least 10 binding regions are complementary to non-contiguous portions and unique sequences of the target nucleic acid molecule. For example, a FPC nucleic acid molecule can include a small number of different binding regions, such as two, three, five, ten, or twenty. In other instances, the number of different binding regions corresponding to a target sequence is relatively large, such as at least 50, at least 100, at least 150, or even more. In particular examples, the binding regions of the FPC nucleic acid molecules are substantially or entirely free of undesired (e.g., repetitive, conservative, or homologous) nucleic acid sequences of the target nucleic acid molecule (e.g., genomic target nucleic acid molecule or RNA).

The number of FPC nucleic acid molecules in a probe can vary. In particular examples, the probe includes at least 10 different FPC nucleic acid molecules, such as at least 25, at least 50, at least 100, at least 250, at least 500, at least 1000, at least 2000, at least 5000, at least 10,000, or at least 50,000 different FPC nucleic acid molecules.

The length of the binding regions can vary, but are generally several hundred to several thousand base pairs. In some examples, binding regions are smaller, such as a few as to 50 nucleotides. In other examples, binding regions are longer, such as at least 100 nucleotides, at least 200 nucleotides, at least 1000 nucleotides, at least 2000 nucleotides, or at least 5000 nucleotides in length, such as 100 to 10,000 or 100 to 6000 nucleotides in length).

The length of the plurality of nucleic acid molecules in a probe can vary. Within a single FPC nucleic acid molecule, the different binding regions can vary over a range of different sizes, for example with an average length of 20 to 100 nucleotides or with an average length of at least 1000 to 5000 nucleotides. In some examples, the plurality of nucleic acid molecules are substantially each at least 1000 nucleotides, such as at least 2000 nucleotides, or at least 5000 nucleotides. In other examples, for example when the plurality of nucleic acid molecules are labeled by nick translation, the length of the plurality of nucleic acid molecules is shorter, such as 100 to 500 nucleotides or 50 to 200 nucleotides.

The plurality of nucleic acid molecules can be labeled with a detectable agent, such as an optically detectable moiety, such as a fluorescent moiety, a hapten that can be detected indirectly via a labeled specific binding partner (such as an antibody or avidin), or an enzyme that is capable of converting a substrate into an optically detectable product.

Methods are provided herein to generate the disclosed probes, which are substantially or entirely free of undesired (e.g., repetitive, conserved domain, or homologous) nucleic acid sequence. In particular examples, the probes exhibit increased signal relative to probes that include substantial amounts of undesired (e.g., repetitive, conserved domain, or homologous) nucleic acid sequences. In some examples, the probes can be produced reliably and inexpensively in quantities sufficient for automated applications of chromosomal in situ hybridization.

Thus, one aspect of the present disclosure concerns methods for producing nucleic acid probes that include a plurality of FPC nucleic acid molecules. In one example, the methods include joining at least a first binding region and a second binding region, thereby producing a plurality of nucleic acid molecules substantially all of which nucleic acid molecules each include a contiguous at least first binding region and second binding region, wherein the contiguous at least first binding region and second binding region are complementary to non-contiguous portions and unique sequences of a target nucleic acid molecule, and wherein the plurality of nucleic acid molecules form the probe. In some examples, the at least first binding region and the second binding region are substantially free of undesired (e.g., repetitive, conserved domain, or homologous) nucleic acid sequences of the target nucleic acid molecule. The multiple segments are joined together to form a linear permuted nucleic acid template. In particular examples, the binding regions of a FPC nucleic acid molecule are joined or ligated to one another enzymatically (e.g., using a ligase). For example, binding regions can be joined in a blunt-end ligation or at a restriction site. Chemical ligation and amplification can also be used to join binding regions. In some examples, the binding regions are separated by linkers.

The method can further include amplifying the plurality of nucleic acid molecules (i.e. FPC nucleic acid molecules) to produce a plurality of nucleic acid molecule amplicons (i.e. FPC nucleic acid molecule amplicons) to form the probe. Essentially any amplification procedure can be used to produce FPC nucleic acid molecule amplicons, such as PCR, DOP-PCR, NASBA, RCA, T7/Primase amplification, SDA, LAMP, 3SR and MDA. In certain embodiments, the amplification is performed using an isothermal amplification process, such as MDA. The FPC nucleic acid molecule amplicons can be produced in multiple serial amplification reactions (such as two, three or four serial amplification reactions).

In some examples, the plurality of FPC nucleic acid molecules or amplicons thereof are labeled, for example, for use in in situ hybridization analysis of metaphase or interphase nuclei. In particular examples, labeling is performed after amplification of the FPC nucleic acid molecule templates. The label can be any directly or indirectly detectable moiety that can be attached to a nucleic acid (or a nucleotide constituent), e.g., by chemical or enzymatic labeling. For example, the label can be a hapten (such as DNP or biotin), a ligand, an enzyme, a radioisotope or fluorescent moiety (such as a fluorophore, or a fluorescent nanoparticle, e.g., a semiconductor nanocrystal or "quantum dot").

The one or more binding regions can be generated in a number of different ways. For example, binding regions that are entirely or substantially free of undesired (e.g., repetitive, conservative, or homologous) nucleic acid sequences and correspond to a target nucleic acid sequence (e.g., genomic nucleic acid sequence or RNA) can be produced by one or more of the following: isolating the binding regions from the target nucleic acid molecule; obtaining the binding regions from the target nucleic acid molecule by subtractive hybridization; or amplifying the binding regions from the target nucleic acid molecule. For example, binding regions can be amplified from a target nucleic acid sequence (e.g., genomic target nucleic acid sequence) for example in multiple amplification reactions, generated by chemical synthesis of a nucleic acid corresponding to a target nucleic acid sequence, generated by restriction (or other) endonuclease digestion of a target nucleic acid sequence, which in some instances can be followed by selection of binding regions by physical (e.g., mechanical) shearing of a target sequence followed by elimination of repetitive nucleic acid sequences, or by any combination of these methods.

Indeed, the binding region segments can be provided by any method that produces a nucleic acid that corresponds in sequence to a repetitive nucleic acid-free (or substantially repetitive nucleic acid-free) sequence of a target nucleic acid sequence (or similarly free or substantially free of other undesired sequence present in the target nucleic acid sequence). In specific embodiments, the binding regions are provided by isolating substantially repetitive (or other undesired sequence) nucleic acid free restriction fragments from a target nucleic acid sequence (e.g., genomic target nucleic acid sequence), by obtaining substantially repetitive (or other undesired sequence) nucleic acid-free sequence from a target nucleic acid sequence by subtractive hybridization, by amplifying substantially repetitive (or other undesired sequence) nucleic acid-free sequence from a target nucleic acid sequence (e.g., genomic target nucleic acid sequence), or by a combination of these methods. In certain embodiments, the repetitive (or other undesired sequence) nucleic acid sequences are selected from a target nucleic acid sequence (e.g., genomic target nucleic acid sequence or RNA) using a computer implemented algorithm or program, such as PRIME® or RepeatMasker.

For example, binding regions that are entirely or substantially free of repetitive (or other undesired sequence) nucleic acid sequences (for example, identified using a computer implemented algorithm) can be generated in an amplification process. The different binding regions can be amplified in different amplification reactions from a nucleic acid molecule containing some or all of the binding regions of interest. For example, the different binding regions can be amplified in a PCR reaction using at least one pair of unique sequence primers. The primer(s) used for amplification of the binding regions can include a fixed oligonucleotide sequence, such as an all purine tract. Optionally, the primer can include a restriction enzyme recognition site. In some examples, the primer is selected using a computer implemented algorithm (such as OLIGO™).

In certain examples, the binding regions are produced from target nucleic acid molecules that do not naturally contain repetitive sequences characteristic of mammalian genomic DNA. Such target nucleic acid molecules include viral genomic nucleic acids molecules or RNA. In some such embodiments, binding regions can be produced directly from a target nucleic acid molecule with optional removal from the target nucleic acid molecule of sequences that reasonably may be expected to lead to increased background signal (e.g., homologous sequences or sequences encoding conserved domains). For example, if the target nucleic acid molecule is a viral genome or an RNA sequence, binding regions can be generated directly from the target molecule (for example by restriction enzyme digestion of a crude or isolated cellular nucleic acid preparation). However, possible undesired background-generating nucleic acid sequences (e.g., homologous sequences or sequences encoding conserved domains) can be removed from viral or RNA target sequence before or after generating binding regions from such target nucleic acid sequences.

In other embodiments, the binding regions are provided by amplification, digestion or the like of one or more vectors that include the target nucleic acid sequence. For example, a single vector capable of encompassing large portions of nucleic acid can be used (such as an artificial chromosome (e.g., a BAC, YAC, PAC, etc.) or certain viral vectors capable of replicating many kilobases of DNA, e.g., CMV). Alternatively, multiple vectors (such as plasmids, cosmids, phage or other viruses) that include smaller portions of the target nucleic acid sequence (e.g., genomic target nucleic acid sequence) can be used.

A target nucleic acid molecule can be any selected nucleic acid, such as DNA or RNA. In particular examples the target sequence is a genomic target sequence or genomic subsequence, for example from a eukaryotic genome, such as a human genome. In some examples, the target nucleic acid molecule is selected from a pathogen, such as a virus, bacteria, or intracellular parasite, such as from a viral genome. For example, the target nucleic acid molecule can be a sequence associated with (e.g., correlated with, causally implicated in, etc.) a disease. In certain examples, the selected target nucleic acid molecule is a target nucleic acid molecule associated with a neoplastic disease (or cancer). For example, the genomic target sequence can include at least one or least one gene associated with cancer (e.g., HER2, c-Myc, n-Myc, Abl, Bcl2, Bcl6, Rb1, p53, EGFR, TOP2A, MET, or genes encoding other receptors and/or signaling molecules, etc.) or chromosomal region associated with a cancer. For example, the target nucleic acid sequence can be associated with a chromosomal structural abnormality, e.g., a translocation, deletion, or reduplication (e.g., gene amplification or polysomy) that has been correlated with a cancer. In certain examples, the target nucleic acid sequence encompasses a genomic sequence that is reduplicated or deleted in at least some neoplastic cells. The target nucleic acid sequence can vary substantially in size, such as at least 1000 base pairs in length, at least 50,000, at least 100,000, or even at least 250,000, 500,000, or several million (e.g., at least 3 million) base pairs in overall length.

In a specific method probes are produced by amplifying a plurality of binding regions that are substantially free of undesired (e.g., repetitive) nucleic acids from a target nucleic acid sequence to produce a plurality of binding region amplicons. The plurality of binding region amplicons are ligated to produce a plurality of nucleic acid molecules, substantially all of which each include contiguous binding regions that are complementary to non-contiguous portions and unique sequences of a target nucleic acid molecule. The resulting plurality of nucleic acid molecules are amplified to produce a plurality of nucleic acid molecule amplicons, which can be labeled to produce the probe.

Methods of using the disclosed probes are also provided. For example, the probes can be used to detect a target nucleic acid molecule. In one example, the method includes contacting one or more of the disclosed probes with a sample that includes nucleic acid molecules under conditions sufficient to permit hybridization between the nucleic acid molecules in the sample and the plurality of nucleic acid molecules of the probe. The resulting hybridization is detected and in some examples quantified, wherein the presence of hybridization indicates the presence of the target nucleic acid molecule.

Kits including the nucleic acids disclosed herein are also provided. For example, kits can include one or more of: FPC nucleic acid molecule templates useful for producing probes of the present disclosure and FPC nucleic acid molecule amplicons (which can be labeled or unlabeled). The kit can also include one or more ancillary reagents such as buffers, labels, primers, enzymes and the like.

An exemplary probe useful for detecting a region of the human genome including the HER2 gene (referred to herein as a HER2 probe or human HER2 probe) and methods for making the probe are provided herein. Although the specification describes a HER2 probe in detail, one skilled in the art will appreciate that similar methods can be used to produce a probe for any target nucleic acid sequence (e.g., genomic target nucleic acid molecule or RNA) of interest. In addition, one skilled in the art will appreciate that the particular methods provided herein can be varied while achieving a similar result. For example, from 1 to 178 representative binding regions (which are substantially free of repetitive nucleic acid sequence) of the human genomic sequence that includes the HER2 gene can be amplified (e.g., as described in Example 1 or as otherwise known to one of ordinary skill in the art) using the primer pairs and commercially available BAC clone templates identified in Table 1 (see Example 1). In some examples, a human HER2 probe includes from 2 to 178 of such exemplary binding regions (e.g., 2, 3, 4, 5, 6, 7, 8, 9, 10, 15, 20, 25, 30, 40, 50, 100 or 150 of such exemplary binding regions). In particular embodiments of a human HER2 probe, the nucleic acid sequence of each binding region consists of the nucleic acid sequence amplified from the applicable BAC clone using the applicable primer pair identified in Table 1. In other embodiments, the representative binding regions of the human genomic sequence that contains the HER2 gene are ligated together (with or without linkers between binding regions) in random order or in random orientation (or both) to produce a plurality of FPC HER2 nucleic acids. In another embodiment, the exemplary binding regions of the human genomic sequence that contains the HER2 gene are ligated together (with or with linkers between segments) in the order such segments would be found in the native target nucleic acid sequence (however, substantially lacking the intervening repetitive nucleic acid sequences) in random or other non-native orientation.

Terms

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biol-*

*ogy and Biotechnology: a Comprehensive Desk Reference,* published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" is used synonymously with the phrase "more than one," that is, two or more. It is further to be understood that all base sizes or amino acid sizes, and all molecular weight or molecular mass values, given for nucleic acids or polypeptides are approximate, and are provided for description. The term "comprises" means "includes." The abbreviation, "e.g.," is derived from the Latin exempli gratia, and is used herein to indicate a non-limiting example. Thus, the abbreviation "e.g.," is synonymous with the term "for example." Although methods and materials similar or equivalent to those described herein can be used in the practice or testing of this disclosure, suitable methods and materials are described below.

In order to facilitate review of the various embodiments of this disclosure, the following explanations of specific terms are provided:

"Amplification of a nucleic acid molecule" refers to methods used to increase the number of copies of a nucleic acid molecule, such as a binding region of a target nucleic acid molecule or a FPC nucleic acid molecule. The resulting products can be referred to as amplicons or amplification products. Methods of amplifying nucleic acid molecules are known in the art, and include MDA, PCR, DOP-PCR, RCA, T7/Primase-dependent amplification, SDA, 3SR, NASBA, and LAMP, among others.

"Binding or stable binding" refers to the association between two substances or molecules, such as the hybridization of one nucleic acid molecule (e.g., a binding region) to another (or itself) (e.g., a target nucleic acid molecule). A FPC nucleic acid molecule binds or stably binds to a target nucleic acid molecule if a sufficient amount of the FPC nucleic acid molecule forms base pairs or is hybridized to its target nucleic acid molecule to permit detection of that binding.

Binding can be detected by any procedure known to one skilled in the art, such as by physical or functional properties of the target:FPC nucleic acid complex. Physical methods of detecting the binding of complementary strands of nucleic acid molecules include, but are not limited to, such methods as DNase I or chemical footprinting, gel shift and affinity cleavage assays, Northern blotting, dot blotting and light absorption detection procedures. In another example, the method involves detecting a signal, such as a detectable label, present on one or both nucleic acid molecules (e.g., a label associated with the FPC nucleic acid molecule).

A "binding region" is a segment or portion of a target nucleic acid molecule that is unique to the target molecule, and in some examples is free or substantially free of repetitive (or other undesired) nucleic acid sequence. The nucleic acid sequence of a binding region and its corresponding target nucleic acid molecule have sufficient nucleic acid sequence complementarity such that when the two are incubated under appropriate hybridization conditions, the two molecules will hybridize to form a detectable complex. A target nucleic acid molecule can contain multiple different binding regions, such as at least 10, at least 50, at least 100, or at least 1000 unique binding regions. In particular examples, a binding region is typically several hundred to several thousand base pairs in length. However, in some examples a binding region is shorter, such as 50 to 200 base pairs in length. When obtaining binding regions from a target nucleic acid sequence, the target sequence can be obtained in its native form in a cell, such as a mammalian cell, or in a cloned form (e.g., in a vector).

A nucleic acid molecule is said to be "complementary" with another nucleic acid molecule if the two molecules share a sufficient number of complementary nucleotides to form a stable duplex or triplex when the strands bind (hybridize) to each other, for example by forming Watson-Crick, Hoogsteen or reverse Hoogsteen base pairs. Stable binding occurs when a nucleic acid molecule (e.g., FPC nucleic acid molecule) remains detectably bound to a target nucleic acid sequence (e.g., genomic target nucleic acid sequence) under the required conditions.

Complementarity is the degree to which bases in one nucleic acid molecule (e.g., FPC nucleic acid molecule) base pair with the bases in a second nucleic acid molecule (e.g., genomic target nucleic acid sequence). Complementarity is conveniently described by percentage, that is, the proportion of nucleotides that form base pairs between two molecules or within a specific region or domain of two molecules. For example, if 10 nucleotides of a 15 contiguous nucleotide region of a FPC nucleic acid molecule form base pairs with a target nucleic acid molecule, that region of the FPC nucleic acid molecule is said to have 66.67% complementarity to the target nucleic acid molecule.

In the present disclosure, "sufficient complementarity" means that a sufficient number of base pairs exist between one nucleic acid molecule or region thereof (such as a region of a FPC nucleic acid molecule) and a target nucleic acid sequence (e.g., genomic target nucleic acid sequence) to achieve detectable binding. A thorough treatment of the qualitative and quantitative considerations involved in establishing binding conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

A "computer implemented algorithm" is an algorithm or program (set of executable code in a computer readable medium) that is performed or executed by a computing device at the command of a user. In the context of the present disclosure, computer implemented algorithms can be used to facilitate (e.g., automate) selection of polynucleotide sequences with particular characteristics, such as identification of repetitive (or other undesired, e.g., background producing) nucleic acid sequences or unique binding regions of a target nucleic acid sequence. Typically, a user initiates execution of the algorithm by inputting a command, and setting one or more selection criteria, into a computer, which is capable of accessing a sequence database. The sequence database can be encompassed within the storage medium of the computer or can be stored remotely and accessed via a connection between the computer and a storage medium at a nearby or remote location via an intranet or the internet. Following initiation of the algorithm, the algorithm or program is executed by the computer, e.g., to select one or more polynucleotide sequences that satisfy the selection criteria. Most commonly, the selected polynucleotide sequences are then displayed (e.g., on a screen) or outputted (e.g., in printed format or onto a computer readable medium).

The term "corresponding" in reference to a first and second nucleic acid (for example, a binding region and a target nucleic acid sequence) indicates that the first and second nucleic acid share substantial sequence identity or complementarity over at least a portion of the total sequence of the first and/or second nucleic acid. Thus, a binding region corresponds to a target nucleic acid sequence if the binding region possesses substantial sequence identity or complementarity (e.g., reverse complementarity) with (e.g., if it is at least 80%, at least 85%, at least 90%, at least 95%, or even 100% identical or complementary to) at least a portion of the target nucleic acid sequence. For example, a binding region can correspond to a target nucleic acid sequence if the binding region possesses substantial sequence identity to one strand of a double-stranded target nucleic acid sequence (e.g., genomic target DNA sequence) or if the binding region is substantially complementary to a single-stranded target nucleic acid sequence (e.g. RNA or an RNA viral genome).

A "fragmented, permuted, concatenated nucleic acid molecule (FPC) nucleic acid molecule" refers to one or more nucleic acids in which constituent binding regions or segments that correspond to a target nucleic acid molecule are present in an order or orientation that differs from the order or orientation of the binding regions in the target nucleic acid sequence (such as a genomic target nucleic acid sequence). That is, the contiguous binding regions of the FPC nucleic acid molecule can be complementary to non-contiguous portions and unique sequences of a target nucleic acid molecule. The binding regions present in one or more FPC nucleic acid molecules can include all of the polynucleotide sequence present in the target nucleic acid molecule or a subset of the polynucleotide sequence present in the target nucleic acid molecule. For example, in some examples FPC nucleic acid molecules are entirely or substantially free of repetitive or other undesired nucleic acid sequence. FPC nucleic acid molecules can be used as templates in an amplification reaction, thereby producing FPC nucleic acid molecule amplicons.

Because FPC nucleic acid molecules include segments (binding regions) of the corresponding target nucleic acid sequence (e.g., genomic target nucleic acid sequence), they are said to be fragmented. The order or orientation (or both) of the binding regions is different in a FPC nucleic acid molecule relative to the corresponding target nucleic acid sequence (e.g., genomic target nucleic acid sequence), and thus the molecules are said to be permuted. FPC nucleic acid molecules include a plurality of ligated or linked binding regions, thereby forming a linear nucleic acid molecule, and are thus said to be concatenated.

When two (or more) FPC nucleic acid molecules corresponding to the same target nucleic acid molecule are compared, the first and second (and any additional) FPC nucleic acid templates can include subsets of binding regions of the target sequence that are largely overlapping but in an order or orientation that differs between the first and second FPC nucleic acid molecules, or the first and second FPC nucleic acid molecules can include different subsets of subsequences (segments) of the target nucleic acid sequence.

A "genome" is the total genetic constituents of an organism. In the case of eukaryotic organisms, the genome is contained in a haploid set of chromosomes of a cell. In the case of prokaryotic organisms, the genome is contained in a single chromosome, and in some cases one or more extra-chromosomal genetic elements, such as episomes (e.g., plasmids). A viral genome can take the form of one or more single or double stranded DNA or RNA molecules depending on the particular virus.

The term "isolated" in reference to a biological component (such as a nucleic acid molecule, protein, or cell), refers to a biological component that has been substantially separated or purified away from other biological components in the cell of the organism, or the organism itself, in which the component naturally occurs, such as other chromosomal and extra-chromosomal DNA and RNA, proteins, cells, and organelles. Nucleic acid molecules that have been "isolated" include nucleic acid molecules purified by standard purification methods. The term also encompasses nucleic acids prepared by amplification or cloning as well as chemically synthesized nucleic acids.

A "label" is a detectable compound or composition that is conjugated directly or indirectly to another molecule (such as a FPC nucleic acid molecule) to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes disclosed herein are described below. Methods for labeling nucleic acids, and guidance in the choice of labels useful for various purposes, are discussed, e.g., in Sambrook and Russel., in *Molecular Cloning: A Laboratory Manual*, 3$^{rd}$ Ed., Cold Spring Harbor Laboratory Press (2001) and Ausubel et al., in *Current Protocols in Molecular Biology*, Greene Publishing Associates and Wiley-Intersciences (1987, and including updates).

A "nucleic acid" is a deoxyribonucleotide or ribonucleotide polymer in either single or double stranded form, and unless otherwise limited, encompasses analogues of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in a polynucleotide. A nucleotide sequence refers to the sequence of bases in a polynucleotide.

A nucleic acid "segment" is a subportion or subsequence of a target nucleic acid molecule. A nucleic acid segment can be derived hypothetically or actually from a target nucleic acid molecule in a variety of ways. For example, a segment of a target nucleic acid molecule (such as a genomic target nucleic acid molecule) can be obtained by digestion with one or more restriction enzymes to produce a nucleic acid segment that is a restriction fragment. Nucleic acid segments can also be produced from a target nucleic acid molecule by amplification, by hybridization (for example, subtractive hybridization), by artificial synthesis, or by any other procedure that produces one or more nucleic acids that correspond in sequence to a target nucleic acid molecule. A particular example of a nucleic acid segment is a binding region.

A "probe" or a "nucleic acid probe" is a nucleic acid molecule that is capable of hybridizing with a target nucleic acid molecule (e.g., genomic target nucleic acid molecule) and, when hybridized to the target, is capable of being detected either directly or indirectly. Thus probes permit the detection, and in some examples quantification, of a target nucleic acid molecule. In particular examples a probe includes a plurality of nucleic acid molecules, such as a heterogeneous mixture of FPC nucleic acid molecules, which include binding regions derived from the target nucleic acid molecule and are thus capable of specifically hybridizing to at least a portion of the target nucleic acid molecule. Generally, once a portion of one FPC nucleic acid molecule has (and remains) hybridized to the target nucleic acid molecule other portions of the FPC nucleic acid molecule may (but need not) be physically constrained from hybridizing to those other portions' cognate binding sites in the target (e.g., such other portions are too far distant from their cognate binding sites); however, other FPC nucleic acid molecules present in the probe can bind to one another, thus amplifying signal from the probe. A probe can be referred to as a "labeled nucleic acid probe," indicating that the probe is coupled directly or indirectly to a detectable moiety or "label," which renders the probe detectable.

The phrase "substantially free of repetitive nucleic acid sequence" in reference to a nucleic acid (such as a binding region or FPC nucleic acid molecule) indicates that the nucleic acid consists exclusively or predominantly of binding regions complementary to unique sequences of a target nucleic acid molecule, and does not include an appreciable amount of repetitive nucleic acid (e.g., DNA) sequences or "repeats." Repetitive nucleic acid sequences are nucleic acid sequences within a nucleic acid sequence (such as a genome, for example a viral or mammalian genome) which encompass a series of nucleotides which are repeated many times, often in tandem arrays. The repetitive nucleic acid sequences can occur in a nucleic acid sequence (e.g., a mammalian genome) in multiple copies ranging from two to hundreds of thousands of copies, and can be clustered or interspersed on one or more chromosomes throughout a genome. In some examples, the presence of significant repetitive nuclei acid molecules in a probe can increase background signal. Repetitive nucleic acid sequences include, for example in humans, telomere repeats, subtelomeric repeats, microsatellite repeats, minisatellite repeats, Alu repeats, L1 repeats, Alpha satellite DNA, satellite 1, H, and III repeats, and Cot-1™ DNA. Thus, binding regions or FPC nucleic acid molecules that are substantially free of repetitive nucleic acid sequences can include less than about 10% repetitive nucleic acid sequences, such as less than 5%, less than 4%, less than 3%, less than 2%, or even less than 1% repetitive nucleic acid sequences. In certain examples, no detectable repetitive nucleic acid sequences are present in a binding region or FPC nucleic acid molecule that is substantially free of repetitive nucleic acid sequences.

The term "reduplicated" refers to a genomic polynucleotide sequence that is typically found in single copy in the haploid genome of a cell. Under certain conditions, such as neoplastic transformation or growth, the sequence becomes multiply replicated such that multiple (and sometimes, numerous) copies are found in the neoplastic cell. Frequently this phenomenon is referred to as "amplification" of the polynucleotide sequence. However, in the context of the present disclosure the term reduplicated may be used in lieu of the term amplification to distinguish between the genetic phenomenon of multiple replication (i.e., reduplication) in a cell, from artificial amplification of a target sequence (e.g., by PCR or other in vitro methods).

A "sample" is a biological specimen containing genomic DNA, RNA (including mRNA), protein, or combinations thereof, obtained from a subject. Examples include, but are not limited to, chromosomal preparations, peripheral blood, urine, saliva, tissue biopsy, surgical specimen, bone marrow, amniocentesis samples and autopsy material. In one example, a sample includes genomic DNA or RNA. In some examples, the sample is a cytogenetic preparation, for example which can be placed on microscope slides. In particular examples, samples are used directly, or can be manipulated prior to use, for example, by fixing (e.g., using formalin).

A "subject" includes any multi-cellular vertebrate organism, such as human and non-human mammals (e.g., veterinary subjects).

A "target nucleic acid sequence or molecule" is a defined region or particular sequence of a nucleic acid molecule, for example a genome (such as a gene or a region of mammalian genomic DNA containing a gene of interest) or an RNA sequence. In an example where the target nucleic acid sequence is a target genomic sequence, such a target can be defined by its position on a chromosome (e.g., in a normal cell), for example, according to cytogenetic nomenclature by reference to a particular location on a chromosome; by reference to its location on a genetic map; by reference to a hypothetical or assembled contig; by its specific sequence or function; by its gene or protein name, or by any other means that uniquely identifies it from among other genetic sequences of a genome. In some examples, the target nucleic acid sequence is mammalian or viral genomic sequence. In other examples, the target nucleic acid sequence is an RNA sequence.

In some examples, alterations of a target nucleic acid sequence (e.g., genomic nucleic acid sequence) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by polynucleotide polymorphisms, and/or the two different forms can be quantitatively distinguishable, such as by the number of copies of the target nucleic acid sequence that are present in a cell.

A "unique sequence primer" is a primer, such as an oligonucleotide primer, that includes a unique polynucleotide sequence, such as unique target nucleic acid sequence. A unique sequence primer can optionally include additional nucleotides (typically at its 5' end) that facilitate subsequent manipulation (e.g., restriction, ligation, cloning, etc.), such as restriction sites, or short nucleotide polymers that contain only purine (or only pyrimidine) nucleotides. The term unique sequence primer is frequently used to distinguish a primer that corresponds to a unique target nucleic acid sequence from a primer that consists of a sequence that is shared by a plurality of target nucleic acid sequences, such as a "universal primer" that corresponds to a polynucleotide sequence that is common to a family of target nucleic acid molecules (such as nucleic acids that include a linker or adapter sequence or nucleic acids cloned into a common vector) or a "random primer."

A "vector" is any nucleic acid that acts as a carrier for other ("foreign") nucleic acid sequences that are not native to the vector. When introduced into an appropriate host cell a vector may replicate itself (and, thereby, the foreign nucleic acid sequence) or express at least a portion of the foreign nucleic acid sequence. In one context, a vector is a linear or circular nucleic acid into which a target nucleic acid sequence of interest is introduced (for example, cloned) for the purpose of replication (e.g., production) and/or manipulation using standard recombinant nucleic acid techniques (e.g., restriction digestion). A vector can include nucleic acid sequences that permit it to replicate in a host cell, such as an origin of replication. A vector can also include one or more selectable marker genes and other genetic elements known in the art. Common vectors include, for example, plasmids, cosmids, phage, phagemids, artificial chromosomes (e.g., BAC, PAC, HAC, YAC) and hybrids that incorporate features of more than one of these types of vectors. Typically, a vector includes one or more unique restriction sites (and in some cases a multi-cloning site) to facilitate insertion of a target nucleic acid sequence.

In one example discussed herein, one or more binding regions substantially free of repetitive nucleic acid sequences are introduced and replicated in a vector, such as an artificial chromosome (e.g., yeast artificial chromosome, P1 based artificial chromosome, bacterial artificial chromosome (BAC)).

NUCLEIC ACID PROBES

The present disclosure provides nucleic acid probes. Such probes can be used to detect a target nucleic acid sequence, such as a genomic target nucleic acid sequence associated with disease or associated with a pathogen, or an RNA target nucleic acid sequence. For example, the probes can be used in in situ hybridization procedures that include hybridization of labeled single stranded nucleic acids of a probe to chromosome preparations, such as metaphase or interphase nuclei or tissue sections.

The disclosed nucleic acid probes include a heterogeneous plurality of individual fragmented, permuted, concatenated nucleic acid molecules (FPC nucleic acid molecules). The FPC nucleic acid molecules are said to be fragmented because they include portions or segments of the selected target nucleic acid sequence (e.g., genomic target nucleic acid sequence). The segments of the target nucleic acid sequence are referred to herein as binding regions. In some embodiments (e.g., involving human genomic target nucleic acid sequences), the binding region segments of the target nucleic acid sequence are substantially or completely free of undesired nucleic acid sequences, such as those that can increase background signal. Examples of such undesired nucleic acid sequences include repetitive nucleic acid sequences (e.g., found in mammalian genomic sequences), sequences encoding conserved domains (e.g., found in RNA sequences), and homologous sequences (e.g., found in viral genomic sequences). The binding regions have sufficient complementarily to portions of the selected target nucleic acid sequence to hybridize to (and thus detect) the target sequence. The FPC nucleic acid molecules are said to be permuted because the order or orientation of the binding regions can be different in the FPC nucleic acid molecules relative to the corresponding target nucleic acid sequence (e.g., genomic target nucleic acid sequence). The FPC nucleic acid molecules are said to be concatenated because the FPC nucleic acid molecules include a plurality of ligated or linked binding regions, thereby forming a linear nucleic acid molecule of ligated binding regions.

The FPC nucleic acid molecules of the disclosed probe compositions are substantially or completely free of repetitive nucleic acid sequences (that is, repeat sequences), or other undesired sequence, and include binding regions that each correspond to unique (either coding or non-coding) elements in the target nucleic acid sequence (e.g., genomic target nucleic acid sequence (e.g., a haploid genome). Mammalian genomes (including for example, human genomes) include numerous repetitive nucleic acid sequences or elements that account for almost half of the total genomic DNA. These repetitive sequences can be specific to a chromosome, specific to a structural element of a chromosome, or interspersed throughout the chromosomes. RNA can include regions that encode conserved domains that are not specific for the target RNA sequence. Viral genomes can include nucleic acid sequences found in other non-targeted viruses (e.g., homologous sequences), and thus are not specific for the target viral sequence. The presence of such undesired nucleic acid sequences in a probe can complicate analysis, for example by increasing background signal. The probes disclosed herein provide low non-specific (or background) signal and high specific (or target) signal. Additionally, in some embodiments, the disclosed probes can readily be produced in large (milligram to gram) amounts, for example using the methods disclosed herein.

An overview of the disclosed probes and how they are generated from exemplary target nucleic acid molecules is provided in FIGS. 1A and B.

As shown in FIG. 1A, target nucleic acid sequence (e.g., human genomic DNA) containing undesired subsequences (e.g., repetitive nucleic acid sequences) 10 or full content (e.g., repetitive nucleic acid sequence-free) target nucleic acid sequence (e.g., viral genomic nucleic acid sequences or RNA) 40 can be used to generate a probe 300 that includes a plurality of fragmented, permuted, concatenated nucleic acid molecules (FPC nucleic acid molecules) 310, 312, 314, 316, 318, 320, 322, 324, 326, 328, 330, 332. Genomic target nucleic acid sequence 10, 40 includes a plurality of binding regions 14, 16, 18 or 42, 44, 46, which can be specific for the target nucleic acid sequence. Binding regions 14, 16, 18, 42, 44, 46 can include coding or non-coding sequence. For simplicity, only three specific binding regions are shown for each genomic target nucleic acid sequence 10, 40 (14, 16, 18 and 42, 44, 46, respectively). However, one skilled in the art will appreciate that many more binding regions may be present (for example in target nucleic acid sequence regions 26 and 48), such as at least 10, at least 50, at least 100, at least 200, at least 1000, or even at least 10,000 binding regions (e.g., 100 to 500 or 100 to 1000 binding regions). In FIG. 1A, the arrows shown in each binding region 14, 16, 18, 42, 44, 46 represent a reference direction for the subject nucleic acid sequence (e.g., → indicates 5' to 3' and ← indicates 3' to 5'). The length of each binding region 14, 16, 18, 42, 44, 46 can vary. In particular examples, each binding region 14, 16, 18, 42, 44, 46 is several hundred to several thousand base pairs in length, such as at least 200, at least 500, at least 1000, at least 5000, at least 10,000, at least 50,000, or at least 100,000 nucleotides in length.

A target nucleic acid sequence may (as shown in 10) or may not (as shown in 40) include undesired nucleic acid sequences (e.g., repetitive nucleic acid sequences) 20, 22, 24. For example, target nucleic acid sequence 10 can be a human sequence associated with disease, target nucleic acid sequence 40 can be a viral genomic sequence or mammalian (e.g., human) RNA (viral genomes and mammalian RNA sequences generally do not have repetitive nucleic acid elements). For simplicity, only three undesired nucleic acid sequences (e.g., repetitive nucleic acid sequences) 20, 22, 24 are shown for target nucleic acid sequence 10. However, one skilled in the art will appreciate that many more undesired nucleic acid sequences (e.g., repetitive nucleic acid sequences) may be present (for example in region 26), such as at least 10, at least 50, at least 100 (e.g., between about 100 and about 200), at least 1000, or even at least 10,000 undesired nucleic acid sequences (e.g., repetitive nucleic acid sequences).

As shown in FIG. 1A at step 60, target nucleic acid sequence 10 or 40 is used to generate a population of binding regions 100 and 140. Each population of binding regions 100 and 140 includes a plurality of binding regions 114, 116, 118 or 142, 144, 146 obtained from the corresponding target nucleic acid sequence 10 or 40, respectively. The number of binding regions corresponding to the target nucleic acid sequence 10, 40 can vary extensively. One skilled in the art will appreciate that additional binding regions (e.g., in target regions 126 or 148) can be present in a population of binding regions 100 and 140. For example, although only three binding regions are shown for population 100 and 140 (114, 116, 118 and 142, 144, 146, respectively) for simplicity, one skilled in the art will appreciate that many more binding regions may be present (for example as represented by 126 and 148, respectively), such as at least 10, at least 50, at least 100, at least 200, at least 1000, at least 5000, or even at least 10,000 different binding regions that correspond to a single target nucleic acid sequence 10, 40.

The length of each binding region 114, 116, 118, 142, 144, 146 can vary. In particular examples, binding regions 114, 116, 118, 142, 144, 146 are several hundred to several thousand base pairs in length, such as at least 200, at least 500, at least 1000, at least 5000, at least 10,000, at least 50,000, or at least 100,000 nucleotides in length (e.g., from about 100 to about 6000 nucleotides) in length. The term nucleotide refers not only to nucleotides of a single stranded nucleic acid molecule, e.g., that has been denatured to allow for hybridization to a target, but also to indicates the length in base pairs of double-stranded nucleic acid molecules. Thus, an individual binding region can be at least 20 nucleotides, at least 100 nucleotides, at least 200 nucleotides, at least 300 nucleotides, at least 400 nucleotides, at least 500 nucleotides, at least 1000 nucleotides (1 kb), or at least 2500 nucleotides in length or more. Larger binding regions are, of course, permissible. However, due to the presence of interspersed repetitive sequences 20, 22, 24, in mammalian genomic DNA, it is rare that expanses of greater than this length occur in a human genomic target nucleic acid sequence. However, greater lengths of binding regions may be obtained, for example, from larger viral genomes, which generally do not include repetitive nucleic acid sequences. Individual binding regions within the same probe molecule can be relatively consistent in size, or they can vary from binding region to binding region across the full extent of the range.

The population of binding regions 100 and 140 are substantially free of undesired nucleic acid sequences (e.g., repetitive nucleic acid sequences) 20, 22, 24. In some examples, each population of binding regions 100, 140 contains less than 10% undesired nucleic acid sequences (e.g., repetitive nucleic acid sequences), such as less than 5%, less than 1%, less than 0.1% or even less than 0.01%. In some examples, for example when the target nucleic acid molecule includes undesired nucleic acid sequence (e.g., a genomic target nucleic acid sequence), at least 80% (such as, at least 85%, at least 90%, at least 95%, at least 98%, or at least 99%) of the undesired nucleic acid sequence is removed from the target nucleic acid sequence.

The population of binding regions 100, 140 can optionally be subjected to one or more rounds of nucleic acid amplification 200. In some examples, the population of binding regions 100, 140 is subjected to at least one round of amplification, thereby producing a population of binding region amplicons. Optionally, the population of binding regions 100, 140 can be amplified by sequence-specific amplification (such as, PCR) up to three or more times with intervening dilutions of the templates (e.g., 1:200 dilution). In addition to increasing the number of binding regions for any subsequent steps, this procedure also dilutes any residual, original template molecules by a large factor, thereby reducing potential contaminants, which may be inadvertently incorporated into the probe and lead to background hybridization.

The plurality of binding regions 114, 116, 118 (and in some examples amplified binding regions) are subjected to conditions that permit ligation 250 to form contiguous nucleic acid of binding regions, thereby resulting in a population or plurality of fragmented, permuted, concatenated nucleic acid molecules (FPC nucleic acid molecules). In some examples, multiple separate ligation reactions are performed, such as separate ligation reactions that include at least five different binding regions, at least 10 different binding regions, or at least different binding regions (e.g., 5 to 50 or 10 to 20 different binding regions). In particular examples, at least five different or at least 20 different ligation reactions are performed. Similarly, binding regions 142, 144, 146 can be subjected to ligation 250, but this is not shown in FIG. 1A. This mixture of individual FPC nucleic acid molecules is referred to as probe 300. For simplicity, only 12 exemplary ligation products (referred to herein as FPC nucleic acid molecules) 310, 312, 314, 316, 318, 320, 322, 324, 326, 328, 330, 332 are shown. The particular FPC nucleic acid molecules 310, 312, 314, 316, 318, 320, 322, 324, 326, 328, 330, 332 shown in FIG. 1A are illustrative only, as one skilled in the art will recognize that numerous other combinations of binding regions 114, 116, 118 are possible. The individual FPC nucleic acid molecules of the probe 300 can be made up of largely overlapping subsets of binding regions of the same target nucleic acid sequence (e.g., genomic target nucleic acid sequence), or of predominantly different binding regions of the same target nucleic acid sequence.

The resulting FPC nucleic acid molecules 310, 312, 314, 316, 318, 320, 322, 324, 326, 328, 330, 332 that form probe 300 are linear nucleic acids that include multiple contiguous binding regions 114, 116, 118 (such as ten or more binding regions, twenty-five or more binding regions, fifty or more binding regions, one-hundred or more binding regions or one-hundred and fifty or more binding regions), wherein each binding region 114, 116, 118 corresponds to at least a portion of the target nucleic acid sequence (e.g., genomic target nucleic acid sequence) 10. The FPC nucleic acid molecules 310, 312, 314, 316, 318, 320, 322, 324, 326, 328, 330, 332 include segments of the corresponding target nucleic acid sequence (e.g., genomic target nucleic acid sequence) 10, and are thus said to be fragmented. The order or orientation of the binding regions 114, 116, 118 can be changed in FPC nucleic acid molecules 310, 312, 314, 316, 318, 320, 322, 324, 326, 328, 330, 332 relative to the corresponding target nucleic acid sequence (e.g., genomic target nucleic acid sequence) 10, and are thus said to be permuted. The FPC nucleic acid molecules 310, 312, 314, 316, 318, 320, 322, 324, 326, 328, 330, 332 include a plurality of ligated or linked binding regions 114, 116, 118, thereby forming a linear nucleic acid molecule, and are thus said to be concatenated.

For illustration purposes only, FPC nucleic acid molecules 310, 312, 314 include three binding regions, FPC nucleic acid molecules 316, 318, 320 include four binding regions, FPC nucleic acid molecules 322, 324, 326 include two binding regions, and FPC nucleic acid molecules 328, 330, 332 include at least five binding regions. FPC nucleic acid molecules of probe 300 can include more than one of the same binding region (e.g., FPC nucleic acid molecule 316 includes two of binding region 114, and FPC nucleic acid molecule 332 includes three of binding region 116 and two of binding region 118). Although FPC nucleic acid molecules having only two to five binding regions are shown, it is appreciated that FPC nucleic acid molecules generally have many more binding regions (but two to five are shown for illustration of the overall concepts provided by this disclosure). For example, FPC nucleic acid molecules can include at least 50, at least 80, at least 100, or at least 150 binding regions, such as 50 to 100, 50 to 80, 100 to 200, 100 to 150, or 150 to 200 binding regions.

The one or more binding regions 114, 116, 118 that make up each FPC nucleic acid molecule can be arranged in the same orientation and order as found in the genomic target nucleic acid sequence 10 (e.g., as shown in FPC nucleic acid molecule 310), wherein the target nucleic acid molecule includes repetitive nucleic acid sequence (and thus the sequence of the FPC nucleic acid molecule and the target nucleic acid molecule are different). Alternatively (and more commonly), the one or more binding regions 114, 116, 118 that make up each FPC nucleic acid molecule is in a different orientation or order (or both) relative to the orientation or order (or both) of the binding regions as found in the selected target nucleic acid sequence (e.g., genomic target nucleic acid sequence) 10 and with respect to each other. Thus, the binding region elements or segments of the FPC nucleic acid molecules are "permuted" with respect to the target nucleic acid sequence (e.g., genomic target nucleic acid sequence).

For example, FPC nucleic acid molecule 314 shows an example where the orientation (but not the order) of binding region 118 is changed relative to the target nucleic acid sequence (e.g., genomic target nucleic acid sequence) 10. In FPC nucleic acid molecule 314, the orientation of binding region 118 is reversed (the arrow is in the opposite direction) relative to the genomic target nucleic acid sequence 10, but the order of binding regions 114, 116, 118 is unchanged relative to the target nucleic acid sequence (e.g., genomic target nucleic acid sequence) 10. FPC nucleic acid molecule 312 shows an example where the order (but not the orientation) of the binding regions 114, 116, 118 is changed relative to the order of the target nucleic acid sequence (e.g., genomic target nucleic acid sequence) 10. In FPC nucleic acid molecule 312, the order of binding regions 114, 116, 118 is different relative to the genomic target nucleic acid sequence 10 (114, 118, 116 versus, 14, 16, 18), but the orientation of the binding regions 114, 116, 118 is unchanged relative to the target nucleic acid sequence (e.g., genomic target nucleic acid sequence) 10 (the arrows are in the same direction). The remaining exemplary FPC nucleic acid molecules 316, 318, 320, 322, 324, 326, 328, 330, 332 show examples of where both the orientation and the order of the binding regions 114, 116, 118 is changed relative to the binding regions 14, 16, 18, of target nucleic acid sequence (e.g., genomic target nucleic acid sequence) 10.

The FPC nucleic acid molecules 310, 312, 314, 316, 318, 320, 322, 324, 326, 328, 330, 332 can be amplified, labeled, or both, 350, to generate a probe containing amplified and labeled FPC nucleic acid molecules. As shown in FIG. 1B, the binding regions are mixed and ligated for form a population of FPC nucleic acid molecules. These FPC nucleic acid molecules can be used as templates in an amplification reaction to generate greater amounts of FPC nucleic acid molecules (referred to as FPC nucleic acid molecule amplicons), labeled with a detectable label, or both. The FPC nucleic acid molecule amplicons can be pooled to form a probe of the present disclosure. In some examples, FPC nucleic acid molecules are both amplified and labeled. In a specific example, nick translation is used to label the FPC nucleic acid molecules, which also fragments the FPC nucleic acid molecules. This results in the production of a probe composed of shorter labeled FPC nucleic acid molecules, such as FPC nucleic acid molecules that are less than 1000 nucleotides in length, such as less than 500 or less than 100 nucleotides in length (e.g., 50 to 1000 or 100 to 500 nucleotides in length). In another example, FPC nucleic acid molecules (or FPC nucleic acid molecule amplicons) are chemically labeled. Such a method typically does not fragment the FPC nucleic acid molecules.

The FPC nucleic acid molecules 310, 312, 314, 316, 318, 320, 322, 324, 326, 328, 330, 332 can have different lengths. In one example, for example wherein FPC nucleic acid molecules 310, 312, 314, 316, 318, 320, 322, 324, 326, 328, 330, 332 of probe 300 are not fragmented, the FPC nucleic acid molecules are generally long, such as at least 1000 nucleotides, at least 2000 nucleotides, at least 5000 nucleotides, at least 10,000 nucleotides, at least 50,000 nucleotides, or at least 100,000 nucleotides in length, such as more than 150, 000, or more than 200,000 nucleotides (200 kb) in length. In one example, FPC nucleic acid molecules are 2 to 50 kb in length, such as 2 to 10 kb in length. In some examples, the average length of each FPC nucleic acid molecule in probe 300 is at least 2 kb to 10 kb.

In another example, FPC nucleic acid molecules 310, 312, 314, 316, 318, 320, 322, 324, 326, 328, 330, 332 of probe 300 are fragmented. For example, FPC nucleic acid molecules can be fragmented (e.g., at 350) using nick translation to label the FPC nucleic acid molecules, thereby generating a probe of labeled FPC nucleic acid molecule fragments. In this example, the FPC nucleic acid molecules of the probe are shorter, such as at least 40 nucleotides, at least 50 nucleotides, at least 100 nucleotides, or at least 1000 nucleotides in length. In some examples, the average length of each FPC nucleic acid molecule fragments in a probe is at least 50 nucleotides, such as 50 to 1000 nucleotides. In some embodiments, substantially all (at least 90%, at least 95%, or at least 98%) of the fragments of a FPC nucleic acid molecule will include at least two binding regions (such as at least three, five or ten binding regions) with each binding region in a particular FPC nucleic acid molecule fragment being complementary to non-contiguous and unique sequences of the target nucleic acid molecule and most fragments typically not including all of the same (or even any of the same) at least two binding regions.

Figure 2A:
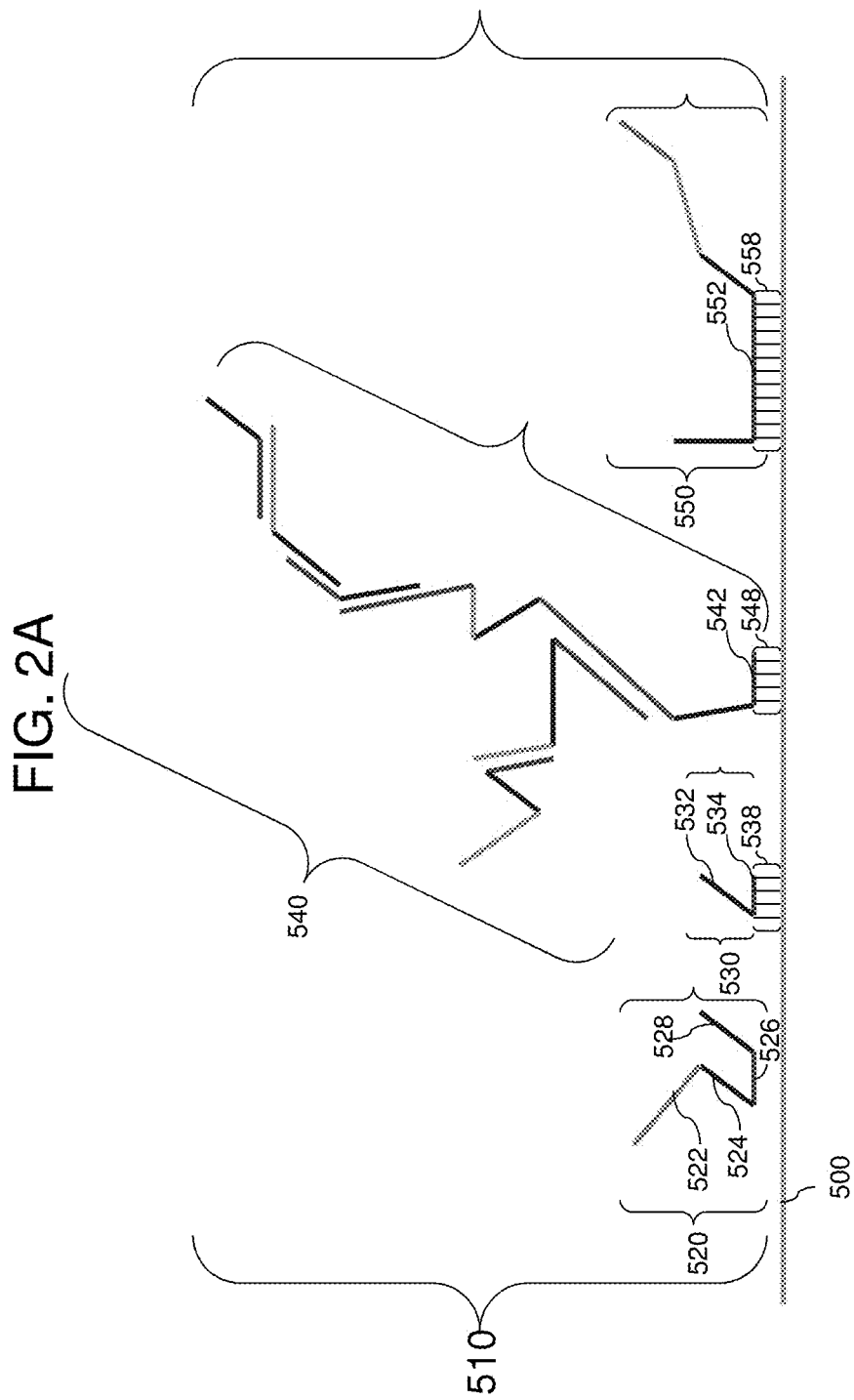
FIG. 2A is a schematic illustration showing a probe 510, which includes a plurality of FPC nucleic acid molecules 520, 530, 540, 550 hybridized 538, 548, 558 to a target nucleic acid sequence 500.
Figure 2B:
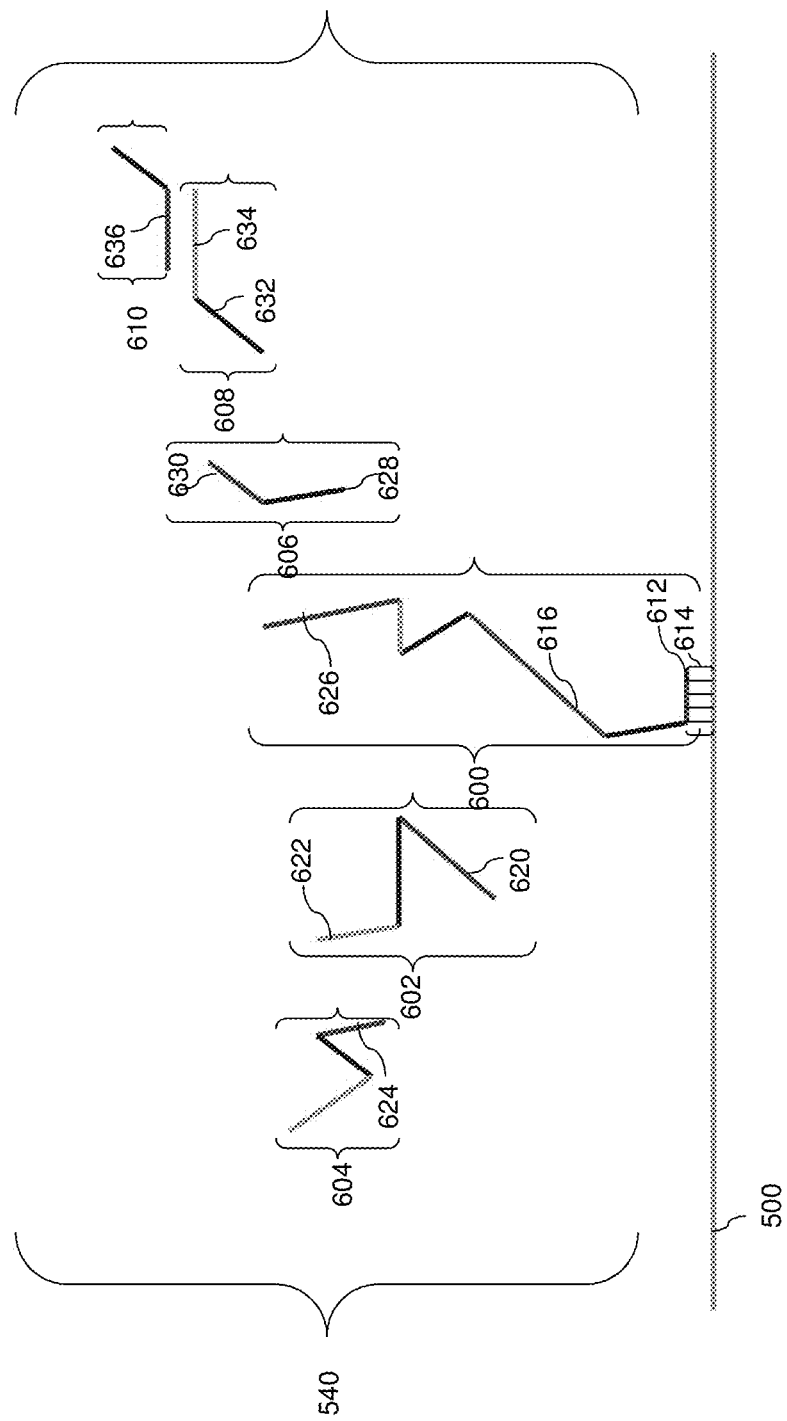
FIG. 2B is a schematic illustration showing how a plurality of FPC nucleic acid molecules 600, 602, 604, 606, 608, 610 amplify signal resulting from hybridization of FPC nucleic acid molecules directly or indirectly to target nucleic acid sequence 500.

FIGS. 2A and 2B show how a probe that includes a plurality of FPC nucleic acid molecules can be used to detect a target nucleic acid sequence (e.g., genomic target nucleic acid sequence). As shown in FIG. 2A, target nucleic acid sequence (e.g., genomic target nucleic acid sequence) 500 (for example in the form of a chromosome preparation) is incubated with probe 510 containing a plurality of FPC nucleic acid molecules 520, 530, 550 (540 in FIG. 2A includes a plurality of FPC nucleic acid molecules 600, 602, 604, 606, 608, 610 (see FIG. 2B for more detail)) under conditions that permit hybridization between FPC nucleic acid molecules of the probe 510 directly (e.g., 520, 530, 550) or indirectly (e.g., 540) to the target nucleic acid sequence (e.g., genomic target nucleic acid sequence) 500. Each FPC nucleic acid molecule 520, 530, 550, 600, 602, 604, 606, 608, 610 includes two or more binding regions. For example, FPC nucleic acid molecule 520 includes binding regions 522, 524, 526, 528. The binding regions that comprise a FPC nucleic acid molecule 520, 530, 550, 600, 602, 604, 606, 608, 610 have sufficient complementary to a corresponding portion of the target nucleic acid sequence (e.g., genomic target nucleic acid sequence) 500 such that when incubated under the appropriate conditions, at least one binding region hybridizes to its reverse complementary sequence on the target nucleic acid sequence (e.g., genomic target nucleic acid sequence) 500. For example, binding region 534 of FPC nucleic acid molecule 530 is has a sufficient degree of complementary to target nucleic acid sequence (e.g., genomic target nucleic acid sequence) 500 to permit hybridization 538 between the FPC nucleic acid molecule 530 and the target nucleic acid sequence (e.g., genomic target nucleic acid sequence) 500. Similar hybridization is observed between binding regions 542, 552 and target nucleic acid sequence (e.g., genomic target nucleic acid sequence) 500 (see for example 548, 558). Hybridization between binding region 526 and target nucleic acid sequence (e.g., genomic target nucleic acid sequence) 500 also occurs, but is not directly shown in FIG. 2A to reduce the complexity of the figure.

Because a FPC nucleic acid molecule 520, 530, 550, 600 can include multiple binding regions that are discontinuous (either in order, orientation, or both) relative to the target nucleic acid sequence (e.g., genomic target nucleic acid sequence) 500, at least one adjacent binding region of the FPC nucleic acid molecule 520, 530, 550, 600 does not hybridize to the directly contiguous portion of the target nucleic acid molecule (e.g., genomic target nucleic acid molecule) 500 chromosome, leaving an unhybridized portion (e.g., a bubble, a loop or a tail). For example, as shown in FIG. 2A, FPC nucleic acid molecule 520 hybridizes to the target nucleic acid molecule (e.g., genomic target nucleic acid molecule) 500 via binding region 526, while the other adjacent binding regions 522, 524, 528 do not hybridize to the target nucleic acid molecule (e.g., genomic target nucleic acid molecule) 500 because they are discontinuous (either in order, orientation, or both) relative to the target nucleic acid sequence (e.g., genomic target nucleic acid sequence) 500. Similarly, FPC nucleic acid molecule 530 hybridizes to the target nucleic acid molecule (e.g., genomic target nucleic acid sequence) 500 via binding region 534, while adjacent binding region 532 does not hybridize to target nucleic acid molecule (e.g., genomic target nucleic acid sequence) 500; FPC nucleic acid molecule 550 hybridizes to the target nucleic acid molecule (e.g., genomic target nucleic acid sequence) 500 via binding region 552, while the remaining binding regions do not hybridize to target nucleic acid molecule (e.g., genomic target nucleic acid sequence) 500. This results permits amplification of a signal for detecting a target nucleic acid sequence (e.g., genomic target nucleic acid sequence), for example in a chromosome preparation.

FIG. 2B shows how a probe that includes a plurality of heterogeneous FPC nucleic acid molecules can generate an amplified signal for detecting a target nucleic acid sequence (e.g., genomic target nucleic acid sequence). As described above, individual FPC nucleic acid molecules can hybridize directly to a target nucleic acid sequence (e.g., genomic target nucleic acid sequence 500) (FIG. 2A) due to reverse complementarity of a binding region for its corresponding region of the target sequence. However, as shown in FIG. 2B, binding regions of one FPC nucleic acid molecule (e.g., 616 of FPC nucleic acid 600) can also have a sufficient degree of complementary to a binding region on another FPC nucleic acid molecule (e.g., 620 of 602) to bind to that other FPC nucleic acid molecule, thereby creating a network of FPC nucleic acid molecules originating from a single binding site on the target nucleic acid sequence (e.g., genomic target nucleic acid sequence) 500 and amplifying a signal generated from the probe. For example, at least one binding region (e.g., 620) of a second FPC nucleic acid molecule (e.g., 602) can then hybridize to an unhybridized binding region (e.g., 616) of the first FPC nucleic acid molecule (e.g., 600), again leaving at least a second binding region unhybridized (e.g., 626). Similarly a third, fourth, and so forth, FPC nucleic acid molecule (e.g., 604, 606, 608, 610) can hybridize to an unhybridized binding region of partially hybridized FPC nucleic acid molecules (e.g., 600, 602). This sequential hybridization "chain reaction" produces a network of FPC nucleic acid molecules, thereby significantly increasing detectable signal from the probe.

For example, incubation of a target nucleic acid sequence (e.g., genomic target nucleic acid sequence) 500 with probe 510 which includes a plurality of FPC nucleic acid molecules 520, 530, 550, 600, 602, 604, 606, 608, 610 can result in hybridization of FPC nucleic acid molecules to one another. As shown in FIG. 2B, FPC nucleic acid molecule 600 includes binding region 612 having a sufficient degree of complementary to genomic target nucleic acid sequence 500 to permit hybridization 614 of FPC nucleic acid molecule 600 to the target sequence (e.g., genomic target nucleic acid sequence) 500. Further amplification of signal is achieved when other FPC nucleic acid molecules bind directly or indirectly to FPC nucleic acid molecule 600. As shown in FIG. 2B, binding region 616 of FPC nucleic acid molecule 600 can hybridize to binding region 620 of FPC nucleic acid molecule 602. FPC nucleic acid molecule 602 can hybridize to FPC nucleic acid molecule 604 via the interaction of binding regions 622 and 624. FPC nucleic acid molecule 600 can hybridize to FPC nucleic acid molecule 606 via the interaction of binding regions 626 and 628. FPC nucleic acid molecule 606 can hybridize to FPC nucleic acid molecule 608 via the interaction of binding regions 630 and 632. FPC nucleic acid molecule 608 can hybridize to FPC nucleic acid molecule 610 via the interaction of binding regions 634 and 636. The interactions of the FPC nucleic acid molecules with one another (e.g., hybridization of FPC nucleic acid molecules 602, 604, 606, 608, 610 directly or indirectly to FPC nucleic acid molecule 600) in addition to the interactions of the FPC nucleic acid molecules to the target nucleic acid sequence (e.g., genomic target nucleic acid sequence) 500 (e.g., hybridization of FPC nucleic acid molecules 520, 530, 550, 600 directly to target nucleic acid sequence 500) result in an increased signal from probe 510 in the presence of target nucleic acid sequence (e.g., genomic target nucleic acid sequence) 500.

Exemplary Target Nucleic Acid Sequences

Target nucleic acid sequences or molecules include both DNA and RNA target sequences. FPC nucleic acid molecules can be generated which correspond to essentially any target sequence. In some examples, a target sequence is selected that is associated with a disease or condition, such that detection of hybridization can be used to infer information (such as diagnostic or prognostic information for the subject from whom the sample is obtained) relating to the disease or condition. In a specific example, the target nucleic acid sequence is a genomic target nucleic acid sequence, such as a mammalian or viral genomic sequence. In another specific example, the target sequence is an RNA target nucleic acid sequence.

In some examples, the target sequence is a genomic sequence, such as eukaryotic (e.g., mammalian) or viral genomic sequence. FPC nucleic acid molecules can be generated which correspond to essentially any genomic target sequence that includes at least a portion of unique non-repetitive DNA (e.g., 14, 16, 18, 42, 44, 46 in FIG. 1A). Essentially any genomic target nucleic acid sequence can be used to generate probes that include FPC nucleic acid molecules with binding regions specific for the genomic target nucleic acid sequence. For example, the genomic target sequence can be a portion of a eukaryotic genome, such as a mammalian (e.g., human), fungal or intracellular parasite genome. Alternatively, a genomic target sequence can be a viral or prokaryotic genome (such as a bacterial genome), or portion thereof. In a specific example, the genomic target sequence is associated with an infectious organism (e.g., virus, bacteria, fungi). The FPC nucleic acid molecules and probes including such molecules can correspond to individual genes (including coding and/or non-coding portions of genes) or regions of chromosomes (e.g., that include one or more genes of interest).

The target nucleic acid sequence (e.g., genomic target nucleic acid sequence) can span any number of base pairs. In one example, such as a genomic target nucleic acid sequence selected from a mammalian or other genome with substantial interspersed repetitive nucleic acid sequence, the target nucleic acid sequence spans at least 1000 base pairs. In specific examples, a target nucleic acid sequence (e.g., genomic target nucleic acid sequence) is at least 10,000, at least 50,000, at least 100,000, at least 150,000, at least 250,000, or at least 500,000 base pairs in length (such as 100 kb to 600 kb, 200 kb to 500 kb, or 300 kb to 500 kb). In examples, where the target nucleic acid sequence is from a eukaryotic genome (such as a mammalian genome, e.g., a human genome), the target sequence typically represents a small portion of the genome (or a small portion of a single chromosome) of the organism (for example, less than 20%, less than 10%, less than 5%, less than 2%, or less than 1% of the genomic DNA (or a single chromosome) of the organism). In some examples where the target sequence (e.g., genomic target nucleic acid sequence) is from an infectious organism (such as a virus), the target sequence can represent a larger proportion (for example, 50% or more) or even all of the genome of the infectious organism.

In specific non-limiting examples, a target nucleic acid sequence (e.g., genomic target nucleic acid sequence) associated with a neoplasm (for example, a cancer) is selected. Numerous chromosome abnormalities (including translocations and other rearrangements, reduplication or deletion) have been identified in neoplastic cells, especially in cancer cells, such as B cell and T cell leukemias, lymphomas, breast cancer, colon cancer, neurological cancers and the like. Therefore, in some examples, at least a portion of the target nucleic acid sequence (e.g., genomic target nucleic acid sequence) is reduplicated or deleted in at least a subset of cells in a sample.

Translocations involving oncogenes are known for several human malignancies. For example, chromosomal rearrangements involving the SYT gene located in the breakpoint region of chromosome 18q11.2 are common among synovial sarcoma soft tissue tumors. The t(18q111.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lacks a t(18q11.2) in the SYT gene region, exhibit two fusion (generated by the two labels in close proximity) signals, reflecting the two intact copies of SYT. Abnormal cells with a t(18q11.2) exhibit a single fusion signal.

Numerous examples of reduplication of genes involved in neoplastic transformation have been observed, and can be detected cytogenetically by in situ hybridization using the disclosed probes. In one example, the target nucleic acid sequence (e.g., genomic target nucleic acid sequence) is selected include a gene (e.g., an oncogene) that is reduplicated in one or more malignancies (e.g., a human malignancy). For example, HER2, also known as c-erbB2 or HER2/neu, is a gene that plays a role in the regulation of cell growth (a representative human HER2 genomic sequence is provided at GENBANK™ Accession No. NC_000017, nucleotides 35097919-35138441). The gene codes for a 185 kd transmembrane cell surface receptor that is a member of the tyrosine kinase family. HER2 is amplified in human breast, ovarian, and other cancers. Therefore, a HER2 gene (or a region of chromosome 17 that includes the HER2 gene) can be used as a genomic target nucleic acid sequence to generate probes that include FPC nucleic acid molecules with binding regions specific for HER2.

In other examples, a target nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1)) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of skill in the art. Target nucleic acid sequences (e.g., genomic target nucleic acid sequences), which have been correlated with neoplastic transformation and which are useful in the disclosed methods and for which disclosed probes can be prepared, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054.69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, API (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219, PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™ Accession No. NC_000001, complement, nucleotides 40133685-

40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128). A disclosed probe or method may include a region of the respective human chromosome containing at least any one (or more, as applicable) of the foregoing genes. For example, the target nucleic acid sequence for some disclosed probes or methods includes any one of the foregoing genes and sufficient additional contiguous genomic sequence (whether 5' of the gene, 3' of the gene, or a combination thereof) for a total of at least 100,000 base pairs (such as at least 250,000, or at least 500,000 base pairs) or a total of between 100,000 and 500,000 base pairs.

In certain embodiments, the probe specific for the target nucleic acid molecule is assayed (in the same or a different but analogous sample) in combination with a second probe that provides an indication of chromosome number, such as a chromosome specific (e.g., centromere) probe. For example, a probe specific for a region of chromosome 17 containing at least the HER2 gene (a HER2 probe) can be used in combination with a CEP 17 probe that hybridizes to the alpha satellite DNA located at the centromere of chromosome 17 (17p11.1-q11.1). Inclusion of the CEP 17 probe allows for the relative copy number of the HER2 gene to be determined. For example, normal samples will have a HER2/CEP17 ratio of less than 2, whereas samples in which the HER2 gene is reduplicated will have a HER2/CEP17 ratio of greater than 2.0. Similarly, CEP centromere probes corresponding to the location of any other selected genomic target sequence can also be used in combination with a probe for a unique target on the same (or a different) chromosome.

In other examples, a target nucleic acid sequence (e.g., genomic target nucleic acid sequence) is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the probe can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma*, *Eimeria*, *Theileria*, and *Babesia* species).

In some examples, the target nucleic acid sequence (e.g., genomic target nucleic acid sequence) is a viral genome. Exemplary viruses and corresponding genomic sequences (GENBANK™ RefSeq Accession No. in parentheses) include human adenovirus A (NC_001460), human adenovirus B (NC_004001), human adenovirus C(NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C(NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P(NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target nucleic acid sequence (e.g., genomic target nucleic acid sequence) is from an oncogenic virus, such as Epstein-Barr Virus (EBV) or a Human Papilloma Virus (HPV, e.g., HPV16, HPV18). In other examples, the target nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

Exemplary Undesired Nucleic Acid Sequences

Some target nucleic acid molecules may contain nucleotide sequences that may be reasonably expected to increase non-specific binding of a nucleic acid probe to non-target sequence (e.g., repetitive sequences in genomic nucleic acid targets, sequences encoding conserved domains in RNA targets, or homologous sequences in viral genomic nucleic acid targets). Such regions are referred to herein as undesired sequences. As described above, such potentially background-producing sequences (e.g., repetitive nucleic acid sequences) are substantially (or even completely) removed from such target sequences to generate a population of binding regions used to generate the disclosed FPC nucleic acid molecules and probes. For example, at least 80%, at least 90%, at least 95%, at least 98%, or at least 99% of potentially background-producing nucleic acid sequence (e.g., repetitive sequence, sequence encoding conserved domains, or homologous sequence) can be removed from a target sequence to generate a population of binding regions used to generate the FPC nucleic acid molecules and probes provided herein.

However, in some examples, a target nucleic acid sequence, such as a viral target genomic sequence or a target RNA sequence, may not include any or only a minor amount of undesired (e.g., potentially background-producing) nucleic acid sequences. In such examples, the undesired nucleic acid sequences (if any) may, but need not, be removed from the target sequence prior to generating a population of binding regions from the target nucleic acid sequence.

In one example, the target nucleic acid molecule is an RNA molecule, which may include sequences encoding conserved domains (e.g., DNA binding domain of steroid receptors), wherein one or more conserved domains are substantially removed to decrease non-specific binding of a probe containing FPC nucleic acid molecules specific for the RNA target sequence.

As described above, repetitive nucleic acid sequences are present in some target nucleic acid sequences (e.g., genomic target nucleic acid sequences), and are substantially (or even completely) removed from such target sequences to generate a population of binding regions used to generate the disclosed FPC nucleic acid molecules and probes. Repetitive nucleic acid sequences (or repetitive elements) are known in the art. Major classes of interspersed repetitive nucleic acid sequences in the human genome include Alu and Line (L1) repeats. Alu repeats are the most abundant interspersed repetitive nucleic acid sequence in the human genome with a total copy number of approximately 1 million. The Alu sequence is approximately 300 base pairs in length and occurs with an average frequency of once every 3300 base pairs. They occur throughout the primate family and are homologous to a small, abundant RNA gene that codes for the 300-nucleotide-long RNA molecule known as 7SL. L1 repetitive nucleic acid sequences are interspersed repeat sequences of between 1000 and 7000 base pairs. L1s have a common sequence at the 3' end, but are variably shortened at the 5' end (accounting for the disparity in length). They occur on average every 28,000 base pairs in the human genome, for a total copy number of about 100,000. Unlike Alu repetitive nucleic acid sequences, which are restricted to primates, L1 repetitive nucleic acid sequences are found in most other mammalian species.

Microsatellite repeats include a variety of simple di-, tri-, tetra-, and penta-nucleotide tandem repeats that are dispersed in the euchromatic arms of most chromosomes. The dinucleotide repeat (GT)n is the most common of these dispersed repetitive nucleic acid sequences, occurring on average every 30,000 bases in the human genome, for a total copy number of 100,000. The GT repeats range in size from about 20 to 60 base pairs and appear in most eukaryotic genomes. Minisatellite repeats are a class of dispersed tandem repeats in which the repeating unit is 30 to 35 base pairs in length and has a variable sequence, but contains a core sequence 10 to 15 base pairs in length. Minisatellite repeats range in size from 200 base pairs up to several thousand base pairs, and are present in lower copy numbers than microsatellite repeats. Minisatellite repeats tend to occur in greater numbers toward the telomeric ends of chromosomes.

Other repetitive nucleic acid sequences are predominantly limited to particular structures of the chromosome. Telomere repeats consist of tandem repeats of the sequence "TTAGGG" (SEQ ID NO: 359) and are located at the very ends of the linear DNA molecules in human and vertebrate chromosomes. Subtelomeric repeats include classes of repetitive sequences that are interspersed in the last 500,000 bases of nonrepetitive DNA located adjacent to the telomere. Some repetitive nucleic acid sequences are chromosome specific and others appear to be present near the ends of all human chromosomes.

Alpha satellite DNA is a family of related repetitive nucleic acid sequences that occur as long tandem arrays at the centromeric region of all human chromosomes. The repeat unit is about 340 base pairs, and appears as a dimer made up of two subunits, each about 170 base pairs long. Alpha satellite DNA occurs on both sides of the centromeric constriction and extends up to 5000 base pairs from the centromere.

Satellite I, II, and III repeats are the three classical human satellite DNAs. Satellite DNAs can be isolated from the bulk of genomic DNA by centrifugation in buoyant density gradients because their densities differ from the densities of other DNA sequences. Satellite I is rich in As and Ts and is composed of alternating arrays of a 17- and 25-base-pair repeating unit. Satellites II and III are both derived from the simple five-base repeating unit "ATTCC" (SEQ ID NO: 360). Satellite II is more highly diverged from the basic repeating unit than Satellite III. Satellites I, II and III occur as long tandem arrays in the heterochromatic regions of human chromosomes 1, 9, 16, 17, and Y and the satellite regions on the short (p) arms of human chromosomes 13, 14, 15, 21, and 22, $C_o$t-1™ DNA is a fraction of repetitive DNA that is separable from other genomic DNA based on faster re-annealing after melting to dissociate the two strands of the helix. The definition of $C_o$t-1™ DNA is based on the hybridization (or re-annealing) properties of the DNA rather than on sequence characteristics, and includes a mixed population of the specific repetitive elements discussed above.

In particular examples, the disclosed FPC nucleic acid molecules do not include appreciable amounts of undesired (e.g., repetitive) nucleic acid sequences (e.g., 20, 22, 24 of FIG. 1A), including, for example, any of the classes expressly listed above.

Detectable Labels

The disclosed FPC nucleic acid molecules can include one or more labels, for example to permit detection of a target nucleic acid molecule using the disclosed probes. In various applications, such as in situ hybridization procedures, a FPC nucleic acid molecule includes a label (e.g., a detectable label). A "detectable label" is a molecule or material that can be used to produce a detectable signal that indicates the presence or concentration of the probe (particularly the bound or hybridized probe) in a sample. Thus, a labeled FPC nucleic acid molecule provides an indicator of the presence or concentration of a target nucleic acid sequence (e.g., genomic target nucleic acid sequence) (to which the labeled FPC nucleic acid molecule is bound or hybridized) in a sample. The disclosure is not limited to the use of particular labels, although examples are provided.

A label associated with a FPC nucleic acid molecule can be detected either directly or indirectly. A label can be detected by any known or yet to be a discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Invitrogen, e.g., see, *The Handbook—A Guide to Fluorescent Probes and Labeling Technologies*, Invitrogen Detection Technologies, Molecular Probes, Eugene, Oreg.). Examples of particular fluorophores that can be attached (for example, chemically conjugated) to a FPC nucleic acid molecule are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Invitrogen Detection Technologies, Molecular Probes (Eugene, Oreg.) and including the ALEXA FLUOR® series of dyes (for example, as described in U.S. Pat. Nos. 5,696,157, 6,130, 101 and 6, 716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from QuantumDot Corp, Invitrogen Nanocrystal Technologies, Eugene, Oreg.; see also, U.S. Pat. Nos. 6,815,064, 6,682,596 and 6,649,138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals that can be coupled to a variety of biological molecules (including dNTPs and/or nucleic acids) or substrates by techniques described in, for example, Bruchez et. al. (1998) *Science* 281:2013-6, Chan et al. (1998) *Science* 281:2016-8, and U.S. Pat. No. 6,274,323.

Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299 (published May 27, 1999). Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Invitrogen.

Additional labels include, for example, radioisotopes (such as $^3$H), metal chelates such as DOTA and DPTA chelates of radioactive or paramagnetic metal ions like $Gd^{3+}$, and liposomes.

Detectable labels that can be used with the disclosed FPC nucleic acid molecules also include enzymes, for example horseradish peroxidase, alkaline phosphatase, acid phosphatase, glucose oxidase, β-galactosidase, β-glucuronidase or β-lactamase. Where the detectable label includes an enzyme, a chromogen, fluorogenic compound, or luminogenic compound can be used in combination with the enzyme to generate a detectable signal (numerous of such compounds are commercially available, for example, from Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate](ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. For example, SISH procedures involve metallographic detection schemes for identification and localization of a hybridized genomic target nucleic acid sequence. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods include using an oxido-reductase enzyme (such as horseradish peroxidase) along with a water soluble metal ion, an oxidizing agent and a reducing agent, again to for form a detectable precipitate. (See, for example, U.S. Pat. No. 6,670,113).

In non-limiting examples described below, FPC nucleic acid molecules are labeled with dNTPs covalently attached to hapten molecules (such as a nitro-aromatic compound (e.g., dinitrophenyl (DNP)), biotin, fluorescein, digoxigenin, etc.). Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955. Indeed, numerous labeled dNTPs are available commercially, for example from Invitrogen Detection Technologies (Molecular Probes, Eugene, Oreg.). A label can be directly or indirectly attached of a dNTP at any location on the dNTP, such as a phosphate (e.g., $\alpha$, $\beta$ or $\gamma$ phosphate) or a sugar. Detection of labeled FPC nucleic acid molecules can be accomplished by contacting the hapten-labeled FPC nucleic acid molecules bound to the genomic target sequence with a primary anti-hapten antibody. In one example, the primary anti-hapten antibody (such as a mouse anti-hapten antibody) is directly labeled with an enzyme. In another example, a secondary anti-antibody (such as a goat anti-mouse IgG antibody) conjugated to an enzyme is used for signal amplification. In CISH a chromogenic substrate is added, for SISH, silver ions and other reagents as outlined in the referenced patents/applications are added.

A detectable label can be incorporated into FPC nucleic acid molecules by conjugating the detectable label to a dNTP, which is incorporated into the FPC nucleic acid molecule. Incorporation of labeled dNTPs into FPC nucleic acid molecules is discussed in more detail with respect to the methods for generating probes.

METHODS FOR PRODUCING PROBES

Methods of producing the disclosed probes that include a population of FPC nucleic acid molecules are provided herein. Although exemplary methods are provided, the disclosure is not limited to these particular methods. An overview of methods that can be used to generate the disclosed probes is provided in FIGS. 1A, 1B and 3. Briefly, as shown in FIG. 1A, a target nucleic acid molecule (e.g., genomic target nucleic acid molecule) 10, 40 is selected. If the target nucleic acid molecule (e.g., genomic target nucleic acid molecule) 10, 40 has or is thought to have undesired nucleic acid sequences (such as, sequences that may lead to increased background signal from a probe, including repetitive sequences, homologous sequences, sequences encoding conserved domains) (e.g., 20, 22, 24), such nucleic acid sequences are identified and substantially removed. However, if the target nucleic acid molecule (e.g., viral genomic target nucleic acid molecule or RNA target nucleic acid molecule) 40 does not have (or does not have a significant amount of) background-producing nucleic acid sequences, this step can be omitted. This target nucleic acid molecule 10, 40 is used in step 60 to generate a population of binding regions 100, which is substantially free of background-producing (or other undesirable) (e.g., repetitive) nucleic acid sequences 20, 22, 24. In some examples, at least 80% (such as at least 90% or at least 98%) of the background-producing (or other undesirable) (e.g., repetitive) nucleic acid sequences 20, 22, 24 are removed from the target nucleic acid molecule.

The binding regions 114, 116, 118 in the population of binding regions are ligated 250. The binding regions 114, 116, 118 can be ligated directly, or include linkers between the binding regions 114, 116, 118. Optionally, binding regions 114, 116, 118 can be subjected to one or more amplification reactions 200 prior to ligation 250. Ligation of the binding regions 114, 116, 118 produces probe 300 that includes a population (such as a heterogeneous population) of FPC nucleic acid molecules 310, 312, 314, 316, 318, 320, 322, 324, 326, 328, 330, 332.

Figure 3:
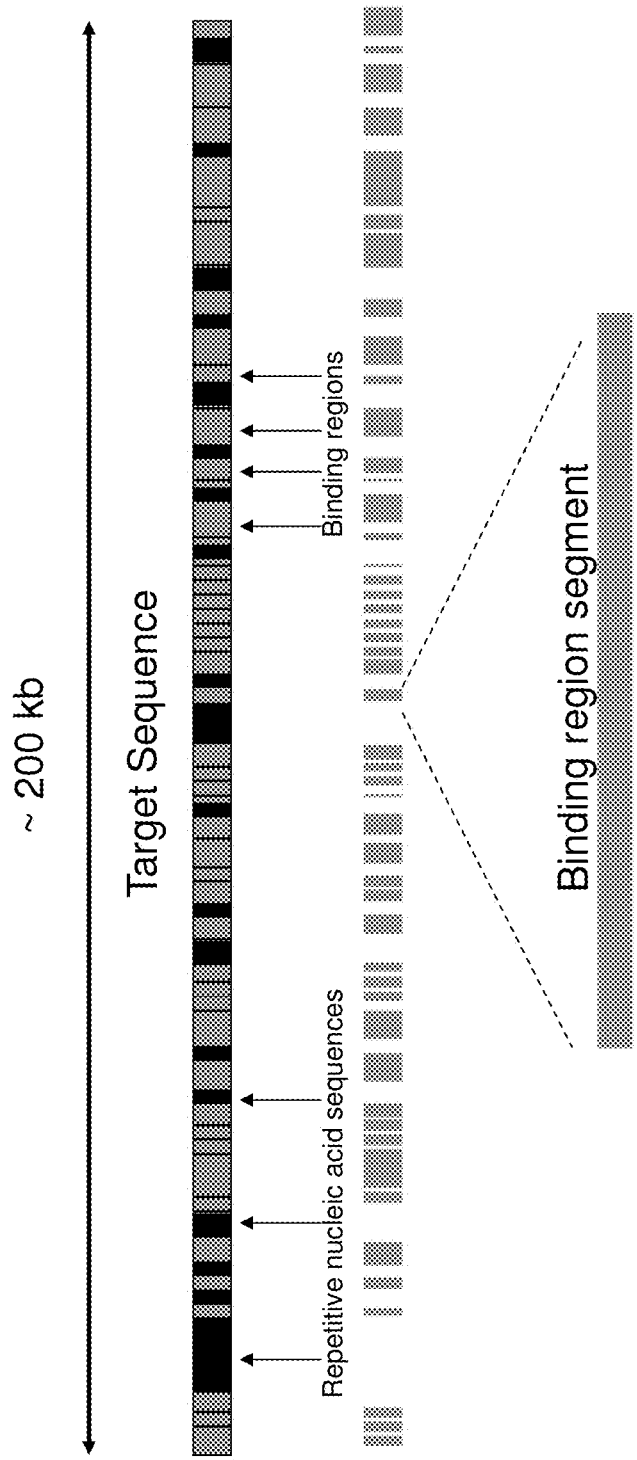
FIG. 3 is a schematic illustration showing exemplary undesired nucleic acid sequences (e.g., repetitive nucleic acid sequences found in mammalian genomic target nucleic acid sequences) and binding regions corresponding to a target nucleic acid sequence (e.g., genomic target nucleic acid sequence). In the example shown, the target nucleic acid sequence spans approximately 200 kb. Interspersed undesired nucleic acid sequences are shown in black, and unique (e.g., per haploid genome) binding regions are shown in grey.
Figure 6A:
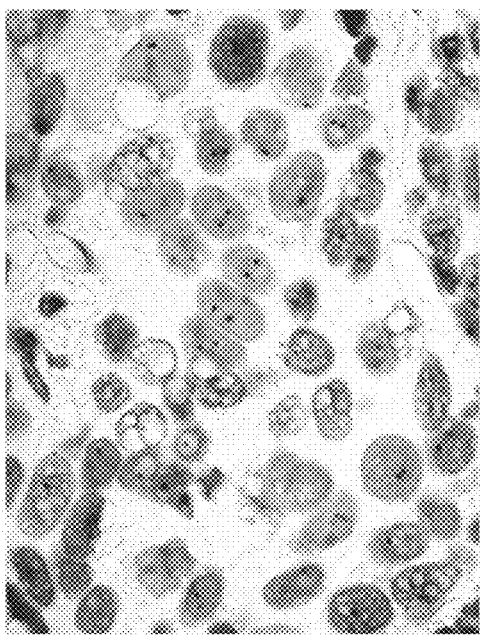
FIGS. 6A-D are digital images showing hybridization of an exemplary HER2FPC nucleic acid probe to fixed tissue samples.
Figure 6B:
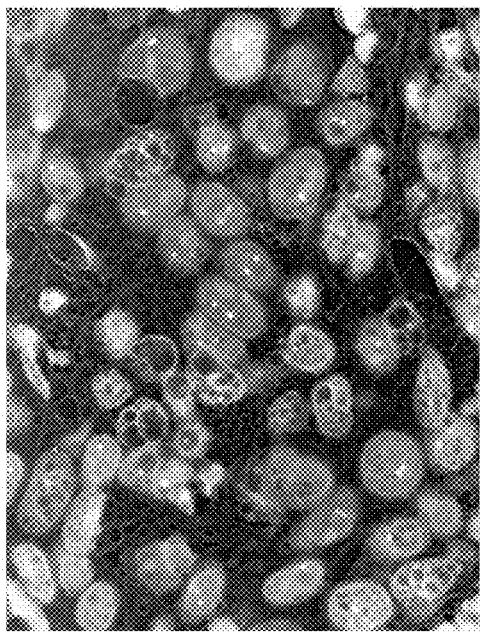
Figure 6C:
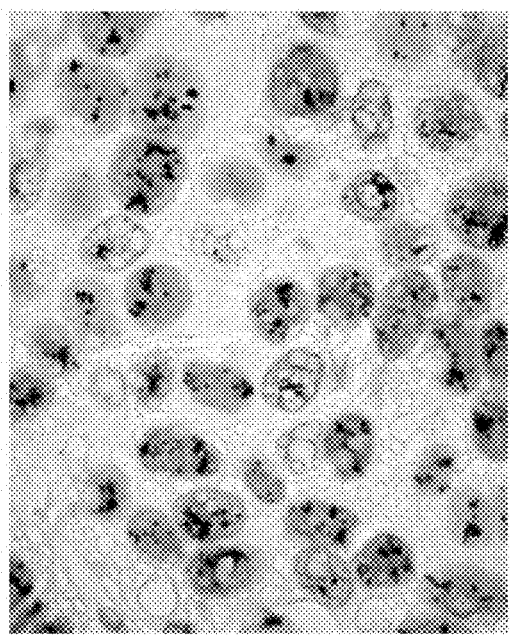
Figure 6D:
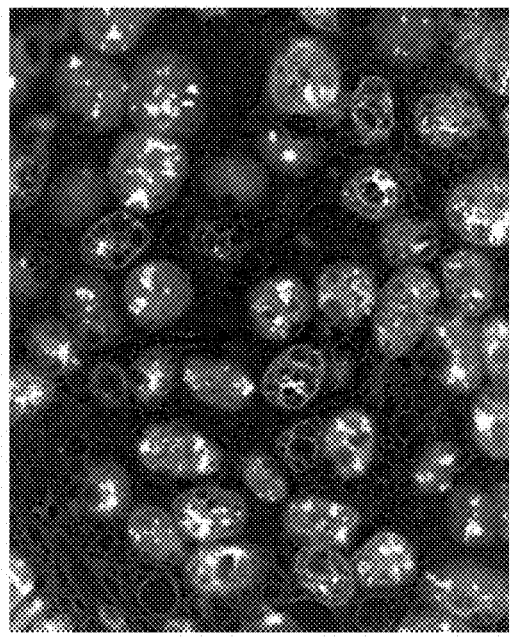

FIG. 3 shows a target nucleic acid sequence (e.g., genomic target nucleic acid molecule) containing unique binding regions (grey regions) and repetitive or other undesirable nucleic acid sequence (black regions). The unique binding regions are isolated (e.g., amplified) from the target nucleic acid sequence (e.g., genomic target nucleic acid sequence), resulting in a population of individual binding regions, which correspond to the target nucleic acid sequence. The individual binding regions are then ligated, resulting in the production of FPC nucleic acid molecules.

Identification of Undesired Nucleic Acid Sequences in a Target Nucleic Acid Sequence As discussed above, some target nucleic acid sequences useful for the disclosed probes and methods will contain repetitive or other undesired nucleic acid elements (e.g., genomic target nucleic acid sequences). In those embodiments, nucleic acid probes that are substantially (e.g., entirely) free of undesired sequences and include a population (e.g., heterogeneous population) of FPC nucleic acid molecules can be produced by amplifying one, or more than one (that is, a plurality) binding regions of a target nucleic acid sequence (e.g., genomic target nucleic acid sequence) to produce a population of binding regions (e.g., 100, 140 of FIG. 1A). As discussed above, some exemplary FPC nucleic acid molecules include a plurality of contiguous binding regions, are substantially free of repetitive or other undesired nucleic acid sequences, and correspond to a target sequence. FIGS. 1A, 1B, and 3 schematically illustrate the production of populations of binding regions that are substantially free of repetitive nucleic acid sequences, and their assembly into a population of FPC nucleic acid molecules. As discussed above, a FPC nucleic acid molecule is a nucleic acid that includes two or more binding regions that correspond to a target nucleic acid sequence (e.g., genomic target nucleic acid sequence). The individual binding regions can be arranged in the FPC nucleic acid molecule in an order and/or orientation that differs from that of the target nucleic acid sequence (e.g., genomic target nucleic acid sequence).

Repeat-free (that is substantially, such as entirely repeat-free) binding region segments (or segments free or substantially free of other undesired nucleic acid sequence) that correspond to a selected target nucleic acid sequence (as discussed above) can be identified and/or isolated and/or produced by any of a variety of methods. So long as the binding regions do not contain appreciable repetitive (or other undesired) nucleic acid sequence, any method for generating a population of binding regions corresponding to a target nucleic acid molecule (e.g., genomic target nucleic acid molecule) is suitable for use in these methods.

In one example, the substantially or completely repetitive (or other undesirable, e.g., background-producing) nucleic acid-free binding regions corresponding to the target nucleic acid molecule (e.g., genomic target nucleic acid molecule) are identified using a computer implemented algorithm. Computer implemented algorithms or programs for identifying undesired (e.g., repetitive) nucleic acid elements and "removing" them from a sequence represented in a database are well known in the art (see, e.g., Queen and Korn, *Nucleic Acids Res.* 12:581-599, 1984).

For example, RepeatMasker is a program that searches established databases using the alignment program Cross-Match to identify and "mask" repetitive nucleic acid elements. Similarly, the MaskerAid program, which substitutes the WU-BLAST search algorithm in the context of Repeat-Masker, can be used. Alternative programs include, for example, FORRepeats (Lefebvre et al., *Bioinformatics* 19: 319-326, 2003), MUMmer (Delcher et al., *Nucleic Acids Res.* 27:2369-2376, 1999) and REPuter (Kurtz et al., *Nucleic Acids Res.* 29:4633-42, 2001) also can be used to identify repetitive nucleic acid elements within a target nucleic acid molecule (e.g., genomic target nucleic acid molecule).

It will be appreciated that the processes implemented by the computer to identify and eliminate undesired (e.g., repetitive) nucleic acid sequences can be performed manually without the assistance of a computer. However, because large expanses (often exceeding 100 kb) of RNA or DNA are frequently evaluated as target nucleic acid molecules (e.g., genomic target nucleic acid molecule), manual examination of a sequence can be time-consuming and difficult. In addition, because multiple classes of undesired (e.g., repetitive) nucleic acid molecules can be present in a target nucleic acid molecule (e.g., genomic target nucleic acid molecule) and because a certain amount of variability exists within the various classes of undesired (e.g., repetitive) nucleic acid molecules, manual examination may be less accurate and comprehensive than computer assisted procedures. In addition, binding regions that are substantially or completely free of undesired (e.g., repetitive) nucleic acid sequence can be ascertained by reviewing a preexisting database containing sequence information pertaining to previously screened target nucleic acid molecule (e.g., genomic target nucleic acid molecule) (e.g., sequence information obtained via MaskerAid or other computer implemented programs).

Generation of Binding Regions Substantially Free of Undesired Nucleic Acid Sequence Once identified, the binding regions that are substantially or completely free of repetitive (or other undesirable, e.g., background-producing) nucleic acid sequences of a target nucleic acid molecule (e.g., genomic target nucleic acid molecule) can be generated using known methods. For example, binding regions can be amplified from a target nucleic acid molecule, obtained from the target nucleic acid molecule by subtractive hybridization, isolated from a target nucleic acid molecule or combinations thereof. In some examples, the target nucleic acid molecule is present in its native form, or is part of a vector that includes the target sequence.

In one example, binding regions are amplified from a target nucleic acid sequence (for example, by amplification in a polymerase chain reaction, or PCR). Essentially any amplification method known in the art can be used to amplify binding regions that are substantially or completely free of repetitive (or other undesirable, e.g., background-producing) nucleic acid sequences. In some examples, multiple amplification reactions are performed. If desired, the resulting binding region amplicons can be diluted prior to subsequent amplification.

An example of amplification is the polymerase chain reaction (PCR), in which a biological sample (such as one containing genomic nucleic acid molecules, for example a chromosomal preparation) is contacted with a pair of oligonucleotide primers, under conditions that allow hybridization of the primers to a nucleic acid template in the sample. The primers are extended under suitable conditions, dissociated from the template, and then re-annealed, extended, and dissociated to amplify the number of copies of the nucleic acid. Numerous procedures for PCR are known in the art and exemplary protocols can be found, e.g., in Sambrook and Russell., *Molecular Cloning: A Laboratory Manual*, Cold Spring Harbor Laboratory Press, Cold Spring Harbor, N.Y., 2001; and Ausubel et al., *Short Protocols in Molecular Biology*, 4$^{th}$ ed., John Wiley & Sons, Inc., 1999.

Amplification of binding region segments that correspond to a target nucleic acid sequence (e.g., genomic target nucleic acid sequence) can be accomplished using the polymerase chain reaction (PCR), which is described in detail in U.S. Pat. Nos. 4,683,195, 4,683,202, and 4,800,159, and in *PCR Protocols A Guide to Methods and Applications*, Innis et al., eds., Academic Press Inc., San Diego, Calif., 1990, (see also, Sambrook, Ausubel). PCR utilizes pairs of primers having sequences complimentary to opposite strands of target nucleic acids (such as a genomic target nucleic acid sequence), and positioned such that the primers are converging. The primers are incubated with template nucleic acid under conditions that permit selective hybridization. Primers can be provided in double-stranded or single-stranded form. If the genomic target nucleic acid sequence(s) is present in a sample, the primers will hybridize to form a nucleic-acid: primer complex. An excess of deoxynucleoside triphosphates (dNTPs) is added, along with a thermostable DNA polymerase, e.g., Taq polymerase. If the target:primer complex has been formed, the polymerase will extend the primer along the target genomic sequence by adding nucleotides. After polymerization, the newly-synthesized strand of DNA is dissociated from its complimentary target (template) strand by raising the temperature of the reaction mixture. When the temperature is subsequently lowered, new primers will bind to each of these two nucleic acid strands, and the process is repeated. Multiple cycles of raising and lowering the temperature are conducted, with a round of replication in each cycle, until a sufficient amount of amplification product is produced. Variants of PCR, such as DOP-PCR (Feher et al., *Diagn. Mol. Pathol.* 15:43-48, 2006); repair chain reaction (as disclosed in WO 90/01069); rapid amplification methods as described in U.S. Pat. No. 6,638,722; T7 based linear amplification (e.g., as in Liu et al., *BMC Genomics* 4:19 pp 1-11, 2003) are also suitable for generating binding regions corresponding to a target nucleic acid sequence (e.g., genomic target nucleic acid sequence).

Alternatively, methods such as transcription-based amplification systems (TAS, for example see Kwoh et al., *Proc. Natl. Acad. Sci.* 86:1173-7, 1989), or NASBA (nucleic acid sequence based amplification; Malek et al., *Methods Mol. Biol.* 28:253-60, 1994; and U.S. Pat. No. 6,025,134) can be used to amplify portions of a target nucleic acid sequence (e.g., genomic target nucleic acid sequence). In these methods, the promoter sequence of a designated DNA-dependent RNA polymerase is added to the desired segment of the target sequence and amplified in multiple rounds of transcription by the appropriate RNA polymerase. Such isothermal reactions bypass the need for denaturing cDNA strands from their RNA templates by including RNAse H to degrade RNA hybridized to DNA. Other methods using isothermal amplification, including, e.g., methods described in U.S. Pat. No. 6,251,639, can also be employed in the context of the present disclosure.

Amplification can also be accomplished by use of the ligase chain reaction (LCR), disclosed in European Patent Application No. 320,308, or by the ligase detection reaction (LDR), disclosed in U.S. Pat. No. 4,883,750, or by gap filling ligase chain reaction amplification, as disclosed in U.S. Pat. No. 5,427,930. In LCR, two probe pairs are prepared, which are complimentary each other, and to adjacent sequences on both strands of the target nucleic acid sequence (e.g., genomic target nucleic acid sequence). Each pair will bind to opposite strands of the target sequence such that they are adjacent. Each of the two probe pairs can then be linked to form a single unit, using a thermostable ligase. By temperature cycling, as in PCR, bound ligated units dissociate from the target sequence (e.g., genomic target nucleic acid sequence), then both molecules can serve as "target sequences" for ligation of excess probe pairs, providing for an exponential amplification. The LDR is very similar to LCR. In this variation, oligonucleotides complimentary to only one strand of the genomic target sequence are used, resulting in a linear amplification of ligation products, since only the original target nucleic acid molecule can serve as a hybridization template. It is used following a PCR amplification of a target nucleic acid sequence in order to increase signal.

Additionally, isothermal methods of amplification can be used to amplify segments of a target nucleic acid sequence (e.g., genomic target nucleic acid sequence). Exemplary methods include: transcription-free isothermal amplification, as disclosed in U.S. Pat. No. 6,033,881; or isothermal transcription-based systems such as 3SR (Self-Sustained Sequence Replication; 1990; Mueller et al., *Histochem Cell Biol.* 108:4310437, 1997) strand displacement amplification (as disclosed in U.S. Pat. Nos. 5,648,211; 5,744,311; Walker et al., *Proc. Natl. Acad. Sci.* 89:392-396, 1992; Walker et al., *Nucleic Acids Res.* 20:1691-1696, 1992; Tsurumi et al., *Biochem. Biophys. Res. Commun.*, 238:33-38, 1997), loop-mediated isothermal amplification (Notomi et al., *Nucleic Acids Res.* 28:e63i-vii, 2000); rolling circle amplification (U.S. Pat. Nos. 5,648,245; 5,714,320; 6,218,152; 6,291,187; and Mikawa et al., *Nucleic Acids Res.* 34:e69 pp 1-9, 2006); isothermal amplification (as disclosed in U.S. Patent Publication No. 2005/0164213); sequence independent amplification (SIA) (for example see U.S. Pat. No. 5,731,171); and multiple strand displacement (MDA) as disclosed, e.g., in U.S. Pat. No. 6,323,009, and modifications thereof, as described in, e.g., Panelli et al., *BioTechniques* 39:174-180, 2005, as well as by Helicase-dependent amplification (HDA). HDA utilizes a DNA helicase to generate single-stranded templates for primer hybridization and subsequent primer extension by a DNA polymerase under isothermal conditions (Vincent et al., *EMBO Reports* 5:795-800, 2004).

In some examples, the amplification method used to produce substantially repetitive nucleic acid sequence-free binding regions, which correspond to a target nucleic acid sequence (e.g., genomic target nucleic acid sequence), is selected to generate a binding region amplification product that is relatively uniform in size and composition. Thus, for example, PCR is a suitable amplification method for generating binding regions that are free or substantially free of repetitive nucleic acid sequence. Primers are selected based on the location and sequence of the identified repetitive nucleic acid sequences.

Primers can be selected manually, or with the assistance of a computer implemented algorithm that optimizes primer selection based on desired parameters, such as annealing temperature, length, GC content, etc. Numerous computer implemented algorithms or programs for use via the internet or on a personal computer are available, for example at or from the indicated web address. A non-exclusive list of such programs (with corresponding Internet addresses) includes: CODEHOP (blocks.fhcrc.org/codehop.html); Gene Fisher (bibiserv.techfak.uni-bielefeld.de/genefisher/); DoPrimer (doprimer.interactiva.de/); Primer3 (genome.wi.mit.edu/cgi-bin/primer/primer3_www.cgi); Primer Selection (alces.med.umn.edu/rawprimer.html); Web Primer (genome-www2.stanford.edu/cgi-bin/SGD/web-primer); PCR Designer (cedar.genetics.soton.ac.uk/public_html/primer.html); Primo Pro 3.4 (changbioscience.com/primo/primo.html); Primo Degenerate 3.4 (changbioscience.com/primo/prmod.html); PCR Primer Design (pga.mgh.harvard.edu/servlet/org.mgh.proteome.Primer); The Primer Generator (med.jhu.edu/medcenter/primer/primer.cgi); EPRIMER3 (bioweb.pasteur.fr/seqanal/interfaces/eprimer3.html3); PRIMO (bioweb.pasteur.fr/seqanal/interfaces/primo.html3); PrimerQuest (idtdna.com/biotools/primer_quest/primer_quest.asp); MethPrimer (itsa.ucsf.edu/~urolab/methprimer/index 1.html); Rawprimer (alces.med.umn.edu/rawprimer.html); MEDUSA (cgr.ki.se/cgr/MEDUSA); The Primer Prim'er Project (nmr.cabm.rutgers.edu/bioinformatics/Primer_Primer_Project/Primer.html); Oligonucleotides for the PCR (cit2.fr/bio2/Oligo2lib.html); GAP (promoter.ics.uci.edu/Primers/); Oligonucleotides pour la PCR (cit2.fr./bio2/OligoTM.html); Oligonucleotide properties calculator (asic.nwu.edu/biotools/oligocalc.html); Oligonucleotide analyzer (mature.com/oligonucleotide.html); Oligo Tm Determination (alces.med.umn.edu/rawtm.html); Poland (biophys.uniduesseldorf.de/local/POLAND/poland.html); PROLIGO (gensetoligos.com/Calculation/calculation.html); PrimerSelect (dnastar.com); DNASIS Max (medprobe.com/no/dnasis.html); Primer Premier 5 (premier/biosoft.com/); Primer Premier (premier/biosoft.com/); NetPrimer (premierbiosoft.com/NetPrimer.html); Array Designer 2 (premierbiosoft.com/dnamicroarray/dnamicroarray.html); Beacon Designer 2.1 (premierbiosoft.com/molecular_beacons/taqman_molecular_beacons.html); GenomePRIDE 1.0 (pride.molgen.mpg.de/genomepride.html); Fast PCR (biocenter.helsinki.fi/bi/bare-1_html/manual.htm); OLIGO 6 (oligo.net/); Primer Designer 4 (scied.com/ses_pd5.htm); GPRIME (life.anu.edu.au/molecular/software/gprimer.htm); Sarani Gold (mail.standgenomics.cm/products/sarani/); PCR Help (techne.com/CatMol/pcrhelp.htm); Genorama chip Design Software (asperbio.com/Chip_design_soft.htm); Primer Designer (genamics.com/expression/primer.htm); Primer Premier (biotechniques.com/freesamples/itembtn21.html); and PrimerDesign (chemie.unimarburg.de/%7Ebecker/pdhome.html).

For example, to generate multiple binding regions from a target nucleic acid sequence (e.g., genomic target nucleic acid sequence), regions of sequence devoid of repetitive (or other undesirable, e.g., background-producing) nucleic acid sequence are identified, for example manually or by using a computer algorithm selected from among the programs indicated above (e.g., RepeatMasker, MaskerAid, PRIME). Within a target nucleic acid sequence (e.g., genomic target nucleic acid sequence) that spans several to several-hundred kilobases, typically numerous binding regions that are substantially or completely free of repetitive (or other undesirable, e.g., background-producing) nucleic acid sequences are identified. Unique sequence primers are then designed based on the sequence at (or towards) the ends of each binding region that is substantially or completely free of repetitive (or other undesirable, e.g., background-producing) nucleic acid sequence. For example, unique sequence primers can be selected that are complementary to sequences as close to the ends of a binding region that is substantially or completely free of repetitive (or other undesirable, e.g., background-producing) nucleic acid sequence as possible to maximize segment length. In some examples, internal primers are selected. To facilitate amplification of the individual binding regions, it can be convenient to select primer sequences that share annealing and amplification characteristics, (e.g., melting temperature or Tm), so that multiple binding regions can be amplified in tandem using the same reaction parameters. For example, the program PRIME can be used to select unique primer sequences complementary to binding regions that share a Tm and can be amplified in tandem using identical reaction parameters. Optionally, at least one of the primers includes a 5' phosphate to facilitate subsequent enzymatic ligation of the amplified binding regions. For example, if FPC nucleic acid molecules are desired that differ from the target nucleic acid sequence solely in order (but not orientation) a single primer (for example, complementary to the "top" strand) in each reaction incorporates a phosphate. If the binding regions are ligated without additional phosphorylation (e.g., enzymatic phosphorylation with a kinase), the resulting ligation proceeds in a single direction (for example, head to tail). If FPC nucleic acid molecules that differ both in order and orientation are desired, both "top" and "bottom" primers can incorporate a phosphate group, such that ligation can occur in a head to tail, head to head, or tail to tail direction.

Optionally, binding region primers can include an additional sequence at the 5' end of the primer that is designed to facilitate subsequent manipulation (e.g., ligation and/or subsequent amplification) of the resulting amplified binding region. Such additional sequences can include, for example, one or more restriction enzyme recognition sites, one or more "universal" primer sequences (such as commercially available T7 or T3 universal primers), or a fixed nucleotide sequence (such as an all purine or all pyrimidine tract) that can serve as a primer annealing site for subsequent amplification reactions. For example as shown in FIG. 4, an all purine oligonucleotide can be added to the 5' (that is, the non-priming) end of a unique sequence primer that is complementary to the 5' and/or 3' (top and/or bottom) strand(s) of a portion of a nucleic acid that is to be amplified (such as a binding region that is substantially or completely free of repetitive nucleic acid sequence, from a genomic target sequence). Commonly, the 5' end of one or both oligonucleotides is phosphorylated to facilitate subsequent ligation. Amplification with such primer(s) results in a product that includes an all purine tract at the terminus of one strand (and a pyrimidine tract on the complementary strand).

Alternatively, such sequences (e.g., restriction enzyme recognition sites, universal primers, purine or pyrimidine tracts, etc.), can be added following amplification by ligating duplexed DNA with the desired binding region to one or both ends of the amplified binding region. For example, an oligonucleotide consisting exclusively of purines (e.g., 5'-GAGGAG-3'; SEQ ID NO: 357) can be annealed to its reverse complement (e.g., 5'-CTCCTC-3'; SEQ ID NO: 358). Often, one or both of the oligonucleotides is phosphorylated at the 5' end to facilitate subsequent ligation. After annealing the two oligonucleotides together to form a double stranded oligonucleotide molecule, the duplexed oligonucleotide adapter or linker is ligated (typically, in an enzymatic or chemical ligation reaction) to one or both ends of the binding region. This process results in a binding region that includes a fixed sequence at one or both ends (for example, depending on whether one or both ends of the amplification product include a reactive phosphoryl group). When ligated together, binding regions with such fixed sequences at one or both ends produce a linear nucleic acid with intervening purine/pyrimidine stretches that can serve, for example, as primer binding sites (FIG. 5). Optionally (as shown in the non-limiting example described above) or alternatively, the linker/adapter can include a restriction enzyme recognition site.

While amplification is one exemplary method for providing binding regions from a target nucleic acid sequence (e.g., genomic target nucleic acid sequence), and can increase (e.g., geometrically increase) the quantity of binding region nucleic acids, other methods can also be used to provide binding regions that are substantially or completely free of repetitive (or other undesirable, e.g., background-producing) nucleic acid sequence in the context of producing the disclosed probes. For example, a target nucleic acid molecule can be digested with one or more restriction endonucleases (restriction enzymes). Following digestion with one or more restriction enzymes or other endonucleases, the specific (e.g., predetermined or selected) binding regions that are substantially or completely free of repetitive (or other undesirable, e.g., background-producing) nucleic acid sequence can be recovered. Methods for digesting nucleic acids are well known in the art, and exemplary methods sufficient to guide those of skill in the art are found, e.g., in Sambrook and Ausubel.

Repetitive (or other undesirable, e.g., background-producing) elements in a target nucleic acid sequence (e.g., genomic target nucleic acid sequence) can be removed in a number of different ways. For example, undesired nucleic acid molecules can be fragmented into small pieces with a restriction endonuclease that cuts frequently within the undesired nucleic acid sequence, but not (or less frequently) in the unique desired nucleic acid sequence. The resulting mixture of fragments can be size fractionated on an agarose gel according to established procedures, and only the larger desired elements selected as fragments for ligation into FPC nucleic acid molecules (which can serve as amplification templates). Undesired (e.g., background-producing) elements can be removed by enzymatically or physically (mechanically shearing, e.g., by sonication) cleaving the DNA into pieces, denaturing the duplex DNA into single strands by heating (for example, to 100° C. for 10 minutes) or alkali treatment (0.1 volume 3.0 M NaOH, 10-30 minutes at room temperature), and reannealing under controlled conditions. Because repetitive (or other undesirable, e.g., background-producing) nucleic acid sequence reanneals more rapidly than unique nucleic acid sequence, the faster annealing repetitive (or other undesirable, e.g., background-producing) nucleic acid sequence (or $C_o t$-1™ fraction) can be separated from the unique nucleic acid sequence by contacting the partially reannealed mixture with hydroxyapatite (e.g., in a column). Double stranded (rapidly reannealing) repetitive (or other undesirable, e.g., background-producing) nucleic acid sequence is retained by the column whereas the single stranded desired sequences remain unbound.

Binding regions that are substantially or completely free of undesirable (e.g., background-producing) nucleic acid sequence can also be prepared from a fragmented target nucleic acid sequence (e.g., genomic target nucleic acid sequence) by subtractive hybridization. In such a method, the target nucleic acid sequence (e.g., genomic target nucleic acid sequence) is denatured (if in double-stranded form), and the resulting single-stranded target nucleic acid molecules hybridized with labeled undesired (e.g., repetitive) nucleic acid molecules (e.g., $C_o$t-1™ DNA, or specific repetitive nucleic acid sequence, such as ALU, LINE, etc.). The resulting hybridized double-stranded labeled nucleic acid can then be removed using a specific binding partner that binds to the label. Additional details are provided, e.g., in U.S. Pat. Nos. 5,643,761, 6,569,621, and in Davison et al., *Am. J. Pathol.* 153:1401-1409, 1998. For example, repetitive (or other undesirable, e.g., background-producing) nucleic acid sequence can be removed from a sample of target nucleic acid molecule fragments by heat denaturing the target nucleic acid molecules and mixing with an excess of subtractor nucleic acid molecule (such as $C_o$t-1™ DNA) labeled with a hapten such as biotin, digoxygenin or DNP. The target and labeled subtractor nucleic acid molecules are permitted to anneal, during which period the subtractor nucleic acid molecules hybridize to the repetitive (or other undesirable, e.g., background-producing) nucleic acid elements in the target nucleic acid sequence. The annealed repetitive (or other undesirable, e.g., background-producing) nucleic acid molecules can then removed by contacting the mixture to a matrix (such as a column, magnetic beads, etc.) conjugated with a specific binding partner for the particular hapten (e.g., avidin, streptavidin for biotin, antibodies specific for digoxygenin or DNP). The repetitive (or other undesirable, e.g., background-producing) nucleic acid molecules are retained on the matrix, whereas the at least substantially undesired nucleic acid-free (e.g., repeat-depleted) nucleic acid binding regions remain in solution and can be recovered for further processing.

Any of these, or other, methods for producing binding regions of a target nucleic acid molecule (e.g., genomic target nucleic acid molecule) that are substantially (or completely) free of undesired sequences (e.g., repetitive nucleic acid sequences) can be used alone or in combination to prepare binding regions for production of FPC nucleic acid molecules. For example, additional exemplary methods are provided in U.S. Appl. Publ. No. 2006/0160116 as well as U.S. Pat. No. 6,280,929. It will be appreciated by those of skill in the art that if a linker/adapter or other specified nucleotide sequence is desired at the end of the binding regions, the sequence (such as a all purine/all pyrimidine duplex) can be ligated to one or both ends of the binding region as described above.

Ligating Binding Regions to Form FPC Nucleic Acid Molecules

The FPC nucleic acid molecules (which can serve as templates for further amplification) are assembled by ligating individual binding regions (for example present in a population of binding regions) that correspond to the selected target nucleic acid sequence (e.g., genomic target sequence). The term "ligate" (or "ligated" or "ligating") is used herein to indicate that two binding region nucleic acid segments or sequences are joined together to form a contiguous linear FPC nucleic acid molecule. However, linkers can be present between the binding region segments. Typically, two binding regions are joined enzymatically by a ligase in a ligation reaction. However, two binding regions can also be joined chemically (e.g., by incorporating appropriate modified nucleotides, as described in Dolinnaya et al., *Nucleic Acids Res.* 16:3721-38, 1988; Mattes and Seitz, *Chem. Commun.* 2050-2051, 2001; Mattes and Seitz, *Agnew. Chem. Int.* 40:3178-81, 2001; Ficht et al., *J. Am. Chem. Soc.* 126:9970-81, 2004. Alternatively, two different binding regions can be joined in an amplification reaction, or using a recombinase. For example, the binding regions that are substantially free of repetitive (or other undesirable, e.g., background-producing) nucleic acid sequences can be incubated in a mixture containing a bacterial or bacteriophage-encoded DNA ligase, such as T4 DNA ligase and ATP, in a suitable buffer, and incubated at a suitable temperature for a sufficient period of time for ligation to proceed. The time and temperature are typically optimized depending on whether the binding regions to be ligated are blunt ended or possess compatible overhangs (for example, produced by digestion with a restriction endonuclease or by attaching overhanging linker/adapter oligonucleotides). Therefore, both blunt-end and overlapping ligation reactions can be used to produce FPC nucleic acid molecules. Details regarding enzymatic ligation sufficient to guide one of skill in the art can be found, e.g., in Sambrook and Ausubel.

Ligation is dependent on the presence of 5' phosphoryl and 3' hydroxyl groups at the adjacent termini of the binding region molecules to be joined. Thus, the orientation of ligation can be predetermined by mixing binding regions with only one 5' phosphoryl group. In the manufacture of probes disclosed herein, the binding regions can be joined in a manner that is different in order, different in orientation, or both order and orientation, from the genomic target sequence to which the segments correspond. By mixing binding regions that are all phosphorylated at the 5' terminus of the "top" strand, the orientation can be fixed in the same orientation as the genomic target nucleic acid sequence. This can be accomplished by incorporating a 5' phosphoryl group into the primer prior to amplification. If FPC nucleic acid molecules that differ in both order and orientation from the genomic target sequence are desired, both 5' (top) and 3' (bottom) strand amplification primers can be phosphorylated. Alternatively, the amplified binding regions can be phosphorylated enzymatically (e.g., with a kinase) or chemically, prior to mixing with each other and the ligase. Similarly, linkers can be phosphorylated prior to addition to the ends of binding regions desired. Typically, binding regions isolated following restriction or other endonuclease digestion or mechanical shearing possess phosphoryl groups and do not require additional processing, although phosphorylation can be performed to assure complete and efficient ligation.

Amplifying FPC Nucleic Acid Molecules

The resulting FPC nucleic acid molecules can be used as a probe (for example by labeling the FPC nucleic acid molecules), and can serve as templates for amplification. For example, FPC nucleic acid molecule templates can be amplified in one or more reactions (for example, in a series of sequential reactions) to produce a population of FPC nucleic acid amplicons that are suitable as probes. The number of reactions is typically determined by the quantity of probe desired, thus for a single application, one amplification reaction may be sufficient. In contrast, where multiple samples are to be assayed, multiple assays are to be performed, or the assays are to be performed in an automated or semi-automated process, it can be desirable to perform several sequential amplification reactions to increase the yield of FPC nucleic acid molecule amplicons.

Any of the amplification procedures described above or known in the art can be adapted for use by those of skill in the art for the production of amplified FPC nucleic acid molecules from template FPC nucleic acid molecules. In particular examples, isothermal amplification reactions are employed. As discussed above, isothermal amplification reactions include: transcription-free isothermal amplification, as disclosed in U.S. Pat. No. 6,033,881; or isothermal transcription-based systems such as 3SR (Self-Sustained Sequence Replication; 1990; Mueller et al., *Histochem Cell Biol.* 108:4310437, 1997) strand displacement amplification (as disclosed in U.S. Pat. Nos. 5,648,211; 5,744,311; Walker et al., *Proc. Natl. Acad. Sci.* 89:392-396, 1992; Walker et al.,

*Nucleic Acids Res.* 20:1691-1696, 1992; Tsurumi et al., *Biochem. Biophys. Res. Commun.*, 238:33-38, 1997), loop-mediated isothermal amplification (Notomi et al., *Nucleic Acids Res.* 28:e63i-vii, 2000); rolling circle amplification (U.S. Pat. Nos. 5,648,245; 5,714,320; 6,218,152; 6,291,187; and Mikawa et al., *Nucleic Acids Res.* 34:e69 pp 1-9, 2006); isothermal amplification (as disclosed in U.S. Patent Publication No. 2005/0164213); and multiple strand displacement (MDA) as disclosed, e.g., in U.S. Pat. No. 6,323,009, and modifications thereof, as described in, e.g., Panelli et al., *BioTechniques* 39:174-180, 2005, as well as by helicase-dependent amplification (HDA). HDA utilizes a DNA helicase to generate single-stranded templates for primer hybridization and subsequent primer extension by a DNA polymerase under isothermal conditions (Vincent et al., *EMBO Reports* 5:795-800, 2004).

For example, isothermal amplification reactions can be employed using random hexamer primers. The random hexamers bind to their complementary sequence dispersed throughout the template FPC nucleic acid molecule. The annealed hexamer is then extended to form a FPC nucleic acid amplicon complementary to the template FPC nucleic acid molecule. This process is repeated along the length of the template FPC nucleic acid molecule and on the many product strands, resulting in amplification of the template FPC nucleic acid molecules. Amplification by this method generates overlapping FPC nucleic acid amplicon molecules that span the entire length of the template FPC nucleic acid molecule. Because the size of the template FPC nucleic acid molecule can exceed that generally amenable or practicable to methods such as PCR that rely on specific primers, and because the order and orientation of the segments is variable (and typically unpredictable without laborious analysis), isothermal amplification methods, which are highly processive, may yield better results. In certain embodiments, for example, where a fixed sequence has been incorporated into the binding region(s) (for example, by attachment of a linker/adapter or by incorporation of a linker into the primer used to amplify the binding region), primers that hybridize with the fixed sequence (or its complement) can also be used.

Labeling of Nucleic Acid Molecules

In some examples, the amplified FPC nucleic acid molecules are labeled. Labeling of the FPC nucleic acid molecules can be performed before, during or after amplification of FPC nucleic acid molecule templates. For example, the FPC nucleic acid molecules can be labeled "before" synthesis by incorporating one or more labeled nucleotides into the primer used for amplification of the FPC nucleic acid molecules. Labeled nucleotides can also be incorporated during amplification by including one or more labeled nucleotides in the amplification (e.g., multiple displacement amplification) reaction mixture. In some examples, a probe is labeled by incorporating one or more labeled dNTPs using an enzymatic (polymerization) reaction following amplification of the FPC nucleic acid molecules. For example, the amplified nucleic acid probe can be labeled by nick translation (using, for example, Bio-11-dUTP, 2,4-dinitro phenol, digoxin, etc.), by random primer extension with (e.g., 3' end tailing).

Enzymatic labeling procedures can be used to produce labeled probes. Chemical labeling procedures can also be employed. Numerous reagents (including hapten, fluorophore, and other labeled nucleotides) and other kits are commercially available for enzymatic labeling of nucleic acids including the primers and amplified FPC nucleic acid molecules (and if desired template FPC nucleic acid molecules). As will be apparent to those of skill in the art, any of the labels and detection procedures disclosed in the sections above are applicable in the context of labeling a probe, e.g., for use in in situ hybridization reactions. For example, the Amersham MULTIPRIME® DNA labeling system, various specific reagents and kits available from Invitrogen Detection Technologies (Molecular Probes, Eugene, Oreg.) or any other similar reagents or kits can be used to label the nucleic acids disclosed herein. In particular examples, FPC nucleic acid molecules (including FPC nucleic acid molecule amplicons) can be directly or indirectly labeled with a hapten, a ligand, a fluorescent moiety (e.g., a fluorophore or a semiconductor nanocrystal), a chromogenic moiety, or a radioisotope. For example, for indirect labeling, the label can be attached to FPC nucleic acid molecules via a linker (e.g., PEG or biotin).

Additional methods that can be used to label FPC nucleic acid molecules are provided in U.S. Application Pub. No. 2005/0158770.

METHODS OF USING PROBES

The disclosed probes, which include a plurality of FPC nucleic acid molecules (or fragments thereof), can be used for nucleic acid detection, such as in situ hybridization procedures (e.g., fluorescence in situ hybridization (FISH), chromogenic in situ hybridization (CISH) and silver in situ hybridization (SISH)). Hybridization between complementary nucleic acid molecules is mediated via hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. If a nucleotide unit at a certain position of a probe of the present disclosure is capable of hydrogen bonding with a nucleotide unit at the same position of a DNA or RNA molecule (e.g., a target nucleic acid sequence) then the oligonucleotides are complementary to each other at that position. The probe and the DNA or RNA are complementary to each other when a sufficient number of corresponding positions in each molecule are occupied by nucleotide units which can hydrogen bond with each other, and thus produce detectable binding. A probe need not be 100% complementary to its target nucleic acid sequence (e.g., genomic target nucleic acid sequence) to be specifically hybridizable. However sufficient complementarity is needed so that the probe binds, duplexes, or hybridizes only or substantially only to a target nucleic acid sequence when that sequence is present in a complex mixture (e.g., total cellular DNA or RNA).

In situ hybridization involves contacting a sample containing target nucleic acid sequence (e.g., genomic target nucleic acid sequence) in the context of a metaphase or interphase chromosome preparation (such as a cell or tissue sample mounted on a slide) with a labeled probe specifically hybridizable or specific for the target nucleic acid sequence (e.g., genomic target nucleic acid sequence). The slides are optionally pretreated, e.g., to remove paraffin or other materials that can interfere with uniform hybridization. The chromosome sample and the probe are both treated, for example by heating to denature the double stranded nucleic acids. The probe (formulated in a suitable hybridization buffer) and the sample are combined, under conditions and for sufficient time to permit hybridization to occur (typically to reach equilibrium). The chromosome preparation is washed to remove excess probe, and detection of specific labeling of the chromosome target is performed using standard techniques.

For example, a biotinylated probe can be detected using fluorescein-labeled avidin or avidin-alkaline phosphatase. For fluorochrome detection, the fluorochrome can be detected directly, or the samples can be incubated, for example, with fluorescein isothiocyanate (FITC)-conjugated avidin DCS. Amplification of the FITC signal can be effected, if necessary, by incubation with biotinconjugated goat anti-avidin D antibodies, washing and a second incubation with FITC-conjugated avidin. For detection by enzyme activity, samples can be incubated, for example, with streptavidin, washed, incubated with biotin-conjugated alkaline phosphatase, washed again and pre-equilibrated (e.g., in alkaline phosphatase (AP) buffer). The enzyme reaction can be performed in, for example, AP buffer containing nitroblue tetrazolium and 5' bromo-4-chloro-3-indoyl phosphate and stopped by incubation in 2×SSC. For a general description of in situ hybridization procedures, see, e.g., U.S. Pat. No. 4,888,278.

Numerous procedures for fluorescence in situ hybridization (FISH), chromogenic in situ hybridization (CISH) and silver in situ hybridization (SISH) are known in the art. For example, procedures for performing FISH are described in U.S. Pat. Nos. 5,447,841, 5,472,842, 5,427,932, and for example, in Pinkel et al., *Proc. Natl. Acad. Sci.* 83:2934-2938, 1986; Pinkel et al., *Proc. Natl. Acad. Sci.* 85:9138-9142, 1988, and Lichter et al., *Proc. Natl. Acad. Sci.* 85:9664-9668, 1988. CISH is described in, e.g., Tanner et al., *Am. J. Pathol.* 157:1467-1472, 2000, and U.S. Pat. No. 6,942,970. Additional detection methods are provided in U.S. Pat. No. 6,280,929. Exemplary procedures for detecting viruses by in situ hybridization can be found in Poddighe et al., *J. Clin. Pathol.* 49:M340-M344, 1996.

Numerous reagents and detection schemes can be employed in conjunction with FISH, CISH, and SISH procedures to improve sensitivity, resolution, or other desirable properties. As discussed above, probes labeled with fluorophores (including fluorescent dyes and QUANTUM DOTS®) can be directly optically detected when performing FISH. Alternatively, the probe can be labeled with a non-fluorescent molecule, such as a hapten (such as the following non-limiting examples: biotin, digoxygenin, DNP, and various oxazoles, pyrrazoles, thiazoles, nitroaryls, benzofurazans, triterpenes, ureas, thioureas, rotenones, coumarin, coumarin-based compounds, Podophyllotoxin, Podophyllotoxin-based compounds, and combinations thereof), ligand or other indirectly detectable moiety. Probes labeled with such non-fluorescent molecules (and the target nucleic acid sequences to which they bind) can then be detected by contacting the sample (e.g., the cell or tissue sample to which the probe is bound) with a labeled detection reagent, such as an antibody (or receptor, or other specific binding partner) specific for the chosen hapten or ligand. The detection reagent can be labeled with a fluorophore (e.g., QUANTUM DOT®) or with another indirectly detectable moiety, or can be contacted with one or more additional specific binding agents (e.g., secondary or specific antibodies), which can in turn be labeled with a fluorophore. Optionally, the detectable label is attached directly to the antibody, receptor (or other specific binding agent). Alternatively, the detectable label is attached to the binding agent via a linker, such as a hydrazide thiol linker, a polyethylene glycol linker, or any other flexible attachment moiety with comparable reactivities. For example, a specific binding agent, such as an antibody, a receptor (or other anti-ligand), avidin, or the like can be covalently modified with a fluorophore (or other label) via a heterobifunctional polyalkyleneglycol linker such as a heterobifunctional polyethyleneglycol (PEG) linker. A heterobifunctional linker combines two different reactive groups selected, e.g., from a carbonyl-reactive group, an amine-reactive group, a thiol-reactive group and a photo-reactive group, the first of which attaches to the label and the second of which attaches to the specific binding agent.

In other examples, the probe, or specific binding agent (such as an antibody, e.g., a primary antibody, receptor or other binding agent) is labeled with an enzyme that is capable of converting a fluorogenic or chromogenic composition into a detectable fluorescent, colored or otherwise detectable signal (e.g., as in deposition of detectable metal particles in SISH). As indicated above, the enzyme can be attached directly or indirectly via a linker to the relevant probe or detection reagent. Examples of suitable reagents (e.g., binding reagents) and chemistries (e.g., linker and attachment chemistries) are described in U.S. Patent Application Publication Nos. 2006/0246524; 2006/0246523, and U.S. Provisional Patent Application No. 60/739,794.

It will be appreciated by those of skill in the art that by appropriately selecting labeled probe-specific binding agent pairs, multiplex detection schemes can be produced to facilitate detection of multiple target nucleic acid sequences (e.g., genomic target nucleic acid sequences) in a single assay (e.g., on a single cell or tissue sample or on more than one cell or tissue sample). For example, a first probe that corresponds to a first target sequence can be labeled with a first hapten, such as biotin, while a second probe that corresponds to a second target sequence can be labeled with a second hapten, such as DNP. Following exposure of the sample to the probes, the bound probes can be detected by contacting the sample with a first specific binding agent (in this case avidin labeled with a first fluorophore, for example, a first spectrally distinct QUANTUM DOT®, e.g., that emits at 585 nm) and a second specific binding agent (in this case an anti-DNP antibody, or antibody fragment, labeled with a second fluorophore (for example, a second spectrally distinct QUANTUM DOT®, e.g., that emits at 705 nm). Additional probes/binding agent pairs can be added to the multiplex detection scheme using other spectrally distinct fluorophores. Numerous variations of direct, and indirect (one step, two step or more) can be envisioned, all of which are suitable in the context of the disclosed probes and assays.

Additional details regarding certain detection methods, e.g., as utilized in CISH and SISH procedures, can be found in Bourne, *The Handbook of Immunoperoxidase Staining Methods*, published by Dako Corporation, Santa Barbara, Calif.

KITS

Kits including at least one nucleic acid disclosed herein (such as a FPC nucleic acid molecule or population of FPC nucleic acid molecules) are also a feature of this disclosure. For example, kits for in situ hybridization procedures such as FISH, CISH, and/or SISH include at least one probe as described herein and/or a nucleic acid that can serve as a template for making such a probe (e.g., a FPC nucleic acid molecule template). Accordingly, kits can include one or more template FPC nucleic acid molecules; one or more amplified FPC nucleic acid molecules; or one or more labeled probes that include labeled amplified FPC nucleic acid molecules.

The kits can also include one or more reagents for performing an in situ hybridization assay, or for producing a probe. For example, a kit can include at least one FPC nucleic acid molecule (or population of such molecules), along with one or more buffers, labeled dNTPs, a labeling enzyme (such as a polymerase), primers, nuclease free water, and instructions for producing a labeled probe.

In one example, the kit includes one or more FPC nucleic acid molecules (unlabeled or labeled) along with buffers and other reagents for performing in situ hybridization. For example, if one or more unlabeled amplified FPC nucleic acid molecules are included in the kit, labeling reagents can also be included, along with specific detection agents and other reagents for performing an in situ hybridization assay, such as paraffin pretreatment buffer, protease(s) and protease buffer, prehybridization buffer, hybridization buffer, wash buffer, counterstain(s), mounting medium, or combinations thereof. The kit can optionally further include control slides for assessing hybridization and signal of the probe.

In certain examples, the kits include avidin, antibodies, and/or receptors (or other anti-ligands). Optionally, one or more of the detection agents (including a primary detection agent, and optionally, secondary, tertiary or additional detection reagents) are labeled, for example, with a hapten or fluorophore (such as a fluorescent dye or QUANTUM DOT®). In some instances, the detection reagents are labeled with different detectable moieties (for example, different fluorescent dyes, spectrally distinguishable QUANTUM DOT®s, different haptens, etc.). For example, a kit can include two or more different binding regions that are substantially or entirely free of repetitive (or other undesirable, e.g., background-producing) nucleic acid sequence, probes (e.g., an amplified FPC nucleic acid molecule or mixtures of amplified FPC nucleic acid molecules) that correspond to and are capable of hybridizing to different target nucleic acid sequences (for example, any of the target sequences disclosed herein). The first probe can be labeled with a first detectable label (e.g., hapten, fluorophore, etc.), the second probe can be labeled with a second detectable label, and any additional probes (e.g., third, fourth, fifth, etc.) can be labeled with additional detectable labels. The first, second, and any subsequent probes can be labeled with different detectable labels, although other detection schemes are possible. If the probe(s) are labeled with indirectly detectable labels, such as haptens, the kits can include detection agents (such as labeled avidin, antibodies or other specific binding agents) for some or all of the probes. In one embodiment, the kit includes probes and detection reagents suitable for multiplex ISH.

In one example, the kit also includes an antibody conjugate, such as an antibody conjugated to a label (e.g., an enzyme, fluorophore, or fluorescent nanoparticle). In some examples, the antibody is conjugated to the label through a linker, such as PEG, 6x-His, streptavidin, and GST.

EXAMPLES

Example 1

Production of HER2 Substantially Repeat-Free Probe

This example describes methods used to generate a probe including heterogeneous FPC nucleic acid molecules from a human genomic target that includes the HER2 gene. Similar methods can be used to generate a probe including heterogeneous FPC nucleic acid molecules from other target nucleic acid sequences, using the appropriate primers.

Three bacterial artificial chromosomes (BAC) clones containing human chromosome 17 nucleic acid sequences spanning the HER2 gene were obtained from Invitrogen (Carlsbad, Calif.). The three clones were designated CTD-2019C10 (C10; GENBANK™ Accession No. AC040933), RP11-94L15 (94L; GENBANK™ Accession No. AC079199), and RP11-387H17 (H17; GENBANK™ Accession No. AC090844). The HER2 coding sequence is contained within 94L, where it is transcribed from left to right (that is, from C10 towards H17). BAC DNA was made from 4 liter cultures and purified using Qiagen (Valencia, Calif.) large construct preparation kits according to manufacturer's instruction.

The polynucleotide sequences of these three BAC clones were obtained from GENBANK™, and repetitive sequences were identified using the program RepeatMasker. The RepeatMasker program replaces all nucleotides in repetitive elements with "N." Following identification of repetitive elements, all but one N was deleted for each repetitive element. Amplification primers were then selected to amplify non-repeat sequences between each N using the computer program OLIGO™. Oligonucleotide primers were selected for a Tm as close as possible to 69° C., and a position as close as possible to each end of the unique binding region segment, to maximize the size of the PCR products. Primers for amplification of binding regions of the chromosome 17 region including the HER2 gene that were substantially free of repetitive nucleic acid segments are shown in Table 1.

TABLE 1

Primers used to generate binding regions for a HER2 probe.

| SEQ ID NO: | Forward Sequence | SEQ ID NO: | Reverse Sequence | Product B.P. |
|---|---|---|---|---|
| BAC C10 End to 120K | | | | |
| 1 | AAATGATTAGCAAGGCCAGAAGTC | 179 | GGGGAAAAATCAGAAAACTACACT | |
| 2 | AACTGGACAAGCTCTTTGGGA | 180 | GAACCTGCCTCTGTCTTTGATACC | 797 |
| 3 | CCAGCTCCAAAAATGAAAAG | 181 | TGTGCATCAGCTATCCAACAA | 1368 |
| 4 | AACCAGGCAGGCAACTTATTA | 182 | CCACGTCCAGGCTGTTTATTT | 1334 |
| 5 | TTCAATGACCAGACTCCTTGC | 183 | CCAAGGCACTGTTTTTTGAAG | 1204 |
| 6 | TAATGCATGGTAGGACCGAAT | 184 | TATTAGGGTGGTGGGTCTTCC | 1489 |
| 7 | ATTAGCCAGCATTTTGTGACC | 185 | CAAGCTGACAGAATGGAGAGG | 3016 |
| 8 | GAACCAACAGGATGTGCGATA | 186 | GATTATGCAGTAACCACAAGG | 737 |
| 9 | TTCAAACTGCAAAACCCTGTG | 187 | TGGAAACTCTGGGACACTCAA | 565 |
| 10 | GAGAGAGACAGGCACACATGG | 188 | AATGTTACCTTTGAGGGGTGG | 3319 |

TABLE 1-continued

Primers used to generate binding regions for a HER2 probe.

| SEQ ID NO: | Forward Sequence | SEQ ID NO: | Reverse Sequence | Product B.P. |
|---|---|---|---|---|
| 11 | ACCCTGCCCCACACATCTACT | 189 | GCTCCAGGTCTTCCCTCTCTC | 1595 |
| 12 | CCCTGCTCTAGCCTTTGTTCT | 190 | GTCCAGTCTGCAACATCCAAC | 1482 |
| 13 | CTGAACTTCCACCCCCTTTAC | 191 | TGGTTCCCTTCTTGATTCAGC | 618 |
| 14 | GCAGTACGTGGCAGATGTGAA | 192 | GTTGCTGGGAGTCCTGTGTCT | 1691 |
| 15 | GAGGAGGTAAAGAGGTCCCAG | 193 | TACAACATAGAGGGGAGGCAC | 1157 |
| 16 | CTCTCCTGCCTTTCTGACTCC | 194 | AGCACAAAGTTGCTCACAGGA | 305 |
| 17 | GCCTCCCACTTTTCTCTTTTC | 195 | ACCTGTCCTATCCACCCATTT | 2705 |
| BAC C10 120K to 64K | | | | |
| 18 | CCAGAGCTTTCTCCAGGTCAC | 196 | AGGAGTAGCAGGACACCCGTT | 792 |
| 19 | CCCCAGAGTCTGGTGCTACTT | 197 | GCCCCACCACTTTCTCTTTCT | 4400 |
| 20 | ATGGCTGTGGTTTGTGATGGT | 198 | ACAAGAAGGTTTTGAGGCTCC | 1356 |
| 21 | ACACCATGAATTGTTGAAGCC | 199 | AGGTTTGCGGGAGTCATATCT | 1085 |
| 22 | TAATGCGTTTTCCTCTCTGGG | 200 | GGGAGAGTTGGTCCCCTTTTA | 503 |
| 23 | GGAGTGATGTCCACCCTGTTC | 201 | AGCTGGGTCTGAATCCAGGTA | 1674 |
| 24 | ATGCGTGGTAGGGCATTTAAG | 202 | CTCTGGTCTCCCATCTGCTTT | 785 |
| 25 | ATGGACAACTCACTCCTCCCT | 203 | GTTGAAAGAACAAGGCAGCTC | 1522 |
| 26 | CCACTCCCCATTGTTGTTGTT | 204 | AGTGGGAGAGGGATAGTGGCT | 2259 |
| 27 | ATTCCAGCCAACAATAATGGG | 205 | GCAGTACCTGCAACTTGGTGA | 708 |
| 28 | AAGTTGTGGACAGTCGAGACG | 206 | AATGCACACAGGTGGACAGAT | 774 |
| 29 | TCGATGTGACTGTCTCCTCCC | 207 | CTCCAACTGCATTCCAACAAG | 479 |
| 30 | GGACACCTCTAACCCTGATCC | 208 | AACTTATTCCTTGGACCGCTG | 414 |
| 31 | AGTCTCCATGGCTGGTCAATG | 209 | TACCAAGAGGGGAGACAGAGG | 764 |
| 32 | CCATCAGAAACGAATTGTCCC | 210 | GCACCAAAGTCTCCTCCCTCT | 1085 |
| 33 | TCCAGGGCTGTAAAATCATCA | 211 | GGTCAACTCCAGGGGACACTA | 471 |
| 34 | TGGTTCTTTGCCCACTATGGT | 212 | GGTGGTGACAGTAAACAGCCC | 922 |
| 35 | AAACTGTGCCTCGCTAGACAA | 213 | CCCCATTCATGCTCTCTCTTT | 548 |
| 36 | TGGAATTGAGATTGCTCCAAG | 214 | TGTTGCTTCAGCATGTCAAGA | 627 |
| BAC C10 64K to 1 | | | | |
| 37 | TGAAAAATCCAAGAATCAGGG | 215 | AGGGTTTAGCACTTGTGGAGG | 771 |
| 38 | CACCACTTCACCCTCCTCTCT | 216 | AGATGTTAGATGTTGGGGTGG | 638 |
| 39 | AGGGTCTCTCCATTCCAGAAC | 217 | TCCACCTCTGTCTCCCTTCTC | 694 |
| 40 | CATACTCCTCCCAGTGCTCCT | 218 | TGGGTCTCTGTGAGTGGAAGG | 2035 |
| 41 | CAGACCAGAACGAGGGAGAGT | 219 | GTCCCTAAAGCCTTGTTCCTG | 3457 |
| 42 | TTTGAGGACATCACCATGACA | 220 | TGACCTTGGCCTTCCTTAGTT | 935 |
| 43 | CGGACACTAAGGGAGATGGAT | 221 | ATACCTACCAGCCAGGCTCAG | 723 |
| 44 | ACCACTTACCTGACCACTGGC | 222 | AATCTTTAGACCCCCTCACCC | 3413 |
| 45 | CGTTGTAGGAGGATTCAAGCA | 223 | TTAATACAAAGGTCCCCCAGG | 1424 |
| 46 | GCGACCTGTTCCAAAAGTCTC | 224 | ATGGGGAAGAGTGGGGTCTAT | 881 |

TABLE 1-continued

Primers used to generate binding regions for a HER2 probe.

| SEQ ID NO: | Forward Sequence | SEQ ID NO: | Reverse Sequence | Product B.P. |
|---|---|---|---|---|
| 47 | CAGGTGGGAGAGGGAAGATAA | 225 | GTCTTGTTCCACAGCACCATC | 2936 |
| 48 | CTGGAAAGAGGAAGGAGGACA | 226 | TATGCTGCCAAAAGAGAACCC | 1279 |
| 49 | CTTCCTCCAGGTCTCATGCTT | 227 | GTCTGCCAAGGGAAACATCAT | 595 |
| 50 | TCTCCATAGCTCCAAGCACAC | 228 | CCTGTTGTTCCTCCCAGTCTT | 944 |
| 51 | CCCTACCTCCCACTCTCACTC | 229 | CCAGCACCAGGGAGTAGTTTG | 1757 |
| 52 | GGCTAGGAAACGCCTACTGAG | 230 | GAGTGCAGGGGCTGATCTCTA | 313 |
| 53 | CAGATGAATGCTAAGCCCAAA | 231 | CTCTGACTGACTGGCGAGATG | 522 |
| 54 | CCACATCAGTGGGACAAAAGA | 232 | CCCTGGAGAAGTGGGAGTGTA | 596 |
| 55 | CCTGGCTCTTTGCCAATAAAT | 233 | CCCAAACACCAGGTACTAGGC | 515 |
| 56 | CGCAGAGCCTGTGTTCTTATC | 234 | CGGTACGAAGAAAACCAGGAG | 2238 |
| 57 | GGCTGAAGTCCTGAAGGTCAT | 235 | TCTCACCCCTCTTCCACTGTT | 828 |
| 58 | CAGGTCCAAGAAGAGGGAAGA | 236 | CTGCAGGTGAGACTCAGCAAT | 2579 |
| 59 | TGAACAGGAGTCAAAGCTGGA | 237 | GAAAGGGAAGCAGGAAAGAGG | 1188 |
| 60 | GACACGCAGAGACACTCAGGA | 238 | CCCTTCCTATCTTCTCCCACC | 1833 |
| 61 | ATAAGTTCAGCAGAGCCTCCG | 239 | AATGAGCATGGAGAATCGTGT | 1808 |
| 62 | AAACACATCTTGCTTGGGAGG | 240 | GAATGGGACTCCTGAGAGCTG | 587 |
| 63 | GTCCCTTTGGAACTTGCAGAT | 241 | TAACACATTCAGGATGGACGC | 1237 |
| 64 | CCATCTCGCTCCCTACAAAGT | 242 | AGAGCACTGACCCTCCTTAGG | 1135 |
| BAC 94L 1 to 64K | | | | |
| 65 | TAGTGACTGAGGGTGGAAGGG | 243 | CCACTCACGAAGATGTCGAAG | 1166 |
| 66 | CCTGTGCAAGGTTACATCCAA | 244 | CCTTAAGAGGCAGCCAGACTG | 2955 |
| 67 | GCGACCTGTTCCAAAAGTCTC | 245 | CACAGCCTGACTGGACAAAAG | 838 |
| 68 | CGTTGTAGGAGGATTCAAGCA | 246 | CTGGGAGAGGCAGAGATTCAT | 1379 |
| 69 | CAGGTGTTGGGGTAGAACTGG | 247 | CTCTTTCCTGATTCGAGGTGG | 3386 |
| 70 | CGGACACTAAGGGAGATGGAT | 248 | ATACCTACCAGCCAGGCTCAG | 723 |
| 71 | TCCAGATGGAGACACATTTGC | 249 | TGACCTTGGCCTTCCTTAGTT | 1147 |
| 72 | AACAGTGCAGACTGCTTCAGA | 250 | TGTTCCTGGGCACATTTTTAA | 3461 |
| 73 | AGTGCTCCTCAGAGGGAGTTG | 251 | CCAAATCTGAGGAAAGGGTGA | 2116 |
| 74 | TAGACTGACTCTCACCACGCC | 252 | CATCCACCTCTGTCTCCCTTC | 785 |
| 75 | CACCACTTCACCCTCCTCTCT | 253 | AGATGTTGGGGTGGTAGAAGG | 631 |
| 76 | CCAAGAAGGAAGCTGAGTTGC | 254 | GGTGGAGACAGGGTTTAGCAC | 815 |
| 77 | ACTATGGCTGTGACTCCCCAC | 255 | ATCTACCCTGACCCATCTGGT | 833 |
| 78 | GGTACCAGCAAACTGTGCCTC | 256 | TCCAACTTACAGGCCCTCTTG | 597 |
| 79 | GGTTCTTTGCCCACTATGGTC | 257 | TTTGCTCATTAACCCATCAGG | 908 |
| 80 | TCCAGGGCTGTAAAATCATCA | 258 | AGGGGAGACTCCCTATTTGTC | 729 |
| 81 | AGGTGGGTTCAGTGAATGAAA | 259 | ACCTACTTCACCAGCCAGCTT | 1085 |
| 82 | TCCATGGCTGGTCAATGATT | 260 | ATTACCCTCAAGAGCCCCAGT | 787 |

TABLE 1-continued

Primers used to generate binding regions for a HER2 probe.

| SEQ ID NO: | Forward Sequence | SEQ ID NO: | Reverse Sequence | Product B.P. |
|---|---|---|---|---|
| 83 | ATGGCGTCCACAGTAGCTTTT | 261 | AGGGTTAGGGTGAGGATCAGG | 382 |
| 84 | CCTTTCGATGTGACTGTCTCC | 262 | CCAACTGCATTCCAACAAGTC | 481 |
| 85 | CGAAGTTGTGGACAGTCGAGA | 263 | AATGCACACAGGTGGACAGAT | 776 |
| 86 | ACACTGCTCCCTGAGTCACTG | 264 | GCTCAGCCTGACAGCTCAGTA | 488 |
| 87 | CCACTCCCCATTGTTGTTGTT | 265 | GCTGGCAAGAGAGCACAAGAT | 2210 |
| 88 | GAGAAGGAAGGAGAGAGCTGC | 266 | GCTGTTGAAAGAACAAGGCAG | 1572 |
| 89 | ATGCGTGGTAGGGCATTTAAG | 267 | CTGGTCTCCCATCTGCTTTCT | 783 |
| 90 | AGTGATGTCCACCCTGTTCCT | 268 | AGCTGGGTCTGAATCCAGGTA | 1672 |
| 91 | GTAATGCGTTTTCCTCTCTGG | 269 | GTGGGGATAGAACTGCTAGGG | 604 |

BAC 94L 64K to 120K

| 92 | ACACCATGAATTGTTGAAGCC | 270 | AACCCCAATGAAGAGAGACCA | 1059 |
| 93 | GTGTGTGGTCTCCCATACCCT | 271 | GTTCCTCAAGAGTGGCTTTGG | 1352 |
| 94 | CTCTACCACCTGAGGGCTTTG | 272 | CCAACATGAGTTCCCTTCCAT | 3633 |
| 95 | TCCAGGGTGGACCTCTTATCA | 273 | CACCTGTCCTATCCACCCATT | 4080 |
| 96 | GCACACAACTGGTTCCGTTAA | 274 | AGAGGGGAGGCACAGGACTTA | 1300 |
| 97 | AAGTCCTGCTCACTCATGCTG | 275 | GCTGGGAGTCCTGTGTCTCAT | 1578 |
| 98 | AATAAAAGGAAATGGTGGGGC | 276 | TGGTTCCCTTCTTGATTCAGC | 679 |
| 99 | CATTCCTCAGCCACAGTGACA | 277 | CTGGACATGCTGAAGAGGTGA | 576 |
| 100 | CCCTGCTCTAGCCTTTGTTCT | 278 | CTCTCCTCCCCCAACTCAACT | 1435 |
| 101 | CCCACACATCTACTGGAGGAA | 279 | CTCCTAAGACAGGCCTCAACC | 1625 |
| 102 | AAGGAGAGAGACAGGCACACA | 280 | ATGTTACCTTTGAGGGGTGGT | 3321 |
| 103 | CCTTGAAGAACCAACAGGATG | 281 | GAAGAAGGTGGTGGAGAGGAA | 593 |
| 104 | TGTGACCTCCTATTCCAGTGC | 282 | CACCTCAAGAACAGGAACTGG | 3179 |
| 105 | TAATGCATGGTAGGACCGAAT | 283 | TATTAGGGTGGTGGGTCTTCC | 1489 |
| 106 | TCTCCCACCAACTTTCAATGA | 284 | CCTCTCCAAGGCACTGTTTTT | 1223 |

BAC 94L 120K to end

| 107 | GAGGGGATCTCCCTAAACTGA | 285 | GCACCATGCTTTTTTTTCAAA | 1697 |
| 108 | GGAACATTCATCCTGGTTCCA | 286 | TCAAAGGGCACTCATTTCATG | 901 |
| 109 | AACTGGACAAGCTCTTTGGGA | 287 | AACCTGCCTCTGTCTTTGATACC | 796 |
| 110 | AGTCCTGTTGCCCAATACCTG | 288 | GAGGGGGAAAAATCAGAAAAC | 820 |
| 111 | AAAAAGCAGAAGCACTGCAAG | 289 | ATTGAGGGTAGAGGAGGTTGG | 634 |
| 112 | TCTGAAGAAATGTACGGCAGC | 290 | CGAATGGCTAACTCCCACAAA | 535 |
| 113 | ATGAAGGAAAGGTTTCACCCA | 291 | GGGACCTCATGTTCTTGATGTTA | 643 |
| 114 | CCAATCAAGAGGAAAGTTGGA | 292 | AATAGCCTTGCTAGTGGGTGC | 875 |
| 115 | TCCTTACAAGGTGTTGAGGGC | 293 | CATGGGGAGGTACAACTTTTG | 1935 |
| 116 | TTGGATTTGACCTCATGCACT | 294 | CCCCAGTAACCATGCAGAGAG | 1148 |
| 117 | CAGAGGCAGGGAAAAGATGTC | 295 | GGCATTTTCAAAATTAACAGACG | 1377 |
| 118 | CTGGCCATCAGTAAATCACATCA | 296 | GGCAACATCTAAAACTTCAGCCT | 551 |

TABLE 1-continued

Primers used to generate binding regions for a HER2 probe.

| SEQ ID NO: | Forward Sequence | SEQ ID NO: | Reverse Sequence | Product B.P. |
|---|---|---|---|---|
| 119 | ATTAGCCGAAGACAGAGGGAA | 297 | TTGCTTGCAGCCTTGAAGTAT | 435 |
| 120 | TGTTGAAAAACACAAGGGCAC | 298 | AGGTGTCTTTAAGCCTGAGCC | 1876 |
| 121 | TATTCCCAGAACTTTGGCACA | 299 | AAAATCCTGTCCTGGCTCATC | 572 |
| 122 | CCCGTTTGACACAGTACAAGC | 300 | TACACCCTTCATCTCCTGGCT | 766 |
| 123 | TAAATGTGCAACTCAGGCAGG | 301 | AAGATTTGGCACTTGAAAGGA | 1456 |
| BAC C17 1 to 64K | | | | |
| 124 | CCCATCGTTTCAGTGTTCTTCTT | 302 | CACGAACACACACACACACCC | 1007 |
| 125 | TGCAAGGGAATTTTGAATGAA | 303 | CATCACTTCAAACACAAGAGCATT | 628 |
| 126 | ATAGATTGCAGTTTGTTGGCC | 304 | TATTAGCCGAAGACAGAGGGA | 528 |
| 127 | AGGTGTCTTTAAGCCTGAGCC | 305 | CCTGATTGGACATTTCCCATA | 1801 |
| 128 | TACACCCTTCATCTCCTGGCT | 306 | ACAAGCTGTAAAGCTCTGCCC | 751 |
| 129 | TCAAAAGGGCATCAGTGAGGA | 307 | TAAATGTGCAACTCAGGCAGG | 1415 |
| 130 | CTGGCACAGGATGTGGTCATT | 308 | GTGCTTCACCACTTGGGTTTT | 407 |
| 131 | GAGTCCATGGTGACCACATTTT | 309 | GACCCCCATTTAACTTTCAGC | 1064 |
| 132 | ATCACAGCCATCATGGTCAAC | 310 | GGCTGAGGCTTTATTTTGGAG | 1476 |
| BAC C17 180 to end | | | | |
| 133 | TGCCACATTTACAGTCCCAGG | 311 | GCGGTTTTCACTGACGCAGTA | 1386 |
| 134 | CCATTTTTCTAATCCATGCCC | 312 | CACCTTTGTGGAACTGCCTAC | 533 |
| 135 | TGCCCCTACACCAAACATACC | 313 | AAACCTTCGCATTTCATCCTC | 218 |
| 136 | CTTCTGTCTGTTATGGTCGGG | 314 | GCCTTTCTGTGGCTTTTGTTT | 506 |
| 137 | TGGGGGTCACATTGATTCATA | 315 | TGTTCTACCAGGACGCCACGG | 832 |
| 138 | GGTGTTGGGAGAAGATGTTGA | 316 | ACGCAAGGACCTGACATTAAA | 2502 |
| 139 | CCTTGGAAATCACTCCTTTGC | 317 | TGGTAACTGAAAATGGGTGGA | 1849 |
| 140 | TGATGGTTTCACTGCATCTGG | 318 | TTAATTGCTTCCACCAACCCT | 2525 |
| 141 | GCTTCTCATAAGCCATGCACA | 319 | AGATCCCTGGTCTTTGTTCCC | 243 |
| 142 | ATGATGCTCTGGGATGTGAAA | 320 | CCTGGAAAGCAGAGAACTAGG | 529 |
| 143 | GTGGTGATTAATTCTTGGGGG | 321 | CATTTTGGCATGTATGTGGTG | 671 |
| 144 | CCTTCAGACCTGCAAAACTCC | 322 | CCCCTCTCCTTAGAAAATCCC | 636 |
| 145 | CTATCAGCTCAGCAGCAAGGA | 323 | GCGAATGGGATACATCAAAGA | 388 |
| BAC C17 120K to 180K | | | | |
| 146 | GCAAGGGCCAAATAACCAAGT | 324 | CAGAGCCTAAAGAACCCACCA | 1330 |
| 147 | ATCCTTTCATGTTCCTTGGCT | 325 | TGCACACTTTAACTGCACCAT | 908 |
| 148 | TGGCTTCTGTTTCTGAGTTGG | 326 | CAGTAAGCAAACTGCCCTCAT | 598 |
| 149 | CCTTAATCTGCCTCCAGCTCA | 327 | AGCCAAAGGTTCCAGGACAAT | 913 |
| 150 | TAAGTTGGGGTTTGGGGAGAT | 328 | CCAGCACCTCACCCTGACTAT | 4665 |
| 151 | CGCACCAAAATTCTATCATCC | 329 | TGTGATGCTACCCACTCCACT | 2847 |
| 152 | CTTTCTTGCCTTAATGCTGGG | 330 | GGTCTCCTCGGTTACTCCCAT | 581 |
| 153 | GAAGAAGGTGATCTGGGAACG | 331 | GCAAGTGCAAGGAAGGAAAGA | 590 |
| 154 | TCACTCTGTTGGTTGTGTCGG | 332 | GGAGGCCTGCTGAACTTCTTT | 462 |

TABLE 1-continued

Primers used to generate binding regions for a HER2 probe.

| SEQ ID NO: | Forward Sequence | SEQ ID NO: | Reverse Sequence | Product B.P. |
|---|---|---|---|---|
| 155 | GGACCAGACCAGATGGTAGGA | 333 | GCACATAAGGCTCACAGGAAA | 618 |
| 156 | TCAAACATCCTACAGCGAAGC | 334 | ATAGTGTGGGTAGGATGGTGC | 3185 |
| 157 | CCTCTCCCTCTCCTCTCATCA | 335 | AAAAGCAAGAGCAGAGAAGGC | 1182 |
| 158 | TCTCAAGTGCATCACCAGCTC | 336 | AGGCGCTGCAACTACAAAGAT | 562 |
| 159 | TAAGCCTACCACACCAGCCAC | 337 | CTGACCTTCACAGACATCCCC | 920 |
| 160 | AGAGCACCCAGCAGGTACAGA | 338 | GGACTACAAGGGACGAGAGGC | 564 |
| 161 | GGGCAAGGAGAATGTTGTAGG | 339 | CTGGGAGGATCACCTGACAGA | 589 |
| 162 | TGTCGTTAGTCATCTGGTCCC | 340 | CACCACCAAGACAAGCCTAAA | 695 |
| BAC C17 64K to 120K | | | | |
| 163 | GACACACTTCCTCCATCTGGC | 341 | CCATAAATGAAGCCTCCTGCC | 737 |
| 164 | GTCTCTGCTCACCCCACTCAT | 342 | CTTGGAAAAGCCAATGGAAAT | 606 |
| 165 | TTGAGGACAAAGGTCTCAGGC | 343 | AAGGTCCTAGCCCTTAGCAGA | 809 |
| 166 | TTACCTGTTAGGGCTCCAACG | 344 | ACACACACATCTGCAACTCGG | 1410 |
| 167 | CCAGCGGTTTGATGAGATTGT | 345 | CCGTTTCAGCAAAACTGAGAA | 684 |
| 168 | AAATAAATCCACAGCCGAGGT | 346 | AGTGTCTTAGTCACCCCCTGC | 1679 |
| 169 | CACCATCACATCCTCAAAAGC | 347 | CCCAGGATGTGGAGATGAAAG | 1099 |
| 170 | CAGAAGAAAGAGGCAGCAGCA | 348 | GGTGGGGGACTAGGAGTGAAA | 574 |
| 171 | GGACAGGGCTGAACGAAATAA | 349 | ACGAAGTCAGTTTGGTGGTGG | 493 |
| 172 | CACATGCACATCCATGCTCTC | 350 | CACCCACACTTTTCTGCCTCT | 1693 |
| 173 | AGCTGGTGATGGACACATGGT | 351 | GGTGAGCCCTTATCCTCAGTT | 1413 |
| 174 | TTAACCCACCTGAACCTGTCC | 352 | CTCCAGCCCTGGTCACAATAT | 348 |
| 175 | AGAACTTTCCTCCTCCTCCCT | 353 | CGTGTCCACTTCAAGGTGAAT | 3389 |
| 176 | TGTGAGGGAAATCTACCTTCG | 354 | CACCAGGCTTGTCATTTACCA | 951 |
| 177 | GATCTCAGGGTCTTCTCTGGG | 355 | GATGCCTCATCTTTCCTCACT | 1048 |
| 178 | TGTTTATTTATGTGGCAGGTTGG | 356 | GTGAACTCACTCACTTGGGTAGC | |

Forward primers were synthesized with a 5' phosphate, whereas reverse primers were not. The resulting amplification products possessed 5' phosphates at a single end.

The primers were dissolved in water and diluted to 20× the final reaction concentration. Final concentration was 0.5 µM for each primer. The resulting binding regions were amplified by the polymerase chain reaction (PCR) using TOPOTAQ™ (Fidelity Systems Inc., Gaithersburg, Md.). In each initial reaction, 0.2 µg BAC DNA was used as a template in a final volume of 100 µl. PCRs were performed in a mixture containing: 0.5 mM each dNTP, 0.5 µM each primer, 1 Unit TOPOTAQ™, in buffer at a final pH of approximately 8.0. PCR conditions were as follows: 98° C. 5 minutes, 30 cycles of 98° C. 10 seconds, 55° C. 20 seconds, 72° C. 3 minutes, followed by a 10 minute incubation at 72° C. The completed reactions were stored at 4° C.

The amplification products of each initial reaction were run on low melting point agarose gels and, after photographing, cut out and purified. The gel fragments were digested with GELASE™ (Epicentre, Madison, Wis.) according to manufacturer's instructions and recovered by isopropanol precipitation. The precipitated DNA products were dissolved in 100 µl water. These products were designated "SEED1."

Polymerase chain reactions (100 µl) were set up containing 1 µl of SEED 1, and amplified using the same conditions and primers as above. The product of this reaction was diluted to 200 µl and designated "SEED 2."

Each SEED 2 (5 µl) was used to set up reactions, the products of which were called "SEED 3." Each SEED 3 reaction was performed 10 times and the resulting 10 reactions were combined in a single deep well microtiter plate. These were called "combined PCR products."

An aliquot (10 µl) of each of the combined PCR products was run on an agarose gel to test for success of the reactions. Aliquots of each combined reaction were combined and purified by phenol extraction and recovered by isopropanol precipitation. The precipitated pellet was dissolved in 100 µl TE.

This process was performed for each of the three BACS resulting in 100 μl products for each BAC. Final concentrations were determined spectrophotometrically to be: C10 828 ng/μl; 94L 525 ng/μl; and H17 717 ng/μl. Volumes corresponding to 10 μg of each (that is, 12 μl, 19 μl, and 14 μl, respectively) were combined, and treated with T4 DNA polymerase and 4 dNTPs in a 500 μl reaction, to generate flush ends.

The amplified binding region products were phenol extracted and precipitated, then ligated as follows. The binding region amplicons were dissolved in 40 μl water and treated with T4 Polynucleotide kinase (NEB, according to the manufacturer's instructions), followed by T4 DNA ligase overnight at room temperature in the same buffer. The next day a 1 μl aliquot was run on an agarose gel to confirm ligation. The ligation reaction produced a diffuse band of approximately 10 kb, with no visible residual un-ligated fragments. This material was phenol extracted and recovered in a 30 μl volume of TE. The resuspended product, designated SEED H-ZERO (the resulting FPC nucleic acid molecules) was stored frozen.

SEED H-ZERO (the FPC nucleic acid molecules) was then amplified with Phi29 polymerase using random hexamers as primers, under the following reaction conditions: approximately 20 μg of template in a buffer containing 37 mM trisHCl pH 7.5, 50 mM KCL, 10 mM $MgCl_2$, 5 mM $(NH_4)_2SO_4$, 1 mM dNTP's, 50 μM primers, 1 μg/ml Pyrophosphatase (yeast), and 0.5 μg/ml phi29 DNA polymerase.

SEED H-ZERO (1 μl) was amplified in a 100 μl reaction at 30° C. overnight. This reaction produced a very large amount of DNA (approximately 1 mg/ml), which was designated H1. From the 100 μl of H1, 10 μl was used to set up a 1 ml reaction to produce H2. H2 was identical to H1 in appearance on an agarose gel. 100 μl of H2 was used in a 10 ml amplification reaction to produce H3, which again was identical in appearance by gel analysis. One ml of H3 was used in a 50 ml (2×25 ml) reaction which was allowed to proceed for approximately 60 hours to produce H4. The product of H4 was precipitated with isopropanol and dissolved in a total of 10 ml TE buffer. Approximately 28.9 mg DNA (H4) was produced by this series of reactions.

H4 DNA (100 μg) (the resulting FPC nucleic acid molecule amplicons) was labeled with dinitrophenol (DNP), using the MIRUS kit according to manufacturers instructions. DNA was purified by isopropanol precipitation and washed with 80% EtOH. After labeling and purification, the DNA was adjusted to 50 mM NaPO4 buffer pH6.8, 10 mM EDTA, and heated at 100° C. in a water bath for 45 minutes to fragment the DNA. This probe containing labeled FPC nucleic acid molecule amplicons was used in the initial experiments.

Example 2

Probe Synthesis Using Fixed Oligonucleotide Sequences

This example describes an alternate method used to generate a probe including heterogeneous FPC nucleic acid molecules specific for a region of human chromosome 17 containing the HER2 gene. In this example, a fixed oligonucleotide sequence (a hexamer consisting of purines) was used to minimize primer-derived amplification products. However, one skilled in the art will appreciate that similar methods can be used with other fixed oligonucleotide sequences. Similar methods can be used to generate a probe including heterogeneous FPC nucleic acid molecules from other target nucleic acid sequences using the appropriate primers.

The fixed oligonucleotide sequence was a hexamer consisting exclusively of purines, GAGGAG (SEQ ID NO: 357). The hexamer GAGGAG (SEQ ID NO: 357) is the recognition site for the restriction endonuclease BseI, which can be subsequently used for analysis and further manipulation of the probes. Two alternative approaches to incorporating fixed oligonucleotide sequences into a binding region amplicon are described.

In the first method, substantially repetitive nucleic acid sequence-free binding regions from the chromosome 17 region including the HER2 gene were generated and amplified as described in Example 1. The resulting binding region amplicons were ligated at one (or both) end(s) to duplexed (double stranded) oligonucleotides (for example, hexamers) that consist of all purines on one strand and complementary pyrimidines on the other strand. Because one strand of the duplexed fixed oligonucleotide is composed of an all pyrimidine sequence, e.g., CTCCTC (SEQ ID NO: 358), subsequent amplification can be carried out using only a single primer e.g., GAGGAG (SEQ ID NO: 357). The hexamer-containing binding region amplicons subsequently were ligated to form a FPC nucleic acid molecule as described in more detail below.

In a second approach, substantially repetitive nucleic acid sequence-free binding regions from the chromosome 17 region including the HER2 gene are amplified to form binding region amplicons using a sequence-specific primer that has incorporated into it a sequence consisting exclusively of purines. The fixed oligonucleotide sequence (purines) is incorporated into the primer 5' to the region complementary to the target sequence from which priming and extension is initiated. The resulting binding region amplicons include a hexamer sequence at the 5' end. The hexamer-containing binding region amplicons are subsequently ligated to form a FPC nucleic acid molecule as described in more detail below.

The methods described above each introduce the hexameric sequence at the ends of each PCR fragment (i.e., binding region amplicon). The hexamer-containing binding regions amplicons then were ligated together (as described in Example 1) to generate a population of FPC nucleic acid molecules that included the hexamer sequence between each binding region. These hexamer-containing FPC nucleic acid molecules were used as templates for amplification using Phi29 DNA polymerase primed by the all purine hexamer. The resulting amplified FPC nucleic acid molecules were used as probe after labeling with DNP both by chemical and enzymatic methods (see Example 1).

Amplification of the hexamer-containing FPC nucleic acid molecule with an all purine primer reduces (or eliminates) the occurrence of primer only products (e.g., primer dimers) in the final amplification mix. Moreover, at the standard primer concentration used for the hexamers, the molar concentration of the fixed hexamer primer is available at more than 4000 times the concentration of any individual random hexamer in a mix. This results in more complete hybridization of primer to its complementary sequence throughout the target nucleic acid sequence, reducing the effect of selective primer depletion during amplification with resultant improvement in retention of sequence heterogeneity as amplification proceeds.

Example 3

In Situ Hybridization Analysis

This example describes methods showing that the probe containing amplified and labeled FPC nucleic acid molecules can be used for in situ hybridization. One skilled in the art will appreciate that similar methods can be used for probes specific for other target nucleic acid sequences.

The labeled probe generated in Example 1 was formulated in hybridization buffer (50% formamide, 2×SSC, 10% dextran sulfate) for use in assays. CISH and SISH were performed on formalin fixed, paraffin embedded four micron thick tissue sections mounted on a glass microscope slide using an automated ISH protocol (see Table 2), available in conjunction with the Ventana Benchmark™ XT instrument (Ventana Medical Systems, Tucson, Ariz.).

TABLE 2

Exemplary automated SISH staining protocol

| Step | Procedure |
|---|---|
| 1 | ***** Select EZ Prep ***** |
| 2 | **** Start Timed Steps ***** |
| 3 | ***** Mixers Off ***** |
| 4 | If *Deparaffinization* is *Selected* |
| 5 | Warmup Slide to *75 Deg C.*, and Incubate for *4 Minutes* |
| 6 | Apply EZPrep Volume Adjust |
| 7 | Incubate for *4 Minutes* |
| 8 | Rinse Slide |
| 9 | Apply EZPrep Volume Adjust |
| 10 | Incubate for *4 Minutes* |
| 11 | Rinse Slide |
| 12 | Apply EZPrep Volume Adjust |
| 13 | Apply Coverslip |
| 14 | Warmup Slide to *76 Deg C.*, and Incubate for *4 Minutes* |
| 15 | Disable Slide Heater |
| 16 | Incubate for *4 Minutes* |
| 17 | ***** Mixers On ***** |
| 18 | Rinse Slide |
| 19 | Apply 900ul of Rinse Buffer |
| 20 | Apply Coverslip |
| 21 | Warmup Slide to *37 Deg C.*, and Incubate for *4 Minutes* |
| 22 | Apply Cell Conditioner #2 |
| 23 | Warmup Slide to *90 Deg C.*, and Incubate for *8 Minutes* |
| 24 | Apply Cell Conditioner #2 |
| 25 | Warmup Slide to *90 Deg C.*, and Incubate for *12 Minutes* |
| 26 | If *Extended CC2* is *Selected* |
| 27 | Apply Cell Conditioner #2 |
| 28 | Apply Short Coverslip |
| 29 | Warmup Slide to *90 Deg C.*, and Incubate for *8 Minutes* |
| 30 | Disable Slide Heater |
| 31 | Incubate for *4 Minutes* |
| 32 | Rinse Slide With Reaction Buffer |
| 33 | Apply 900ul of Reaction Buffer |
| 34 | Apply Coverslip |
| 35 | ***** Select SSC Wash ***** |
| 36 | Rinse Slide With Reaction Buffer |
| 37 | Adjust Slide Volume With Reaction Buffer |
| 38 | Apply Coverslip |
| 39 | Warmup Slide to *37 Deg C.*, and Incubate for *4 Minutes* |
| 40 | If *ISH-Protease 2* is *Selected* |
| 41 | Rinse Slide With Reaction Buffer |
| 42 | Adjust Slide Volume With Reaction Buffer |
| 43 | Apply One Drop of *ISH-PROTEASE 2*, Apply Coverslip, and Incubate for #Incubation Time# |
| 44 | If *ISH-Protease 2* is *Not Selected* |
| 45 | If *ISH-Protease 3* is *Selected* |
| 46 | Rinse Slide With Reaction Buffer |
| 47 | Adjust Slide Volume With Reaction Buffer |
| 48 | Apply One Drop of *ISH-PROTEASE 3*, Apply Coverslip, and Incubate for #Incubation Time# |
| 49 | Disable Slide Heater |
| 50 | Rinse Slide With Reaction Buffer |
| 51 | Apply 300ul of Reaction Buffer |
| 52 | Apply Coverslip |
| 53 | Rinse Slide With Reaction Buffer |
| 54 | Apply 300ul of Reaction Buffer |
| 55 | Apply Coverslip |
| 56 | Rinse Slide |
| 57 | Adjust Slide Volume |
| 58 | Apply Coverslip |
| 59 | Warmup Slide to *37 Deg C.*, and Incubate for *4 Minutes* |

TABLE 2-continued

Exemplary automated SISH staining protocol

| Step | Procedure |
|---|---|
| 60 | Rinse Slide |
| 61 | Adjust Slide Volume |
| 62 | If *HER2 DNA Probe* is *Selected* |
| 63 | Apply One Drop of *SISH DET HYB*, Apply Coverslip, and Incubate for *4 Minutes* |
| 64 | Apply Two Drops of *HER2 DNA Probe*, and Incubate for *4 Minutes* |
| 65 | Warmup Slide to *95 Deg C.*, and Incubate for *12 Minutes* |
| 66 | Warmup Slide to *52 Deg C.*, and Incubate for *4 Minutes* |
| 67 | Apply Short Coverslip |
| 68 | Incubate for *2 Hours* |
| 69 | Rinse Slide |
| 70 | Adjust Slide Volume |
| 71 | Apply Coverslip |
| 72 | Rinse Slide |
| 73 | Apply 900ul of Rinse Buffer |
| 74 | Apply Coverslip |
| 75 | Warmup Slide to *72 Deg C.*, and Incubate for *8 Minutes* |
| 76 | Rinse Slide |
| 77 | Apply 900ul of Rinse Buffer |
| 78 | Apply Coverslip |
| 79 | Warmup Slide to *72 Deg C.*, and Incubate for *8 Minutes* |
| 80 | Rinse Slide |
| 81 | Apply 900ul of Rinse Buffer |
| 82 | Apply Coverslip |
| 83 | Warmup Slide to *72 Deg C.*, and Incubate for *8 Minutes* |
| 84 | Rinse Slide |
| 85 | If *HER2 DNA Probe* is *Not Selected* |
| 86 | If *Chr17 Probe* is *Selected* |
| 87 | Apply One Drop of *SISH DET HYB*, Apply Coverslip, and Incubate for *4 Minutes* |
| 88 | Apply Two Drops of *Chr17 Probe*, and Incubate for *4 Minutes* |
| 89 | Warmup Slide to *95 Deg C.*, and Incubate for *12 Minutes* |
| 90 | Warmup Slide to *44 Deg C.*, and Incubate for *4 Minutes* |
| 91 | Apply Short Coverslip |
| 92 | Incubate for *2 Hours* |
| 93 | Rinse Slide |
| 94 | Adjust Slide Volume |
| 95 | Apply Coverslip |
| 96 | Rinse Slide |
| 97 | Apply 900ul of Rinse Buffer |
| 98 | Apply Coverslip |
| 99 | Warmup Slide to *59 Deg C.*, and Incubate for *8 Minutes* |
| 100 | Rinse Slide |
| 101 | Apply 900ul of Rinse Buffer |
| 102 | Apply Coverslip |
| 103 | Warmup Slide to *59 Deg C.*, and Incubate for *8 Minutes* |
| 104 | Rinse Slide |
| 105 | Apply 900ul of Rinse Buffer |
| 106 | Apply Coverslip |
| 107 | Warmup Slide to *59 Deg C.*, and Incubate for *8 Minutes* |
| 108 | Rinse Slide |
| 109 | If *Chr17 Probe* is *Not Selected* |
| 110 | If *ISH Negative Control* is *Selected* |
| 111 | Apply One Drop of *SISH DET HYB*, Apply Coverslip, and Incubate for *4 Minutes* |
| 112 | Apply One Drop of *ISH NEG CTRL*, and Incubate for *4 Minutes* |
| 113 | Warmup Slide to *95 Deg C.*, and Incubate for *12 Minutes* |
| 114 | Warmup Slide to *52 Deg C.*, and Incubate for *4 Minutes* |
| 115 | Apply Short Coverslip |
| 116 | Incubate for *2 Hours* |
| 117 | Rinse Slide |
| 118 | Adjust Slide Volume |
| 119 | Apply Coverslip |
| 120 | Rinse Slide |
| 121 | Apply 900ul of Rinse Buffer |
| 122 | Apply Coverslip |
| 123 | Warmup Slide to *72 Deg C.*, and Incubate for *8 Minutes* |
| 124 | Rinse Slide |
| 125 | Apply 900ul of Rinse Buffer |
| 126 | Apply Coverslip |
| 127 | Warmup Slide to *72 Deg C.*, and Incubate for *8 Minutes* |
| 128 | Rinse Slide |
| 129 | Apply 900ul of Rinse Buffer |
| 130 | Apply Coverslip |

TABLE 2-continued

Exemplary automated SISH staining protocol

| Step | Procedure |
|---|---|
| 131 | Warmup Slide to *72 Deg C.*, and Incubate for *8 Minutes* |
| 132 | Rinse Slide |
| 133 | Adjust Slide Volume |
| 134 | Apply Coverslip |
| 135 | Disable Slide Heater |
| 136 | Rinse Slide With Reaction Buffer |
| 137 | Adjust Slide Volume With Reaction Buffer |
| 138 | Apply Coverslip |
| 139 | ***** Procedure Synchronization ***** |
| 140 | Warmup Slide to *37 Deg C.*, and Incubate for *4 Minutes* |
| 141 | Rinse Slide With Reaction Buffer |
| 142 | Adjust Slide Volume With Reaction Buffer |
| 143 | Apply One Drop of *Rabbit anti-DNP*, Apply Coverslip, and Incubate for *20 Minutes* |
| 144 | Rinse Slide With Reaction Buffer |
| 145 | Adjust Slide Volume With Reaction Buffer |
| 146 | Apply Coverslip |
| 147 | Rinse Slide With Reaction Buffer |
| 148 | Adjust Slide Volume With Reaction Buffer |
| 149 | Apply One Drop of *SISH DET HRP*, Apply Coverslip, and Incubate for *16 Minutes* |
| 150 | Rinse Slide With Reaction Buffer |
| 151 | Adjust Slide Volume With Reaction Buffer |
| 152 | Apply Coverslip |
| 153 | Rinse Slide With Reaction Buffer |
| 154 | Adjust Slide Volume With Reaction Buffer |
| 155 | Apply Coverslip |
| 156 | Disable Slide Heater |
| 157 | ***** Select Optional Wash ***** |
| 158 | Rinse Slide |
| 159 | Adjust Slide Volume |
| 160 | Apply Coverslip |
| 161 | Rinse Slide |
| 162 | Jet Drain |
| 163 | Apply One Drop of *Silver A*, Apply Coverslip, and Incubate for *4 Minutes* |
| 164 | Rinse Slide |
| 165 | Adjust Slide Volume |
| 166 | Apply Coverslip |
| 167 | Rinse Slide |
| 168 | Adjust Slide Volume |
| 169 | Apply Coverslip |
| 170 | Rinse Slide |
| 171 | Adjust Slide Volume |
| 172 | Apply Coverslip |
| 173 | Rinse Slide |
| 174 | Jet Drain |
| 175 | Apply One Drop of *Silver A*, Apply Coverslip, and Incubate for *4 Minutes* |
| 176 | Apply One Drop of *Silver B*, and Incubate for *4 Minutes* |
| 177 | Apply One Drop of *Silver C*, and Incubate for *12 Minutes* |
| 178 | Rinse Slide |
| 179 | Adjust Slide Volume |
| 180 | Apply Coverslip |
| 181 | Rinse Slide With Reaction Buffer |
| 182 | Adjust Slide Volume With Reaction Buffer |
| 183 | Apply Coverslip |
| 184 | If *Counterstain* is *Selected* |
| 185 | Rinse Slide With Reaction Buffer |
| 186 | Adjust Slide Volume With Reaction Buffer |
| 187 | Apply One Drop of #Counterstain# (*Counterstain*), Apply Coverslip, and Incubate for #Incubation Time# |
| 188 | Rinse Slide With Reaction Buffer |
| 189 | Adjust Slide Volume With Reaction Buffer |
| 190 | Apply Coverslip |
| 191 | If *Post Counterstain* is *Selected* |
| 192 | Rinse Slide With Reaction Buffer |
| 193 | Adjust Slide Volume With Reaction Buffer |
| 194 | Apply One Drop of #Counterstain# (*Post Counterstain*), Apply Coverslip, and Incubate for #Incubation Time# |
| 195 | Rinse Slide With Reaction Buffer |
| 196 | Adjust Slide Volume With Reaction Buffer |
| 197 | Apply Coverslip |
| 198 | ***** Select SSC Wash ***** |
| 199 | ***** Start Timed Steps ***** |
| 200 | Rinse Slide With Reaction Buffer |
| 201 | Adjust Slide Volume With Reaction Buffer |
| 202 | Apply Coverslip |

In brief, after paraffin removal and protease treatment, hybridization with DNP labeled probe was carried out for 2 hours at 50° C. in 2×SSC and 23% formamide. After washing with 2×SSC an anti-DNP antibody (rabbit 7.5 µg/ml) was applied, followed by a 20 minute incubation at 37° C. After washing, a goat anti rabbit antibody conjugated to horseradish peroxidase was applied (20 µg/ml) and incubated an additional 20 minutes. After washing with 100 mM citrate buffer pH 3.6 a solution of silver acetate (3.68 mg/ml) was applied. Four minutes later, without washing, a hydroquinone solution (1.78 mg/ml in 0.1 M citrate pH 3.8 was applied, followed by a solution of 0.09% hydrogen peroxide. After 12 minutes the slide was washed and dried for mounting.

Exemplary SISH results are illustrated in FIG. 6. FIGS. 6A and C are brightfield images, FIGS. 6B and D are negative images which show signal as white spots. FIGS. 6A and B show a sample in which the HER2 target sequence is unamplified (diploid). Cells in this sample exhibit two or fewer hybridization signals (which appear as dark staining in the lightfield and bright staining in the darkfield images). FIGS. 6C and D show a sample in which the HER2 target sequence is amplified to many times the diploid copy number. Hybridization signals appear as a multifocal aggregate.

Example 4

Substantially Unfragmented or Fragmented FPC Nucleic Acid Molecules Detect Target Nucleic Acid Molecules This example describes methods used to demonstrate that unfragmented FPC nucleic acid molecules, as well as fragmented FPC nucleic acid molecules, can be used as a probe to detect a target nucleic acid sequence. Although particular methods for fragmenting FPC nucleic acid molecules are described, one skilled in the art will appreciate that other methods can be used.

The probe containing FPC nucleic acid molecules specific for HER2 described in Example 1 was produced by a method which does not reduce the size of the probe (e.g., by fragmentation or otherwise). This Example demonstrates that a probe containing substantially unfragmented FPC nucleic acid molecules or containing a plurality of fragments FPC nucleic acid molecules each are useful for detection of a target nucleic acid sequence.

After labeling, three aliquots of the FPC nucleic acid molecules specific for HER2 described in Example 1 were placed in separate tubes and heated at 100° C. for 5, 30, or 60 minutes, respectively, to yield a plurality of FPC nucleic acid molecule fragments in different size ranges. Samples of the resulting labeled DNA were analyzed by agarose gel electrophoresis to establish the approximate size range of the FPC nucleic acid molecule fragments in each of the aliquots. As shown in FIG. 7, the probe containing unfragmented FPC nucleic acid molecules (lane 1) barely entered the agarose, which is consistent with its large size (substantially >23 Kb in comparison to the rightmost markers). The size of the probe fragments decreased as a function of the duration of the 100° C. heat treatment. The estimated (approximate) size of the majority of fragments heat treated for the 5 (lane 2), 30 (lane 3), or 60 (lane 4) minutes was approximately 500, 300, or 100 base pairs, respectively.

The probe containing substantially unfragmented and the probe containing fragmented FPC nucleic acid molecule specific for HER2 each were formulated in hybridization buffer and used in the in situ hybridization assay described in Example 3. As shown in FIG. 8, the target HER2 genomic DNA was detected with each probe formulation (left panels of FIGS. 8A-8D) and none of the probe formulations substantially stained HER2-negative tissue sections (right panels of FIGS. 8A-8D).

The strength of the detected signal had an inverse relationship to the length of the probe with the substantially unfragmented probe providing the strongest signal (see the left panel of FIG. 8A as compared to the left panels of FIGS. 8B-D, each of which was stained with progressively smaller probe fragments). This result is contrary to conventional wisdom (see, e.g., Angerer and Angerer, Nuc. Acids Res., 9:2819, 1981) but can be explained, for example, by the formation of a probe network (see FIG. 2B) that is unique to structure of the disclosed nucleic acid probes that include FPC nucleic acid molecules.

Example 5

Viral Genome Probes and Detection of Virus Using Same

This example describes methods used to generate a probe that includes heterogeneous FPC nucleic acid molecules from a viral genomic target. Similar methods can be used to generate a probe including heterogeneous FPC nucleic acid molecules from other viral target nucleic acid sequences.

Detection of viruses in biological samples has many applications in research and clinical settings. The viral genome is one target for detection in a biological sample, and many nucleic acid probes complementary to all or part of the genomes of various viruses are known. A detection assay using a nucleic acid probe complementary to all or substantially all of a complete viral genome typically will be more sensitive than an assay employing a probe specific for a portion of the viral genome because more of the target is covered with detectable moieties. On the other hand, a nucleic acid probe complementary to all or substantially all of a complete viral genome may have residual infectivity, which, depending on the nature of the virus, may pose a hazard to the user. In one example, a disclosed FPC nucleic acid molecule and probes containing such molecules can contain all or substantially all of the content of a complete viral genome, but, because the segments of the viral genome contained in the FPC nucleic acid molecule are combined in random order and orientation, there is little-to-no likelihood that a virus-specific probe made from the FPC nucleic acid molecule is or will become infective.

A. HPV16 Genomic DNA Probe

HPV16 DNA in pGEM2 vector was obtained from Ventana Medical Systems. Alternatively, HPV16 genomic DNA in pBluescript SK⁻ can be obtained from ATCC™ (Cat. No. 45113). The HPV16 DNA was released from the pGEM2 vector by digestion with BamHI. After agarose gel electrophoresis, the HPV DNA was excised from the gel and purified. The purified viral DNA was doubly digestion with AluI and DpnI and, then, incubated with T4 DNA polymerase in the presence of dATP, dTTP, dCTP and dGTP to render the DNA ends flush. The polymerase reaction mixture was extracted with phenol and blunt-ended DNA restriction fragments precipitated with ethanol. Twenty (20) µg of the precipitated DNA restriction fragments were resuspended in a small volume (20 µl) of ligation buffer and ligated using T4 DNA ligase (for approximately 24 hours at room temperature) to generate FPC nucleic acid molecules specific for HPV16 nucleic acids.

The FPC nucleic acid molecules specific for HPV16 nucleic acids was subjected to repeated sequential amplification using random hexamer primers (terminated by 2-phosphorothioates at the 3' end) to generate milligram quantities of permuted HPV16 DNA. This amplification product was labeled with DNP using the Label IT™ DNP labeling kit (MIRUS, Madison, Wis., USA) in conformance with the manufacturer's instructions. The resulting labeled FPC nucleic acid molecules specific for HPV16 nucleic acids was used as a probe on paraffin-embedded, formalin-fixed HPV16-positive Caski or HPV16-negative C33A cell xenograft sections on a Ventana Benchmark™ XT using a standard in situ hybridization protocol provided by the manufacturer (see Table 3). The probe containing FPC nucleic acid molecules specific for HPV16 nucleic acids was detected with a mouse anti-DNP antibody, alkaline-phosphatase-conjugated goat anti-mouse antibody, and corresponding CISH detection reagents (e.g., NBT/BCIP chromogenic substrates).

TABLE 3

| | Exemplary automated CISH staining protocol |
|---|---|
| 1 | ***** Select EZ Prep ***** |
| 2 | **** Start Timed Steps ***** |
| 3 | ***** Mixers Off ***** |
| 4 | Warmup Slide to *65 Deg C.*, and Incubate for *12 Minutes* |
| 5 | Warmup Slide to *75 Deg C.*, and Incubate for *4 Minutes* |
| 6 | Rinse Slide With Reaction Buffer |
| 7 | Apply 600ul of Reaction Buffer |
| 8 | Apply Coverslip |
| 9 | Disable Slide Heater |
| 10 | ***** Mixers On ***** |
| 11 | Warmup Slide to *37 Deg C.*, and Incubate for *4 Minutes* |
| 12 | Rinse Slide |
| 13 | Apply 900ul of Rinse Buffer |
| 14 | Apply Coverslip |
| 15 | Apply Cell Conditioner #2 |
| 16 | Warmup Slide to *90 Deg C.*, and Incubate for *16 Minutes* |
| 17 | Apply 900ul of Reaction Buffer |
| 18 | Apply Coverslip |
| 19 | Disable Slide Heater |
| 20 | Rinse Slide With Reaction Buffer |
| 21 | Adjust Slide Volume With Reaction Buffer |
| 22 | Apply Coverslip |
| 23 | ***** Select SSC Wash ***** |
| 24 | Warmup Slide to *37 Deg C.*, and Incubate for *4 Minutes* |
| 25 | Rinse Slide With Reaction Buffer |
| 26 | Apply 300ul of Reaction Buffer |
| 27 | Apply One Drop of *ISH-PROTEASE 3*, Apply Coverslip, and Incubate for *4 Minutes* |
| 28 | Rinse Slide With Reaction Buffer |
| 29 | Apply 300ul of Reaction Buffer |
| 30 | Apply Coverslip |
| 31 | Disable Slide Heater |
| 32 | Rinse Slide |
| 33 | Adjust Slide Volume |
| 34 | Apply Coverslip |
| 35 | Warmup Slide to *37 Deg C.*, and Incubate for *4 Minutes* |
| 36 | Rinse Slide |
| 37 | Adjust Slide Volume |
| 38 | Apply One Drop of *iVIEW + HybReady*, Apply Coverslip, and Incubate for *4 Minutes* |

TABLE 3-continued

Exemplary automated CISH staining protocol

| | |
|---|---|
| 39 | If *Reference Lot* is *Selected* |
| 40 | Apply Two Drops of *HPV III Fam6(C)*, and Incubate for *4 Minutes* |
| 41 | If *Reference Lot* is *Not Selected* |
| 42 | If *Test Lot* is *Selected* |
| 43 | [Probe 2] |
| 44 | Apply Two Drops of *PROBE 2*, and Incubate for *4 Minutes* |
| 45 | If *Test Lot* is *Not Selected* |
| 46 | If *ISH Negative Control* is *Selected* |
| 47 | Apply One Drop of *ISH NEG CTRL*, and Incubate for *4 Minutes* |
| 48 | Warmup Slide to *95 Deg C.*, and Incubate for *12 Minutes* |
| 49 | Warmup Slide to *52 Deg C.*, and Incubate for *4 Minutes* |
| 50 | Apply Short Coverslip |
| 51 | Incubate for *2 Hours* |
| 52 | Rinse Slide |
| 53 | Apply 900ul of Rinse Buffer |
| 54 | Apply Coverslip |
| 55 | Warmup Slide to *72 Deg C.*, and Incubate for *8 Minutes* |
| 56 | Rinse Slide |
| 57 | Apply 900ul of Rinse Buffer |
| 58 | Apply Coverslip |
| 59 | Warmup Slide to *72 Deg C.*, and Incubate for *8 Minutes* |
| 60 | Rinse Slide |
| 61 | Apply 900ul of Rinse Buffer |
| 62 | Apply Coverslip |
| 63 | Warmup Slide to *72 Deg C.*, and Incubate for *8 Minutes* |
| 64 | Disable Slide Heater |
| 65 | Rinse Slide With Reaction Buffer |
| 66 | Adjust Slide Volume With Reaction Buffer |
| 67 | Apply Coverslip |
| 68 | ***** Procedure Synchronization ***** |
| 69 | Warmup Slide to *37 Deg C.*, and Incubate for *4 Minutes* |
| 70 | Rinse Slide With Reaction Buffer |
| 71 | Adjust Slide Volume With Reaction Buffer |
| 72 | Apply One Drop of *iVIEW + Anti-DNP*, Apply Coverslip, and Incubate for *20 Minutes* |
| 73 | Rinse Slide With Reaction Buffer |
| 74 | Adjust Slide Volume With Reaction Buffer |
| 75 | Apply One Drop of *iVIEW + Amp*, Apply Coverslip, and Incubate for *8 Minutes* |
| 76 | Rinse Slide With Reaction Buffer |
| 77 | Adjust Slide Volume With Reaction Buffer |
| 78 | Apply One Drop of *iVIEW + Biotin-Ig*, Apply Coverslip, and Incubate for *12 Minutes* |
| 79 | Rinse Slide With Reaction Buffer |
| 80 | Adjust Slide Volume With Reaction Buffer |
| 81 | Apply One Drop of *iVIEW + SA-AP*, Apply Coverslip, and Incubate for *8 Minutes* |
| 82 | Rinse Slide With Reaction Buffer |
| 83 | Apply 900ul of Reaction Buffer |
| 84 | Apply Coverslip |
| 85 | Rinse Slide With Reaction Buffer |
| 86 | Adjust Slide Volume With Reaction Buffer |
| 87 | Apply One Drop of *iVIEW + Enhancer*, Apply Coverslip, and Incubate for *4 Minutes* |
| 88 | Apply One Drop of *iVIEW + NBT* and One Drop of *iVIEW + BCIP*, and Incubate for *24 Minutes* |
| 89 | Rinse Slide With Reaction Buffer |
| 90 | Adjust Slide Volume With Reaction Buffer |
| 91 | Apply Coverslip |
| 92 | Disable Slide Heater |
| 93 | Warmup Slide to *37 Deg C.*, and Incubate for *4 Minutes* |
| 94 | Rinse Slide With Reaction Buffer |
| 95 | Adjust Slide Volume With Reaction Buffer |
| 96 | Apply One Drop of *Red Stain II*, Apply Coverslip, and Incubate for *4 Minutes* |
| 97 | Rinse Slide With Reaction Buffer |
| 98 | Adjust Slide Volume With Reaction Buffer |
| 99 | Apply Coverslip |
| 100 | Disable Slide Heater |
| 101 | ***** Select Optional Wash ***** |
| 102 | ***** Select SSC Wash ***** |
| 103 | ***** Start Timed Steps ***** |
| 104 | Rinse Slide With Reaction Buffer |
| 105 | Adjust Slide Volume With Reaction Buffer |
| 106 | Apply Coverslip |

As shown in FIG. 9A, the probe containing FPC nucleic acid molecules specific for HPV16 nucleic acids strongly labeled Caski cell xenograph sections, while, as shown in FIG. 9B, such probe showed no detectable labeling of HPV16-negative C33A cell xenograft sections.

B. Human BK Virus Genomic Probe

BK polyomavirus (prototype strain) genomic DNA in pBR322 was obtained from ATCC™ (Cat. No. 45024). BK virus DNA was released from the vector by digestion with BamHI. After agarose gel electrophoresis, the BK virus DNA was excised from the gel and purified. The purified viral DNA was doubly digestion with AluI and DpnI and, then, incubated with T4 DNA polymerase in the presence of dATP, dTTP, dCTP and dGTP to render the DNA ends flush. The polymerase reaction mixture was extracted with phenol and blunt-ended DNA restriction fragments precipitated with ethanol. Twenty (20) µg of the precipitated DNA restriction fragments were resuspended in a small volume (20 µl) of ligation buffer and ligated using T4 DNA ligase (for approximately 24 hours at room temperature) to generate permuted BK virus nucleic acid template.

The FPC nucleic acid molecules specific for BK virus nucleic acids was subjected to repeated sequential amplification using random hexamer primers (terminated by 2-phosphorothioates at the 3' end) to generate milligram quantities of permuted BK virus DNA. This amplification product was labeled with DNP using the Label IT™ DNP labeling kit (MIRUS, Madison, Wis., USA) in conformance with the manufacturer's instructions. The resulting labeled FPC nucleic acid molecules specific for BK virus nucleic acids was used on a Ventana Benchmark™ XT using a standard in situ hybridization protocol provided by the manufacturer (see e.g., Table 3) to stain paraffin-embedded, formalin-fixed human kidney tissue sections from individuals whose kidneys had or had not been infected with the BK virus. In one series of experiments, the probe containing FPC nucleic acid molecules specific for BK virus nucleic acids was detected with a mouse anti-DNP antibody, alkaline-phosphatase-conjugated goat anti-mouse antibody, and corresponding CISH detection reagents (e.g., NBT/BCIP chromogenic substrates). An alternative detection using mouse anti-DNP antibody, HRP-conjugated goat anti-mouse antibody, and corresponding SISH detection reagents (including silver ions, hydrogen peroxide, and hydroquinone) (see, e.g., U.S. Pat. Nos. 6,670,113 and 7,183,072) was also used.

As shown in FIG. 10, the probe containing FPC nucleic acid molecules specific for BK virus nucleic acids strongly labeled infected human kidney tissue, but did not substantially label non-infected human kidney sections. CISH and SISH detection were equally useful for detecting the probe.

In view of the many possible embodiments to which the principles of the disclosure may be applied, it should be recognized that the illustrated embodiments are only examples of a disclosure and should not be taken as limiting the scope of a disclosure. Accordingly, this disclosure includes all modifications encompassed within the spirit and scope of the disclosure as defined by the following claims:

I claim:

1. A method for producing a permuted nucleic acid probe, comprising:
   ligating at least a first binding region complementary to a first sequence of a target nucleic acid molecule and a second binding region complementary to a second sequence of the target nucleic acid molecule in random order and orientation, thereby producing a plurality of nucleic acid molecules substantially all of which nucleic acid molecules each comprise at least a contiguous first binding region and second binding region, wherein the contiguous first binding region and second binding region are complementary to non-contiguous portions and unique sequences of the target nucleic acid molecule, and wherein the plurality of nucleic acid molecules form the permuted probe.

2. The method of claim 1, further comprising:
   amplifying the plurality of nucleic acid molecules to produce a plurality of nucleic acid molecule amplicons to form the probe.

3. The method of claim 1, wherein the at least first binding region and the second binding region are substantially free of repetitive nucleic acid sequences, conserved domain nucleic acid sequences, or homologous nucleic acid sequences of the target nucleic acid molecule.

4. The method of claim 1, wherein the method further comprises identifying repetitive nucleic acid sequences, conserved domain nucleic acid sequences, or homologous nucleic acid sequences of the target nucleic acid molecule.

5. The method of claim 2, further comprising labeling the plurality of nucleic acid molecule amplicons, to produce a labeled probe.

6. The method of claim 5, wherein the plurality of nucleic acid molecule amplicons are labeled using nick translation.

7. The method of claim 1, wherein the target nucleic acid molecule is from a eukaryotic or viral genome, or from an RNA molecule.

8. The method of claim 1, wherein the target nucleic acid molecule is a genomic nucleic acid molecule.

9. The method of claim 8, wherein the genomic target nucleic acid molecule comprises at least one nucleic acid sequence associated with a disease or a pathogen.

10. The method of claim 8, wherein the genomic target nucleic acid molecule is reduplicated in at least a subset of cells of a neoplasm.

11. The method of claim 1, wherein the at least first binding region and the second binding region are generated by:
(a) isolating the at least first binding region and the second binding region from the target nucleic acid molecule;
(b) obtaining the at least first binding region and the second binding region from the target nucleic acid molecule by subtractive hybridization;
(c) amplifying the at least first binding region and the second binding region from the target nucleic acid molecule; or
(d) any combination of (a), (b) and (c).

12. The method of claim 1, wherein the at least first binding region and the second binding region are isolated or amplified from a target nucleic acid molecule present in a vector.

13. The method of claim 1, comprising:
amplifying a plurality of binding regions that are substantially free of repetitive nucleic acid sequences, conserved domain nucleic acid sequences, or homologous nucleic acid sequences, from a target nucleic acid sequence to produce a plurality of binding region amplicons;
ligating the plurality of binding region amplicons to produce a plurality of nucleic acid molecules substantially all of which nucleic acid molecules each comprise contiguous binding regions that are complementary to non-contiguous portions and unique sequences of a target nucleic acid molecule;
amplifying the plurality of nucleic acid molecules to produce a plurality of nucleic acid molecule amplicons; and
labeling the plurality of nucleic acid molecule amplicons to produce the permuted probe.

14. The method of claim 1, wherein the first binding region and the second binding region comprise less than 10% of undesired sequences selected from the group consisting of repetitive nucleic acid sequences, conserved domain nucleic acid sequences, and homologous nucleic acid sequences of the target nucleic acid molecule.

15. The method of claim 1, wherein the first binding region and the second binding region are free of repetitive nucleic acid sequences of the target nucleic acid molecule.

16. The method of claim 1, wherein the first binding region and the second binding region comprise 1% to 5% repetitive nucleic acid sequences, conserved domain nucleic acid sequences, and/or homologous nucleic acid sequences of the target nucleic acid molecule.

17. The method of claim 1, wherein at least 80% of the repetitive nucleic acid sequences, conserved domain nucleic acid sequences, and/or homologous nucleic acid sequences are removed from the target nucleic acid molecule.

18. The method of claim 1, wherein at least 90% of the repetitive nucleic acid sequences, conserved domain nucleic acid sequences, and/or homologous nucleic acid sequences are removed from the target nucleic acid molecule.

19. The method of claim 1, wherein at least 95% of the repetitive nucleic acid sequences, conserved domain nucleic acid sequences, and/or homologous nucleic acid sequences are removed from the target nucleic acid molecule.

20. The method of claim 1, wherein at least 99% of the repetitive nucleic acid sequences, conserved domain nucleic acid sequences, and/or homologous nucleic acid sequences are removed from the target nucleic acid molecule.

21. The method of claim 1, wherein the first binding region and the second binding region are entirely free of repetitive nucleic acid sequences, conserved domain nucleic acid sequences, and homologous nucleic acid sequences of the target nucleic acid molecule.

22. The method of claim 1, wherein the target nucleic acid molecule is at least 10,000 base pairs in length.

23. The method of claim 1, wherein the target nucleic acid molecule is at least 100,000 base pairs in length.

24. The method of claim 1, wherein the target nucleic acid molecule is at least 500,000 base pairs in length.

25. The method of claim 1, wherein the first binding region or the second binding region is completely free of repetitive nucleic acid sequences.

26. The method of claim 1, wherein the first binding region or the second binding region is completely free of repetitive nucleic acid sequences, conserved domain nucleic acid sequences, and homologous nucleic acid sequences of the target nucleic acid molecule.

27. The method of claim 1, wherein the first binding region and the second binding region comprise less than 1% of undesired sequences selected from the group consisting of repetitive nucleic acid sequences, conserved domain nucleic acid sequences, or homologous nucleic acid sequences of the target nucleic acid molecule.

28. The method of claim 1, wherein the first binding region and the second binding region comprise less than 0.01% of undesired sequences selected from the group consisting of repetitive nucleic acid sequences, conserved domain nucleic acid sequences, or homologous nucleic acid sequences of the target nucleic acid molecule.

29. The method of claim 1, wherein the first binding region and the second binding region are each at least 500 nucleotides in length.

30. The method of claim 1, wherein the plurality of nucleic acid molecules substantially each comprise at least 1000 nucleotides.

31. The method of claim 1, wherein the plurality of nucleic acid molecules comprises at least 1000 different nucleic acid molecules.

* * * * *